United States Patent [19]

Yoshimura et al.

[11] Patent Number: 4,826,834
[45] Date of Patent: May 2, 1989

[54] CEPHEM COMPOUNDS

[75] Inventors: Yoshinobu Yoshimura, Ibaraki; Naoto Hashimoto, Suita; Shoji Kishimoto, Takarazuka, all of Japan

[73] Assignee: Takeda Chemical Industries, Ltd., Japan

[21] Appl. No.: 909,942

[22] Filed: Sep. 22, 1986

[30] Foreign Application Priority Data

Sep. 27, 1985 [JP] Japan .................. 60-216051
Sep. 1, 1986 [JP] Japan .................. 61-206574

[51] Int. Cl.$^4$ .................. C07D 50/46; A61K 31/545
[52] U.S. Cl. .................. 514/207; 514/202; 514/205; 540/222; 540/225; 540/227; 540/350
[58] Field of Search .................. 540/225, 222, 227; 514/205, 207, 202

[56] References Cited

U.S. PATENT DOCUMENTS 4,165,430  8/1979  Bradshaw .................. 544/22
4,665,065  5/1987  Miyake et al. .................. 540/222

FOREIGN PATENT DOCUMENTS 82102818.0  2/1982  European Pat. Off. .
0062321    10/1982  European Pat. Off. .
85100326.9  1/1985  European Pat. Off. .
0137441     4/1985  European Pat. Off. .
0149487     7/1985  European Pat. Off. .
84111745.0 10/1985  European Pat. Off. .
2036724     7/1980  United Kingdom .

*Primary Examiner*—Nicholas S. Rizzo
*Attorney, Agent, or Firm*—Wegner & Bretschneider

[57] ABSTRACT

A compound having the general formula

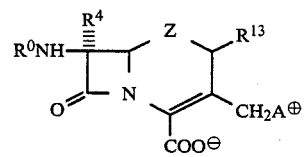

wherein, $R^0$ is a hydrogen atom, a nitrogen-containing heterocyclic group, an acyl group or an amino-protective group; Z is S, S→O,O or $CH_2$; $R^4$ is a hydrogen atom, a methoxy group, or a formamide group; $R^{13}$ is a hydrogen atom, a methyl group, a hydroxyl group, or a halogen atom; A⊕ is a condensed triazolio group which may be substituted, or a pharmaceutically acceptable salt or ester thereof is novel and has an excellent antibacterial activity.

12 Claims, No Drawings

CEPHEM COMPOUNDS

This invention relates to novel antimicrobial compounds having an excellent antibacterial activity and to methods for the production and pharmaceutical compositions thereof.

More specifically, this invention relates to compounds having the general formula

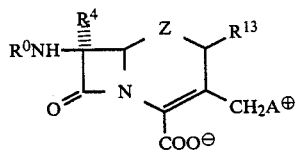

[I]

wherein $R^0$ is a hydrogen atom, a nitrogen-containing heterocyclic group, an acyl group or an amino protective group; Z is S, S→O, O or $CH_2$; $R^4$ is a hydrogen atom, a methoxy group, or a formamido group; $R^{13}$ is a hydrogen atom, a methyl group, a hydroxy group or a halogen atom; $A^\oplus$ is a condensed triazolio group which group may be substituted, or pharmaceutically acceptable salts or esters thereof, and to the methods for production and pharmaceutical composition thereof. Specifically, the antibacterial compound of this invention is a cephem compound having the general formula [I](Z=S, S→O), or an oxa derivative (Z=O, or a carba derivative (Z=$CH_2$)wherein $R^0$ is nitrogen-containing heterocyclic group or an acyl group. Hereinafter, unless otherwise stated, a compound [I] in this specification includes also a pharmaceutically acceptable salt or ester thereof.

The cephem compounds described in this specification have been named according to "Cepham" in "The Journal of the American Chemical Society" Vol. 84, p. 3400 (1962); a cephem compound means a cepham compound having a double bond at the 3,4-position in the molecule.

Various cephem compounds having each a quaternary ammonium methyl group at the 3 position together with 2-(2-aminothiazol-4-yl)-2-hydroxy (or substituted hydroxy)iminoacetamido group at the 7 position, and derivatives thereof have been synthesized so far and application for patent thereon have been filed[for example, Japanese Patent Application Laid-Open No. 34795/78, No. 9296/79, No. 135792/79, No. 154786/79, No. 149289/80, No. 56485/82, No. 192394/82, No. 159498/83, and so on], and most of the compounds have a quaternary ammonium methyl group at the 3 position derived from a substituted or non-substituted monocyclic pyridinium group among the nitrogen-containing aromatic heterocyclic rings. A compound of this invention which contains a condensed triazolio group has neither been synthesized yet, nor been disclosed in the specification of an application for patent. The present inventors have succeeded in synthesizing the compounds of the general formula [I] having such chemical structural characteristics, and found from studies of the antimicrobial activity and antibacterial spectra of these compounds that compounds [I] wherein $R^0$ is a nitrogen-containing heterocyclic group or an acyl group have a potent antibacterial activity against various bacteria, particularly agarnst cephalosporin-resistant bacteria described above and that it has a unique antimicrobial activity against Pseudomonas sp., etc., thus completing this invention.

In the following the group names and symbols used in this specification are explained. Unless otherwise noted, the names of groups and symbols in this specification mean the following:

"An alkyl group" is preferably a straight chain or branched lower alkyl grcup having 1 to 6 carbon atoms (hereinafter sometimes abbreviated as "a $C_{1-6}$alkyl group"), such as a methyl, ethyl, n-propyl, isopropyl, n-butyl, isobutyl, sec-butyl, tert-butyl, n-pentyl, or n-hexyl group.

"An alkenyl group" is preferably a straight chain or branched lower alkenyl group having 2 to 6 carbon atoms (hereinafter sometimes abbreviated as "a $C_{2-6}$ alkenyl group"), such as vinyl, allyl, 1-propenyl, isopropenyl, 1-butenyl, 2-butenyl, 3-butenyl, methallyl, or 1,1-dimethylallyl group.

"An alkynyl group" is preferably a straight chain or branched lower alkynyl group having 2 to 6 carbon atoms (hereinafter sometimes abbreviated as "a $C_{2-6}$alkynyl group"), such as ethynyl, 1-propynyl, or propargyl group.

"A cycloalkyl group" is preferably a 3 to 7 membered (ali)cyclic alkyl group having 3 to 10 carbon atoms (hereinafter sometimes abbreviated as "a $C_{3-10}$cycloalkyl group"), such as a cyclopropyl, cyclobutyl, cyclopentyl, cyclohexyl, cycloheptyl, norbornyl, or adamantyl group.

"A cycloalkenyl group" is preferably a 5 to 6 membered (ali)cyclic hydrocarbon group containing one or two double bond(s) (hereinafter sometimes abbreviated as "a $C_{5-6}$cycloalkenyl group"), such as a cyclopentenyl, cyclopentadienyl, cyclohexenyl, or cyclohexadienyl group.

"An aryl group" is preferably an aromatic hydrocarbon group having 6 to 12 carbon atoms, such as phenyl, α-naphthyl, β-naphthyl, or biphenyl group, more preferably one having 6 to 10 carbon atoms (hereinafter sometimes abbreviated as "a $C_{6-10}$aryl group").

"An aralkyl group" is preferably an aromatic-substituted alkyl group having 7 to 12 carbon atoms (hereinafter sometimes abbreviated as a"$C_{7-12}$aralkyl group"), such as benzyl, 1-phenylethyl, 2-phenylethyl, phenylpropyl, or naphthylmethyl group. A $C_{7-12}$aralkyl, di$C_{6-10}$aryl-methyl and tri$C_{6-10}$aryl-methyl group described below is altogether described sometimes as "a $C_{7-19}$aralkyl group". "A diarylmethyl group" means a methyl group substituted with two $C_{6-10}$aryl groups described above (hereinafter sometimes abbreviated as "a di$C_{6-10}$aryl-methyl group), such as a benzhydryl group.

"A triarylmethyl group" means a methyl group substituted with three $C_{6-10}$aryl groups described above (hereinafter sometimes abbreviated as "a tri$C_{6-10}$aryl-methyl group"), such as a trityl group.

An aryl group in "an arylmethylene group" is desirably the $C_{6-10}$aryl group described above, and therefore "an arylmethylene group" is sometimes abbreviated as "a $C_{6-10}$arylmethylene group" hereinafter. Such a $C_{6-10}$aryl-methylene group includes a benzylidene ($C_6H_5CH=$) group.

An alkyl group in "an alkoxy group" is preferably the $C_{1-6}$alkyl group described above, and therefore "an alkoxy group" is sometimes written as "a $C_{1-6}$alkoxy group". Such a $C_{1-6}$alkoxy group includes a methoxy, ethoxy, n-propoxy, isopropoxy, n-butoxy, tert-butoxy, pentyloxy, and hexyloxy group.

A cycloalkyl group in "a cycloalkyloxy group" is preferably the $C_{3-10}$cycloalkyl group described above, and therefore "a cycloalkyloxy group" is sometimes abbreviated as "a $C_{3-10}$cycloalkyloxy group" hereinafter. Such a $C_{3-10}$cycloalkyloxy group includes a cyclopropyloxy, cyclopentyloxy, cyclohexyloxy, and norbornyloxy group.

An aryl group in "an aryloxy group" is preferably the $C_{6-10}$aryl group described above, and therefore "an aryloxy group" is sometimes abbreviated as "a $C_{6-10}$aryloxy group" hereinafter.

Such a $C_{6-10}$aryloxy group includes a phenoxy and naphthyloxy group.

An aralkyl group in "an aralkyloxy group" is preferably a $C_{7-19}$aralkyl group, and therefore "an aralkyloxy group" is sometimes written as "an $C_{7-19}$aralkyloxy group" hereinafter. Such a $C_{7-19}$aralkyloxy group includes a benzyloxy, 1-phenylethyloxy, 2-phenylethyloxy, naphthylmethyloxy, benzhydryloxy, and trityloxy group.

An alkyl group in "an alkylthio group" is preferably the $C_{1-6}$alkyl group described above, and therefore "an alkylthio group" is sometimes written as "an $C_{1-6}$alkylthio group" hereinafter. Such a $C_{1-6}$alkylthio group includes a methylthio, ethylthio, n-propylthio, and n-butylthio group.

An alkylthio group in "an aminoalkylthio group" is preferably the $C_{1-6}$alkylthio group described above, and therefore "an aminoalkylthio group" is sometimes written as "an amino$C_{1-6}$alkylthio group" hereinafter. Such an amino$C_{1-6}$alkylthio group includes an aminomethylthio, 2-aminoethylthio, and 3-aminopropylthio group.

An alkenyl group in "an alkenylthio group" is preferably the $C_{2-6}$alkenylthio group described above, and therefore "an alkenylthio group" is sometimes written as "a $C_{2-6}$alkenylthio group" hereinafter. Such a $C_{2-6}$alkenylthio group includes a vinylthio, allylthio, 1-propenylthio, and isopropenylthio group.

A cycloalkyl group in "a cycloalkylthio group" is preferably the $C_{3-10}$cycloalkylthio group described above, and therefore "a cycloalkylthio group" is sometimes written as "a $C_{3-10}$cycloalkylthio group" hereinafter. Such a $C_{3-10}$cycloalkylthio group includes a cyclopropylthio, and cyclohexylthio group.

An aryl group in "an arylthio group" is preferably the $C_{6-10}$aryl group described above, and therefore "an arylthio group" is sometimes written as "an $C_{6-10}$arylthio group" hereinafter. Such a $C_{6-10}$arylthio group includes a phenylthio and naphthylthio group.

An aralkyl group in "an aralkylthio group" is preferably a $C_{7-19}$aralkyl group described above, and therefore "an aralkylthio group" is sometimes written as "a $C_{7-19}$aralkylthio group" hereinafter. Such a $C_{7-19}$aralkylthio group includes a benzylthio, phenylethylthio, benzhydrylthio, and tritylthio group.

An alkyl group in "a monoalkylamino group" is preferably the $C_{1-6}$alkyl group described above, and therefore "a monoalkylamino group" is sometimes written as "a mono$C_{1-6}$alkylamino group" hereinafter. Such a mono$C_{1-6}$alkylamino group includes a methylamino, ethylamino, n-propylamino, n-butylamino, tert-butylamino, n-pentylamino, and n-hexylamino group.

An alkyl group in "a dialkylamino group" is preferably the $C_{1-6}$alkyl group described above, and therefore "a dialkylamino group" is sometimes written as "a di$C_{1-6}$alkylamino group" hereinafter. Such a di$C_{1-6}$alkylamino group includes a dimethylamino, diethylamino, methylethylamino, di-(n-propyl)amino, and di-(n-butyl)amino group.

An alkyl group in "a trialkylammonium group" is preferably the $C_{1-6}$alkyl group described above, and therefore "a trialkylammonium group" is sometimes written as "a tri$C_{1-6}$alkylammonium group" hereinafter. Such a tri$C_{1-6}$alkylammonium group includes a trimethylammonium[*$CH_3)_3N^+$—], and triethylammonium group. A trialkylammonium group is always accompanied by a corresponding anion. Such a anion includes a hydroxide, halide (a chloride, bromide, or iodide ion etc.), sulfate, nitrate, carbonate, organic carboxylate (e.g. an oxalate, or trifluoroacetate ion), and organic sulfonate ion (e.g. a methanesulfonate ion, or p-toluenesulfonate ion). In the case of organic carboxylate ions and organic sulfonate ions, they may form intramolecular salts.

A cycloalkyl group in "a cycloalkylamino group is preferably the $C_{3-10}$cycloalkyl group described above, and therefore "a cycloalkylamino group" is sometimes written as "a $C_{3-10}$cycloalkylamino group" hereinafter. Such a $C_{3-10}$cycloalkylamino group includes a cyclopropylamino, cyclopentylamino, and cyclohexylamino group.

An aryl group in "an arylamino group" is preferably the $C_{6-10}$aryl group described above, and therefore "an arylamino group" is sometimes written as "a $C_{6-10}$arylamino group" hereinafter. Such a $C_{6-10}$arylamino group includes an anilino, and N-methylanilino group.

An aralkyl group in "an aralkylamino group" is preferably the $C_{7-19}$aralkyl group described above, and therefore "an aralkylamino group" is sometimes written as "a $C_{7-19}$aralkylamino group" hereinafter. Such a $C_{7-19}$aralkylamino group includes a benzylamino, 1-phenylethylamino, 2-phenylethylamino, benzhydrylamino, and tritylamino group.

"A cyclic amino group" means a group which is formed by removal of a hydrogen atom bound to the ring-constituting nitrogen atom in a nitrogen-containing heterocycle which is saturated or unsuturated, and the group is exemplified by a 1H-tetrazol-1-yl, 1H-pyrrol-1-yl, pyrrolino, pyrrolidino, 1H-imidazol-1-yl, imidazolino, imidazolidino, 1H-pyrazol-1-yl, pyrazolino, pyrazolidino, piperidino, piperadino, and morpholino group. An alkyl group in "a hydroxyalkyl group" is preferably the $C_{1-6}$alkyl group described above, and therefore "a hydroxyalkyl group" is sometimes written as "a hydrox alkyl group". Such a hydroxy$C_{1-6}$alkyl group includes a hydroxymethyl, 1-hydroxyethyl, 2-hydroxyethyl, and 3-hydroxypropyl group.

An alkyl group in "a mercaptoalkyl group" is preferably the $C_{1-6}$alkyl group, and therefore "a mercaptoalkyl group" is sometimes written as "a mercapto$C_{1-6}$alkyl group" hereinafter. Such a mercapto$C_{1-6}$alkyl group includes a mercaptomethyl, 1-mercaptoethyl, and 2-mercaptoethyl group.

An alkoxy and an alkyl group in "an alkoxyalkyl group" are preferably the $C_{1-6}$alkoxy and $C_{1-6}$alkyl groups described above, respectively, and therefore "an alkoxylalkyl group" is sometimes written as "a $C_{1-6}$alkoxy$C_{1-6}$alkyl group" hereinafter. Such a $C_{1-6}$alkoxy$C_{1-6}$alkyl group includes a methoxymethyl, ethoxymethyl, and 2-methoxyethyl group.

An alkylthio and an alkyl groups in "an alkylthioalkyl group" are preferably the $C_{1-6}$alkylthio and $C_{1-6}$alkyl groups described above, respectively, and therefore "an alkylthioalkyl group" is sometimes written as "a $C_{1-6}$alkylthio$C_{1-6}$alkyl group" hereinafter Such a $C_{1-6}$alkylthio$C_{1-6}$alkyl group includes a methylthiomethyl, and 2-methylthioethyl group.

An alkyl group in "an aminoalkyl group" is preferably the $C_{1-6}$alkyl group described above, and therefore "an aminoalkyl group" is sometimes written as "an aminoC$_{1-6}$alkyl group" hereinafter. Such a aminoC$_{1-6}$alkyl group includes an aminomethyl, 2-aminoethyl, and 3-aminopropyl group.

"A monoalkylaminoalkyl group" is preferably "a monoC$_{1-6}$alkylaminoC$_{1-6}$alkyl group", such as a methylaminomethyl, ethylaminomethyl, 2-(N-methylamino)ethyl, and 3-(N-methylamino)propyl group.

"A dialkylaminoalkyl group" is preferably "a diC$_{1-6}$alkylaminoC$_{1-6}$alkyl group", such as a N,N-dimethylaminomethyl, N,N-diethylaminomethyl, 2-(N,N,dimethylamino)ethyl, 2-(N,N-diethylamino)ethyl, and 3-(N,N-dimethylamino)propyl group.

A cyclic amino group in "a cyclic aminoalkyl group" is preferably the one described above, and the alkyl group is preferably the C$_{1-6}$alkyl group described above, and therefore, "a cyclic aminoalkyl group" is sometimes written as "a cyclic aminoC$_{1-6}$alkyl group" hereinafter. Such a cyclic aminoC$_{1-6}$alkyl group includes a pyrrolidinomethyl, piperidinomethyl, piperazinomethyl, morpholinomethyl, and 2-(morpholino)ethyl group.

A cyclic aminoalkyl group in "a cyclic aminoalkylamino group" is preferably the cyclic aminoC$_{1-6}$alkyl group described above, and therefore, "a cyclic aminoalkylamino group" is sometimes written as "a cyclic aminoC$_{1-6}$alkylamino group" hereinafter. Such a cyclic aminoC$_{1-6}$alkylamino group includes a pyrrolidinomethylamino, piperidinomethylamino, piperazinomethylamino, and morpholinomethylamino group.

An alkyl group in "a halogenoalkyl group" is preferably the C$_{1-6}$alkyl group described above, and therefore "a halogenoalkyl group" is sometimes written as "a halogenoC$_{1-6}$alkyl group" hereinafter. Such a halogenoC$_{1-6}$alkyl group includes a fluoromethyl, difluoromethyl, trifluoromethyl, chloromethyl, dichloromethyl, trichloromethyl, 2-fluoroethyl, 2,2-difluoroethyl, 2,2,2-trifluoroethyl, 2-chloroethyl, 2,2-dichloroethyl, 2,2,2-trichloroethyl, 2-bromoethyl, and 2-iodoethyl group.

An alkyl group in "a cyanoalkyl group" is preferably a C$_{1-6}$alkyl group described above, and therefore "a cyanoalkyl group" is sometimes written as "a cyanoC$_{1-6}$alkyl group" hereinafter. Such a cyanoC$_{1-6}$alkyl group includes a cyanomethyl, and 2-cyanoethyl group.

An alkyl group in "a carboxyalkyl group" is preferably a C$_{1-6}$alkyl group described above, and therefore "a carboxyalkyl group" is sometimes written as "a carboxyC$_{1-6}$alkyl group" hereinafter. Such a carboxyC$_{1-6}$alkyl group includes a carboxymethyl, 1-carboxyethyl, and 2-carboxyethyl group.

An alkyl group in "a sulfoalkyl group" is preferably a C$_{1-6}$alkyl group described above, and therefore "a sulfoalkyl group" is sometimes written as "a sulfoC$_{1-6}$alkyl group" hereinafter. Such a sulfoC$_{1-6}$alkyl group includes a sulfomethyl and 2-sulfoethyl group.

An alkanoyl and an alkyl groups in "an alkanoylalkyl group" are preferably the C$_{2-6}$alkanoyl group described below and the C$_{1-6}$alkyl group described above, respectively, and therefore "an alkanoylalkyl group" is sometimes written as "a C$_{2-6}$alkanoylC$_{1-6}$alkyl group" hereinafter. Such a C$_{2-6}$alkanoylC$_{1-6}$alkyl group includes an acetylmethyl, 1-acetylethyl, and 2-acetylethyl group.

An alkanoyloxy and an alkyl groups in "an alkanoyloxyalkyl group" are preferably the C$_{2-6}$alkanoyloxy group described below and the C$_{1-6}$alkyl group described above, and therefore "an alkanoyloxyalkyl group" is sometimes written as "a C$_{2-6}$alkanoyloxyC$_{1-6}$alkyl group" hereinafter. Such a C$_{2-6}$alkanoyloxyC$_{1-6}$alkyl groupincludes an acetoxymethyl, 1-acetoxyethyl, and 2-acetoxyethyl group.

An alkoxycarbonyl and an alkyl groups in "an alkoxycarbonylalkyl group" are preferably the C$_{1-10}$alkoxycarbonyl group described below and the C$_{1-6}$alkyl group described above, respectively, and therefore "an alkoxycarbonylalkyl group" is sometimes written as "a C$_{1-10}$alkoxycarbonylC$_{1-6}$alkyl group" hereinafter. Such a C$_{1-10}$alkoxycarbonylC$_{1-6}$alkyl group includes a methoxycarbonylmethyl, ethoxycarbonylmethyl, and tert-butoxycarbonylmethyl group.

An alkyl group in "a carbamoylalkyl group" is preferably a C$_{1-6}$alkyl group, and therefore "a carbamoylalkyl group" is sometimes written as "a carbamoylC$_{1-6}$alkyl group" hereinafter. Such a carbamoylC$_{1-6}$alkyl group includes a carbamoylmethyl group.

An alkyl group in "a carbamoyloxyalkyl group" is preferably a C$_{1-6}$alkyl group, and therefore "a carbamoyloxyalkyl group" is sometimes written as "a carbamoyloxyC$_{1-6}$alkyl group" hereinafter. Such a carbamoylox alkyl group includes a carbamoyloxymethyl group.

"A halogen atom" is fluorine, chlorine, bromine or iodine.

"An alkanoyl group is preferably an aliphatic acyl group having 1 to 6 carbon atoms (hereinafter sometimes abbreviated as "a C$_{1-6}$alkanoyl group"), such as a formyl, acetyl, propionyl, butyryl, isobutyryl, valeryl, isovaleryl, and pivaloyl group. These alkanoyl groups except the formyl group are sometimes written as "a C$_{2-6}$alkanoyl group".

"An alkenoyl group" is preferably an alkenoyl group having 3 to 5 carbon atoms (hereinafter sometimes abbreviated as "a C$_{3-5}$alkenoyl group"), such as an acryloyl, crotonoyl and maleoyl group.

A cycloalkyl group in "a cycloalkylcarbonyl group" is preferably the C$_{3-10}$cycloalkyl group described above, and therefore "a cycloalkylcarbonyl gtoup" is sometimes written as "a C$_{3-10}$cycloalkylcarbonyl group" hereinafter. Such a C$_{3-10}$cycloalkylcarbonyl group includes a cyclopropylcarbonyl, cyclobutylcarbonyl, cyclopentylcarbonyl, cyclohexylcarbonyl, cycloheptylcarbonyl, and adamantylcarbonyl group.

A cycloalkenyl group in "a cycloalkenylcarbonyl group" is preferably a C$_{5-6}$cycloalkenyl group, and therefore "a cycloalkenylcarbonyl group" is sometimes written as "a C$_{5-6}$cycloalkenylcarbonyl group" hereinafter. Such a C$_{5-6}$cycloalkenylcarbonyl group includes a cyclopentenylcarbonyl, cyclopentadienylcarbonyl, cyclohexenylcarbonyl, and cyclohexadienylcarbonyl group.

An aryl group in "an arylcarbonyl group" is preferably a C$_{6-10}$aryl group described above, and therefore "an arylcarbonyl group" is sometimes written as "a C$_{6-10}$arylcarbonyl group" hereinafter. Such a C$_{6-10}$arylcarbonyl group includes a benzoyl and naphthoyl group.

An aralkyl group in "an aralkylcarbonyl group" is preferably a C$_{7-19}$aralkyl group described above, and therefore "an aralkylcarbonyl group" is sometimes written as "a C$_{7-19}$aralkylcarbonyl group" hereinafter. Such a C$_{7-19}$aralkylcarbonyl group includes a phenylacetyl, phenylpropionyl, α,α-diphenylacetyl, and α, α,α-triphenylacetyl group.

An alkyl group in "an alkoxycarbonyl group" is defined to include not only a lower alkyl group having 1 to 8 carbon atoms but also the $C_{3-10}$cycloalkyl group described above. Therefore an alkoxycarbonyl group is sometimes written as "a $C_{1-10}$alkoxycarbonyl group" hereinafter. Such a $C_{1-10}$alkoxycarbonyl group includes a methoxycarbonyl, ethoxycarbonyl, n-propoxycarbonyl, isopropoxycarbonyl, n-butoxycarbonyl, isobutoxycarbonyl, tert-butoxycarbonyl, cyclopentyloxycarbonyl, cyclohexyloxycarbonyl, and norbornyloxycarbonyl group.

An aryloxy group in "a aryloxycarbonyl group" is preferably the $C_{6-10}$aryloxy group described above, and therefore "an aryloxycarbonyl group" is sometimes written as "a $C_{6-10}$aryloxycarbonyl group hereinafter. Such a $C_{6-10}$ aryloxycarbonyl group includes a phenoxycarbonyl, and naphthyloxycarbonyl group.

An aralkyloxy group in "an aralkyloxycarbonyl group" is preferably the $C_{7-19}$aralkyloxy group described above, such as a benzyloxycarbonyl, benzhydryloxycarbonyl, and trityloxycarbonyl group.

"A substituted oxycarbonyl group" means the $C_{1-19}$alkoxycarbonyl, $C_{6-10}$aryloxycarbonyl or $C_{7-19}$aralkyloxycarbonyl group described above.

An alkylthio group in "an alkylthiocarbonyl group" is preferably the $C_{1-6}$alkylthio group described above, and therefore "an akkylthiocarbonyl group" is sometimes written as "a $C_{1-6}$alkylthiocarbonyl group" hereinafter. Such a $C_{1-6}$alkylthiocarbonyl group includes a methylthiocarbonyl, ethylthiocarbonyl, n-propylthiocarbonyl, and n-butylthiocarbonyl group.

An alkanoyl group in "an alkanoyloxy group" is preferably the $C_{1-6}$alkanoyloxy group described above, and therefore "an alkanoyloxy group" is sometimes written as "a $C_{1-6}$alkanoyloxy group" hereinafter. Such a $C_{1-6}$alkanoyloxy group includes a formyloxy, acetoxy, propionyloxy, butyryloxy, valeryloxy, and pivaloyloxy group. These alkanoyloxy groups except formyloxy group are sometimes written as "$C_{2-6}$alkanoyloxy groups".

An alkenoyl group in "an alkenoyloxy group" is preferably the $C_{3-5}$alkenoyl group described above, and therefore "an alkenoyloxy group" is sometimes written as "a $C_{3-5}$alkenoyloxy group" hereinafter. Such a $C_{3-5}$alkenoyloxy group includes an acryloyloxy, and crotonoyloxy group.

An alkyl group in "a monoalkylcarbamoyl group" is preferably a $C_{1-6}$alkyl group, and therefore "a monoalkylcarbamoyl group" is sometimes written as "a mono$C_{1-6}$alkylcarbamoyl group" hereinafter. Such a mono$C_{1-6}$alkylcarbamoyl group includes a N-methylcarbamoyl, and N-ethylcarbamoyl group.

An alkyl group in "a dialkylcarbamoyl group" is preferably a $C_{1-6}$alkyl group, and therefore "a dialkylcarbamoyl group" is sometimes written as "a di$C_{1-6}$alkylcarbamoyl group" hereinafter. Such a di$C_{1-6}$alkylcarbamoyl group includes a N,N-dimethylcarbamoyl, and N,N-diethylcarbamoyl group.

A monoalkylcarbamoyl group in "a monoalkylcarbamoyloxy group" is preferably the mono$C_{1-6}$alkylcarbamoyl group described above, and therefore "a monoalkylcarbamoyloxy group" is sometimes written as "a mono$C_{1-6}$alkylcarbamoyloxy group" hereinafter. Such a mono$C_{1-6}$alkylcarbamoyloxy group includes a N-methylcarbamoyloxy, and N-ethylcarbamoyloxy group.

A dialkylcarbamoyl group in "a dialkylcarbamoyloxy group" is preferably the di$C_{1-6}$alkylcarbamoyl group described above, and therefore "a dialkylcarbamoyloxy group" is sometimes written as "a di$C_{1-6}$alkylcarbamoyloxy group" hereinafter. Such a di$C_{1-6}$alkylcarbamoyloxy group includes a N,N-dimethylcarbamoyloxy, and N,N-diethylcarbamoyloxy group.

An alkyl group in "an alkylsufonyl group" is preferably a $C_{1-6}$alkyl group described above, and therefore "an alkylsulfonyl group" is sometimes written as "a di$C_{1-6}$alkylsulfonyl group" hereinafter. Such a $C_{1-6}$alkylsulfonyl group includes a methanesulfonyl, and ethanesulfonyl group.

An aryl group in "an arylsulfonyl group" is preferably the $C_{6-10}$aryl group described above, and therefore "an arylsufonyl group" is sometimes written as "a $C_{6-10}$arylsulfonyl group" hereinafter. Such a $C_{6-10}$arylsulfonyl group includes a benzenesulfonyl group.

An aralkyl group in "an aralkylsulfonyl group" is preferably the $C_{7-19}$aralkyl group described above, and therefore "an aralkylsulfonyl group".is sometimes written as "a $C_{7-19}$aralkylsulfonyl group". Such a $C_{7-19}$aralkylsulfonyl group includes a phenylmethanesulfonyl, and diphenylmethanesulfonyl group.

An alkylsulfonyl group in "an alkylsulfonyloxy group" is preferably the $C_{1-6}$alkylsulfonyl group described above, and therefore "an alkylsulfonyloxy group" is sometimes written as "a $C_{1-6}$alkylsulfonyloxy group" hereinafter. Such a $C_{1-6}$alkylsulfonyloxy group includes a methanesulfonyloxy, and ethanesulfonyloxy group.

An arylsulfonyl group in "an arylsulfonyloxy group" is preferably the $C_{6-10}$arylsulfonyl group described above, and therefore "an arylsulfonyloxy group" is sometimes written as "a $C_{6-10}$arylsulfonyloxy group" hereinafter. Such a $C_{6-10}$arylsulfonyloxy group includes a benzenesulfonyloxy group.

An aralkylsulfonyl group in "an aralkylsulfonyloxy group" is preferably the $C_{7-19}$aralkylsulfonyl group described above, and therefore "an aralkylsulfonyloxy group" is sometimes written as "a $C_{7-19}$aralkylsulfonyloxy group" hereinafter. Such a $C_{7-19}$aralkylsulfonyloxy group includes a phenylmethanesulfonyloxy and diphenylmethanesulfonyloxy group.

"An amino acid residue" means an acyl group formed by removal of the hydroxy group from the carboxyl group in an amino acid. Such an amino acid residue includes a glycyl, alanyl, valyl, leucyl, isoleucyl, seryl, threonyl, cysteinyl, cystyl, methionyl, aspartyl, glutamyl, lysyl, arginyl, phenylglycyl, phenylalanyl, tryosyl, histidyl, tryptophyl, and prolyl group. Hereinafter, the amino acid in such a residue includes not only L-form but also D-form.

"A nitrogen-containing heterocyclic ring" is a 5- to 8-membered ring containing one to several, preferably one to four nitrogen atoms (which may be oxidized), or condensed ring thereof. Such a nitrogen-containing heterocyclic ring may contain, in addition to the nitrogen atom, one to several, preferably 1 or 2 hetero atoms, such as oxygen atom(s) or sulfur atom(s).

"A nitrogen-containing heterocyclic group" is a group formed by removal of one of the hydrogen atoms bound to the ring-constituting carbon atom.

"A heterocyclic group" is a group formed by removal of one of the hydrogen atoms bound to the carbon atoms constituting a heterocyclic ring. Such a heterocyclic ring includes a 5- to 8-membered ring containing one to several, preferably 1 to 4 heteroatoms such as nitrogen atoms (which may be oxidized), oxygen atoms, and sulfur atoms, or condensed rings thereof. Such a heterocyclic group includes a 2- or 3-pyrrolyl, 3-, 4-, or 5-pyrazolyl, 2-, 4-, or 5-imidazolyl, 1,2,3- or 1,2,4-triazolyl, 1H- or 2H-tetrazolyl, 2- or 3-furyl, 2- or 3-thienyl, 2-, 4-, or 5-oxazolyl, 3-, 4-, or 5-isoxazolyl, 1,2,3-oxadiazol-4- or 5-yl, 1,2,4-oxadiazol-3- or 5-yl, 1,2,5- or 1,3,4-oxadiazolyl, 2-, 4-, or 5-thiazolyl, 3-, 4-, or 5-isothiazolyl, 1,2,3-thiadiazol-4- or 5-yl, 1,2,4-thiadiazol-3- or 5-yl, 1,2,5- or 1,3,4-thiadiazolyl, 2- or 3-pyrrolidinyl, 2-, 3-, or 4-pyridyl, 2-, 3-, or 4-pyridyl-N-oxido, 3-, or 4-pyridazinyl, 3- or 4-pyridazinyl-N-oxido, 2-, 4- or 5-pyrimidinyl, 2-, 4- or 5-pyrimidinyl-N-oxido, pyradinyl, 2-, 3-, or 4-piperidinyl, piperazinyl, 3H-indol.-2- or 3-yl, 2-, 3-, or 4-pyranyl, 2-, 3-, or 4-thiopyranyl, benzopyranyl, quinolyl, pyrido[2,3d]-pyrimidyl, 1,5-, 1,6-, 1,7-, 1,8-, 2,6-, or 2,7-naphthylidyl, thieno[2,3-d]pyridyl, pyrimidopyridyl, pyrazinoquinolyl, and benzopyranyl group.

A heterocyclic group in a " heterocyclic oxy", "heterocyclic thio", "heterocyclic amino", "heterocyclic carbonyl", "heterocyclic acetyl" and "heterocyclic carboxamide" group is preferably the "heterocyclic group" described above.

"A quaternary ammonium group" is formed when the unpaired electron on a tertiary nitrogen atom (a member of the nitrogen-containing heterocyclic ring described above) is used to form a bond, and this group is always accompanied by a corresponding anion. The quaternary ammonium group includes a oxazolium, thiazolium, isoxazolium, isothiazolium, pyridinium, and quinolinium group. The anion includes a hydroxide, halide (e.g. a chloride, bromide or iodide ion), sulfate, nitrate, carbonate, organic carboxylate (e.g. a oxalate or trifluoroacetate ion), and organic sulfonate ion (e.g. a p-toluenesulfonate ion). An organic carboxylate and organic sulfonate ion may be intramolecular.

The groups marked with * on the right shoulder are "the groups which may be substituted". For example, an alkyl* group means "an alkyl group which may be substituted". The number of the substituents is not necessarily limited to one, but may be 2 to several, preferably 2 or 3, according to the species of substituent, which may be the same or different.

A "$C_{6-10}aryl*$", a "$C_{7-12}aralkyl*$", a "$C_{6-10}aryl*oxy$", and a "$C_{7-19}aralkyl*oxy$" groups are preferably a "phenyl*", a "benzyl*", a "phenoxy*", and a "benzyl-*oxy", respectively.

In the compound [I] of this invention the substituent $R^0$ represents a hydrogen atom, a nitrogen-containing heterocyclic group, an acyl group, or an amino protective group. Among such compounds, compounds [I] wherein the substituent $R^0$ is a nitrogen-containing heterocyclic group or compounds [I] wherein $R^0$ is an acyl group are antibacterial compounds which have highly potent antibacterial activities against various bacteria, especially against cephalosporin-resistant bacteria, and also have a unique antibacterial activity against Pseudomonas sp. On the other hand, compounds [I] wherein the substituent $R^0$ is a hydrogen atom or compounds [I] wherein $R^0$ is a protected amino group are useful compounds which may be used as intermediates in the production of the compounds [I] described above wherein the substituent $R^0$ is a nitrogen-containing heterocyclic group or an acyl group.

The nitrogen-containing heterocyclic group as the substituent $R^0$ (hereinafter, sometimes represented by $R^a$) is the "nitrogen-containing heterocyclic group" described above, such as a 2-pyrrolyl, 3-pyrrolyl, 3-pyrazolyl, 4-pyrazolyl, 5-pyrazolyl, 2-imidazolyl, 4-imidazolyl, 5-imidazolyl, 1,2,3-triazolyl, 1,2,4-triazolyl, 1H-tetrazolyl, 2H-tetrazolyl, 2-oxazolyl, 4-oxazolyl, 5-oxazolyl, 3-isoxazolyl, 4-isoxazolyl, 5-isoxazolyl, 1,2,3-oxadiazol-4-yl, 1,2,3-oxadiazol-5-yl, 1,2,4-oxadiazol-3-yl, 1,2,4-oxadiazol-5-yl, 1,2,5-oxadiazolyl, 1,3,4oxadiazolyl, 2-thiazolyl, 4-thiazolyl, 5-thiazolyl, 3-isothiazolyl, 4-isothiazolyl, 5-isothiazolyl, 1,2,3-thiadiazol-4-yl, 1,2,3-thiadiazol-5-yl, 1,2,4-thiadiazol-3-yl, 1,2,4-thiadiazol-5-yl, 1,2,5-thiadiazolyl, 1,3,4-thiadiazolyl, 2-pyrrolidinyl, 3-pyrrolidinyl, 2-pyridyl, 3-pyridyl, 4-pyridyl, 2-pyridyl-N-oxido, 3-pyridyl-N-oxido, 4-pyridyl-N-oxido, 3-pyridazinyl, 4-pyridazinyl, 3-pyridazinyl-N-oxido, 4-pyridazinyl-N-oxido, 2-pyrimidinyl, 4-pyrimidinyl, 5-pyrimidinyl, 2-pyrimidinyl-N-oxido, 4-pyrimidinyl-N-oxido, 5-pyrimidinyl-N-oxido, pyrazinyl, 2-piperidinyl, 3-piperidinyl, 4-piperidinyl, piperadinyl, 3H-indol-2-yl, or 3H-indol-3-yl group. Among them, a 2-pyridyl, 3-pyridyl, 4-pyridyl, 2-imidazolyl, 4-imidazolyl, or 5-imidazolyl group is particularly preferable.

The nitrogen-containing heterocyclic groups may be substituted on the ring. The number of such substituents is not limited to one, but, according to the kinds of the substituent, 2 to several, preferably 2 or substituents, which may be the same or different, may be present. Such a substituent on the nitrogen-containing heterocyclic ring includes an alkyl, cycloalkyl, aryl, aralkyl, hydroxyl, alkoxy, mercapto, alkylthio, amino, monoalkylamino, dialkylamino, halogen atom, nitro, azido, cyano, carboxyl, alkoxycarbonyl, alkanoyl, alkanoyloxy, carbamoyl, monoalkylcarbamoyl, dialkylcarbamoyl, carbamoyloxy, monoalkylcarbamoyloxy, and dialkylcarbamoyloxy group.

As for the nitrogen-containing heterocyclic groups having substituents on the ring, a 2-imidazolyl group having the substituents such as an alkyl, aryl group, or a halogen atom, etc. as described above, or a N-substituted pyridinium-4-yl group which is derived from a 4-pyridyl group by substitution at the nitrogen atom with an alkyl or aralkyl group or the like described above and thereby the nitrogen atom itself is quaternized is preferable. Such a substituted-2-imidazolyl group includes a 1-methyl-2-imidazolyl, and 4-chloro-2-imidazolyl, and such a N-substituted pyridinium-4-yl group includes a N-methylpyridinium-4-yl, N-ethylpyridinium-4-yl, N-benzylpyridinium-4-yl, and N-(p-fluorobenzyl)pyridinium-4-yl group.

The acyl groups as the substituent $R^0$ (hereinafter, sometimes represented by $R^b$) mean the acyl groups substituting the amino group at the 6 position in the known penicillin derivatives and the acyl groups substituting the amino group at the 7 position in the known cephalosporin derivatives. Such an acyl group is derived from a carboxylic acid and includes an alkanoyl, alkenoyl, cycloalkylcarbonyl, cycloalkenylcarbonyl, arylcarbonyl, and heterocyclic carbonyl group, and more concretely, a $C_{1-6}alkanoyl*$, $C_{3-5}alkenoyl*$, $C_{3-10}cycloalkyl-carbonyl$, $C_{5-6}cycloalkenylcarbonyl$, $C_{6-10}aryl*carbonyl$, and $heterocyclic*carbonyl$ group.

The $C_{1-6}alkanoyl$ group includes, for example, a formyl, acetyl, propionyl, butyryl, isobutyryl, valeryl, isovaleryl, and pivaloyl group.

The substituents in a "$C_{1-6}alkanoyl$ group which may be substituted" represented by a $C_{1-6}alkanoyl*$ group include ①'a heterocyclic* group for $C_1$ alkanoyl group (i.e. formyl), and ② a "substituent $S^1$" described below for a $C_{2-6}alkanoyl$ group The "substituent $S^1$" is a $C_{3-10}cycloalkyl*$, $C_{5-6}cycloalkenyl*$, $C_{6-10}aryl*$, hydroxyl, $C_{1-6}alkoxy$, $C_{3-10}cycloalkyloxy$, $C_{6-10}aryl*oxy$, $C_{7-19}aralkyl*oxy$, mercapto, $C_{1-6}alkyl*thio$, amino $C_{1-}$ 6alkylthio, C$_{2-6}$alkenyl*thio, C$_{3-10}$cycloalkylthio, C$_{6-10}$aryl*thio, C$_{7-19}$aralkyl*thio, amino, monoC$_{1-6}$alkylamino, diC$_{1-6}$alkylamino, C$_{3-10}$cycloalkylamino, C$_{6-10}$aryl*amino, C$_{7-19}$aralkyl*amino, cyclic amino*, halogen atom, nitro, azido, cyano, carboxyl, acyl+, substituted oxycarbonyl, C$_{1-6}$alkylthiocarbonyl, acyl+oxy, acyl+amino, acyl+aminoalkylthio, carbamoyl, monoC$_{1-6}$alkylcarbamoyl, diC$_{1-6}$alkylcarbamoyl, carbamoyloxy, monoC$_{1-6}$alkylcarbamoyloxy, diC$_{1-6}$alkylcarbamoyloxy, sulfo, hydroxysulfonyloxy, C$_{1-6}$alkylsulfonyl, C$_{6-10}$aryl*sulfonyl, C$_{7-19}$aralkyl*sulfonyl, C$_{1-6}$alkylsulfonyloxy, C$_{6-10}$aryl*sulfonyloxy, C$_{7-19}$aralkyl*sulfonyloxy, ureido*, sulfamoyl*, heterocyclic*, heterocyclic*oxy, heterocyclic*thio, heterocyclic*amino, heterocyclic*carbonyl, heterocyclic*carboxamido, or quaternary ammonium* group. The number of these substituents is not restricted to one, preferably one to three and in case there are two to three substituents, these substituents may be the same or different. Further, two of the substituents may form a C=C bond or a C=N bond described later.

The substituents in a "C$_{3-5}$alkenoyl group which may be substituted" represented by a C$_{3-5}$alkenoyl* group (hereinafter represented by "subsituent S$^2$") include, for example, a C$_{3-10}$cycloalkyl, C$_{6-10}$aryl*, C$_{1-6}$alkoxy, C$_{6-10}$aryloxy, C$_{7-19}$aralkyl*oxy, halogen atom, cyano, carboxyl, acyl+, substituted oxycarbonyl, acyl+oxy, heterocyclic*, and quaternary ammonium* group.

The substituents in a "C$_{6-10}$arylcarbonyl group which may be substituted" represented by a C$_{6-10}$aryl*carbonyl group and the substituents in a "heterocyclic group which may be substituted" represented by a heterocyclic*carbonyl group (both substituents are represented by "substituent S$^3$" hereinafter) include a C$_{1-6}$alkyl, C$_{2-6}$alkenyl, C$_{6-10}$aryl, C$_{7-12}$aralkyl, diC$_{6-10}$arylmethyl, triC$_{6-10}$arylmethyl, hydroxyl, C$_{1-6}$alkoxy, C$_{6-10}$aryloxy, C$_{7-19}$aralkyloxy, mercapto, C$_{1-6}$alkylthio, C$_{6-10}$arylthio, C$_{7-19}$aralkylthio, amino, monoC$_{1-6}$alkylamino, diC$_{1-6}$alkylamino, hydroxy C$_{1-6}$alkyl, mercapto C$_{1-6}$alkyl, halogeno C$_{1-6}$alkyl, carboxy C$_{1-6}$alkyl, halogen atom, nitro, azido, cyano, carboxyl, substituted oxycarbonyl, acyl+, acyl+oxy, acyl+amino, carbamoyl, thiocarbamoyl, C$_{1-6}$alkylsulfonyl, C$_{6-10}$arylsulfonyl, and C$_{7-19}$aralkylsulfonyl group.

To the substituents described above (S$^1$, S$^2$ and S$^3$) for C$_{1-6}$alkanoyl group, C$_{3-5}$alkenoyl group, C$_{6-10}$arylcarbonyl group and heterocyclic carbonyl group, except the groups described below, the same definitions as described before are also applicable.

The substituent S$^3$ described above is also applicable as the substituent of the C$_{6-10}$aryl group in a C$_{6-10}$aryl*, phenyl*, C$_{6-10}$aryl*oxy, phenoxy*, C$_{6-10}$aryl*thio, C$_{6-10}$aryl*amino, C$_{6-10}$aryl*sulfonyl and C$_{6-10}$aryl*sulfonyloxy group.

The substituent S$^3$ described above is also applicable as the substituent of the aromatic ring of C$_{7-12}$ or C$_{7-19}$aralkyl group in a C$_{7-12}$aralkyl*, benzyl*, C$_{7-19}$aralkyl*oxy, benzyl*oxy, C$_{7-19}$aralkyl*thio, C$_{7-19}$aralkyl*amino, C$_{7-19}$aralkyl*sulfonyl and C$_{7-19}$aralkyl*sulfonyloxyl group.

The substituent S$^3$ described above is also applicable as the substituent of the heterocyclic group in a heterocyclic*, heterocyclic*oxy, heterocyclic*thio, heterocyclic*amino, heterocyclic*acetyl and heterocyclic*amino, cyclic*carboxamido group.

The substituent S$^3$ described above is also applicable as the substituent of the nitrogen-containing heterocyclic ring in a quaternary ammonium* group.

The substituent S$^1$ described above is also applicable as the substituent of the C$_{1-6}$alkyl group in a "C$_{1-6}$alkyl group which may be substituted" represented by a C$_{1-6}$alkyl* group.

The substituent S$^3$ described above is also applicable as the substituent of the "C$_{3-10}$cycloalkyl group which may be substituted" and "C$_{5-6}$cycloalkenyl group which may be substituted" represented, respectively, by a C$_{3-10}$cycloalkyl* group and C$_{5-6}$cycloalkenyl* group.

The substituents of the C$_{1-6}$alkylthio group in a "C$_{1-6}$alkylthio group which may be substituted" represented by a C$_{1-6}$alkyl*thio group (hereinafter represented by "substituent S$^4$") include a hydroxyl, C$_{1-6}$alkoxy, C$_{3-10}$cycloalkyloxy, C$_{6-10}$aryl*oxy, C$_{7-19}$aralkyl*oxy, mercapto, C$_{1-6}$alkylthio, C$_{3-10}$cycloalkylthio, C$_{6-10}$aryl*thio, C$_{7-19}$aralkyl*thio, amino, monoC$_{1-6}$alkylamino, diC$_{1-6}$alkylamino, cyclic amino*, halogen atom, cyano, carboxyl, carbamoyl, acyl+oxy, sulfo, and quaternary ammonium* group.

The substituents of the C$_{2-6}$alkenylthio group in a "C$_{2-6}$alkenylthio group which may be substituted" represented by a C$_{2-6}$alkenyl*thio group (hereinafter represented by "substituent S$^5$") include a halogen atom, a cyano, carboxyl, cabamoyl, monoC$_{1-6}$alkylcarbamoyl, diC$_{1-6}$alkylcarbamoyl, and thiocarbamoyl.

The "acyl+ group" is a C$_{1-6}$alkanoyl, C$_{6-10}$aryl*carbonyl, C$_{7-19}$aralkyl*carbonyl, heterocyclic*carbonyl or heterocyclic*acetyl group. Therefore representative acyl+ are formyl, acetyl, propionyl, n-butyryl, isobutyryl, valeryl, pivaloyl, n-hexanoyl, chloroacetyl, dichloroacetyl, trichloroacetyl, 3-oxobutyryl, 4-chloro-3-oxobutyryl, 3-carboxypropionyl, 4-carboxybutyryl, 3-ethoxycarbamoylpropionyl, benzoyl, naphthoyl, p-methylbenzoyl, p-hydroxybenzoyl, p-methoxybenzoyl, p-chlorobenzoyl, p-nitrobenzoyl, o-carboxybenzoyl, o-(ethoxycarbonylcarbomoyl)benzoyl, o-(ethoxycarbonylsulfamoyl)benzoyl, phenylacetyl, p-methylphenylacetyl, p-hydroxyphenylacetyl, p-methoxyphenylacetyl, 2,2-diphenylacetyl, 2-thienylcarbonyl, 2-furylcarbonyl, 2-, 4- or 5-thiazolylacetyl, 2- or 3-thienylacetyl, 2- or 3-furylacetyl, 2-amino-4- or 5-thiazolylacetyl, and 5-amino-3-[1,2,4]thiadiazolylacetyl.

The acyl+group in an "acyl+oxy" and "acyl+amino" group means the acyl+ group described above, and therefore an "acyl+oxy group" includes a formyloxy, acetoxy, propionyloxy, butyryloxy, valeryloxy, pivaloyloxy, chloroacetoxy, dichloroacetoxy, trichloroacetoxy, 3-oxobutyryloxy, 4-chloro-3-oxobutyryloxy, 3-carboxypropionyloxy, 4-carboxybutyryloxy, 3-ethoxycarbamoylpropionyloxy, benzoyloxy, naphthoyloxy, p-methylbenzoyloxy, p-methoxybenzoyloxy, p-chlorobenzoyloxy, o-carboxybenzoyloxy, o-(ethoxycarbonylcarbamoyl)benzoyloxy, o-(ethoxycarbonylsulfamoyl)benzoyloxy, phenylacetyloxy, p-methylphenylacetyloxy, p-methoxyphenylacetyloxy, p-chlorophenylacetyloxy, 2,2-diphenylacetyloxy, thienylcarbonyloxy, furylcarbonyloxy, thiazolylacetyloxy, thienylacetyloxy, and furylacetyloxy group; an "acyl+aminio group" includes an acetamid (CH$_3$CONH—), benzamido (C$_6$H$_5$CONH—), phenylacetamido (C$_6$H$_5$CH$_2$CONH—), and 2-thienylacetamido

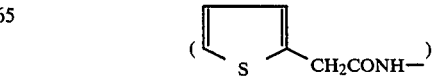

group.

The acyl+amino and alkylthio groups in an "acyl-+aminoalkylthio group" mean respectively the acyl-+amino group and the $C_{1-6}$alkylthio group described before, and therefore such a "acyl30aminoC$_{1-6}$alkylthio group" includes an acetamidomethylthio, and 2-acetamidoethylthio group.

The "arylacyl+group" is preferably a "$C_{6-10}$arylacyl+ group" such as a benzoyl, phthaloyl, naphthoyl, and phenylacetyl group.

The "arylacyl+oxy group" is preferably a "$C_{6-10}$arylacyl+oxy group" such as a benzoyloxy, naphthoyloxy, add phenylacetyloxy group.

The substituents of the ureido group in an "ureido group which may be substituted" represented by an "ureido* group" include a $C_{1-6}$alkyl, $C_{6-10}$aryl*, $C_{7-19}$aralkyl*, acyl+, carbamoyl, sulfo (which may form a salt with sodium or potassium), sulfamoyl and amidino group.

The substituents of the sulfamoyl group in a "sulfamoyl group which may be substitued" represented by an "sulfamoyl* group" include a $C_{1-6}$alkyl and amidino group.

The substituents of the "carbamoyl group which may be substituted" represented by a "carbamoyl*" and "carbamoyl*oxy" group include a $C_{1-6}$alkyl, $C_{6-10}$aryl*, $C_{7-12}$aralkyl*, and acyl+ group, including the case where the carbamoyl nitrogen atom is the ring constituting nitrogen atom of the nitrogen-containing heterocyclic ring.

The substituents of the "thiocarbamoyl group which may be substituted" represented by a "thiocarbamoyl* group" include a $C_{1-6}$alkyl, $C_{6-10}$aryl*, $C_{7-12}$aralkyl*, and acyl+ group, including the case where the thiocarbamoyl nitrogen atom is the ring constituting nitrogen atom of the nitrogen-containing heterocyclic ring.

The substituents of the cyclic amino group in a "cyclic amino group which may be substituted" represented by a"cyclic amino* group" (hereinafter represented by "substituent $S^6$") include a $C_{1-6}$alkyl, $C_{2-6}$alkenyl, $C_{3-10}$cycloalkyl, $C_{6-10}$aryl*, $C_{7-12}$aralkyl*, diC$_{6-10}$arylmethyl, triC$_{6-10}$aryl-methyl, hydroxyl, $C_{1-6}$alkoxy, $C_{6-10}$aryl*oxy, $C_{7-19}$aralkyl*oxy, mercapto, $C_{1-6}$alkylthio, $C_{6-10}$aryl*thio, $C_{7-19}$aralkyl*thio, amino, monoC$_{1-6}$alkylamino, diC$_{1-6}$alkylamino, $C_{6-10}$aryl*amino, $C_{7-19}$aralkyl*amino, halogen atom, nitro, azido, oxo, thioxo, cyano, carboxyl, acyl*, substituted oxycarbonyl, acyl-+oxy, acyl+amino, carbamoyl, carbamoyloxy, thiocarbamoyl, and sulfo group.

The formyl group substituted with heterocyclic*carbonyl group described above as a $C_{1-6}$alkanoyl* group is an acyl group having the formula of heterocyclic ring*-CO-CO-wherein the heterocyclic* group described above is also applicable here, oxazolyl group, thiazolyl group, oxadiazolyl group and thiadiazolyl group which may be substitued being more desirable. Such a "heterocyclic*-CO-CO-" group includes a 2-(2-, 4- or 5-oxazolyl)-2-oxoacetyl, 2-(2-, 4- or 5-thiazolyl)-2-oxoacetyl, 2-(2-amino-4-thiazolyl)-2-oxoacetyl, 2-(1,2,4-oxadiazol-3- or 5-yl)-2-oxoacetyl, and 2-(5-amino-1,2,4-thiadiazol-3-yl)-2-oxoacetyl group.

A substituted acetyl group is the most desirable as $C_{2-6}$alkanoyl* group. One to 3 substituents may be present in the substituted acetyl group, and the "substituent $S^1$" described above for the substituents of the $C_{1-6}$alkanoyl group is also applicable here. When 2 or 3 substituents are present, the substituents may be the same or different, and two of them may join to form a double bond. The mono-substituted acetyl group is represented by $R^{15}CH_2CO—$, and disubstituted acetyl is represented by

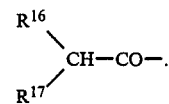

Trisubstituted acetyl groups are preferably those where two of the substituents combinedly form a C=C double bond or a C=N double bond, which are represented respectively by

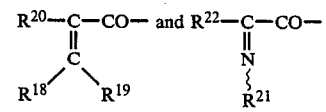

wherein, symbols $R^{15}$, $R^{16}$, $R^{17}$, $R^{20}$ and $R^{22}$ mean the substituent ($S^1$) described above, and the symbols $R^{18}$, $R^{19}$ and $R^{21}$ are described below. In the following the acetyl group having these substituents ($R^{15}$, $R^{16}$, $R^{17}$, $R^{18}$, $R^{19}$, $R^{20}$, $R^{21}$, $R^{22}$) is described in detail.

(i) $R^{15}CH_2CO—$

The symbol $R^5$ means the substituents ($S^1$) of the $C_{1-6}$alkyl group described above, among which a $C_{5-6}$cycloalkenyl group, $C_{6-10}$aryl*, $C_{6-10}$aryl*oxy, $C_{1-6}$alkyl*thio, $C_{2-6}$alkenyl*thio, $C_{6-10}$aryl*thio, amino, cyclic amino, cyano, acyl+, acyl+oxy, heterocylic*, heterocyclic*thio, or quaternary ammonium* group is frequently used. Therefore, the "acyl group $R^{15}CH_2CO—$" includes a 1,4-cyclohexadienylacetyl, phenylacetyl, p-tolylacetyl, p-hydroxyphenylacetyl, p-methoxyphenylacetyl, p-chlorophenylacetyl, o-aminomethylphenylacetyl, phenoxyacetyl, p-hydroxyphenoxyacetyl, p-chlorophenoxyacetyl, cyanomethylthioacetyl, difluoromethylthioacetyl, trifluoromethylthioacetyl, (2-carboxyethyl)thioacetyl, (2-amino-2-carboxyethyl)thioacetyl, (2-chlorovinyl)thioacetyl, (2-carboxyvinyl)thioacetyl, (2-fluoro-2-carbamoylvinyl)thioacetyl, (1,2-dichlorovinyl)thioacetyl, (2-chloro-2-carboxyvinyl)thioacetyl, phenylthioacetyl, p-hydroxyphenylthioacetyl, glycyl, (1H-tetrazoly-1-yl)acetyl, (3,5-dichloro-4-oxo-1,4-dihydropyridin-1-yl)acetyl, cyanoacetyl, acetoacetyl, benzoylacetyl, furylcarbonylacetyl, thienylcarbonylacetyl, (1H-tetrazolyl)acetyl, (1-methyl-1H-tetrazoly)acetyl, (2-furyl)acetyl, (2-thienyl)acetyl, (3-thienyl)acetyl, (4-oxazolyl)acetyl, acetyl, (4-thiazolyl)acetyl, (2-amino-4-thiazolyl)acetyl, (1,2,4-thiadiazol-3-yl)acetyl, (5-amino-1,2,4-thiadiazol-3-yl)acetyl, (2-pyridyl)acetyl, (4-pyridyl)acetyl, (2-imidazolyl)thioacetyl, (2-pyridyl)thioacetyl, (4-pyridyl)thioacetyl, (2-thienyl)thioacetyl, hydroxypyridylthioacetyl, (5-isothiazolyl)thioacetyl, (3-methylthio-isothiazolyl)thioacetyl, (4-cyano-5-isothiazolyl)thioacetyl, (4-cyano-2-methyl-3-oxo-2,3-dihydroisothiazol-5-yl)thioacetyl, pyridiniumacetyl, and quinoliniumacetyl group.

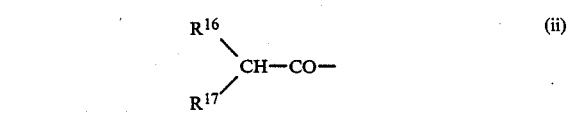

(ii)

The symbol $R^{16}$ means the substituents ($S^1$) described above, among which a $C_{5-6}$cycloalkenyl, $C_{6-10}$aryl, $C_{6-}$ 10aryl*oxy, $C_{1-6}$alkyl*thio, $C_{2-6}$alkenyl*thio, $C_{6-10}$aryl*thio, cyclic amino, cyano, heterocyclic*, heterocycle*thio, heterocycle*carboxamido, or quaternary ammonium* group is frequently used. The symbol $R^{17}$ means the substituents described above ($S^1$), among which a hydroxyl, mercapto, amino, amino group substituted with amino acid residue, hydrazino, azido, ureido*, acyl+oxy, acyl+amino, carboxyl, substituted oxycarbonyl, sulfo, sulfamoyl, carbamoyl, or heterocyclic*carboxamido group is preferable. Among these substituents, those having an amino group as the substituent $R^{17}$

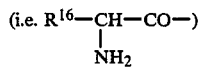

(i.e. $R^{16}$—CH—CO—)
          |
          $NH_2$ are sometimes especially classified as the "amino acid residues". Therefore the

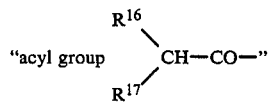

"acyl group $\begin{matrix}R^{16}\\ \diagdown \\ \diagup \\ R^{17}\end{matrix}$ CH—CO—"

includes a 2-amino-2-(1,4-cyclohexadienyl)acetyl, mandelyl, α-azidophenylacetyl, α-carboxyphenylacetyl, α-(phenoxycarbonyl)phenylacetyl, α-(o-hydroxyphenyl)oxycarbonylphenylacetyl, α-(p-tolyloxycarbonyl)phenylacetyl, α-sulfophenylacetyl, α-sufo-p-hydroxyphenylacetyl, α-ureidophenylacetyl, α-(Nγ-sulfoureido)phenylacetyl, α-carboxy-p-hydroxyphenylacetyl, α-(formyloxy)phenylacetyl, α-(2-amino-3-carboxypropionamido)phenylacetyl, α-(3-amino-3-carboxypropionamido)phenylacetyl, α-(3,4-dihydoxybenzamido)phenylacetyl, α-(5-carboxy-4-imidazolyl-carboxamide)phenylacetyl, α-(1,3-dimethyl-4-pyrazolylcarboxamide)phenylacetyl, 5-phenyl-3-isoxazolyl-carboxamido)phenylacetyl, α-[[1-(p-methoxyphenyl)-4-chloro-1,2,3-triazol-5-yl]carboxamido]phenylacetyl, α-[(4-oxo-1,4-dihydropyridine-3-yl)carboxamido]-phenylacetyl, α-[[2-oxo-5(3,4-dihydroxyphenyl)-1,2-dihydropyridine-3-yl]carboxamido]phenylacetyl, α-[(4-oxo-4H-1-thiopyran-3-yl)carboxamido]phenylacetyl, α[(4-hydroxy-1,5-naphthylidin-3-yl)carboxamido)]-phenylacetyl, α-(4-ethyl-2,3-dioxopiperadinocarboxamido)phenylacetyl, α-(4-ethyl-2,3-dioxopiperadinocarboxamido)-p-hydroxyphenylacethyl, α-(4-ethyl-2,3-dioxopiperadinocarboxamido)-p-benzyloxyphenylacetyl, α-(4-ethyl-2,3-dioxopiperadinocarboxamido)-p-sulfophenylacetyl α-(4-ethyl-2,3-dioxopiperazinocarboxamido)p-methoxyphenylacetyl, α-(2-oxoimidazolidinocarboxamido)phenylacetyl, α-(2-oxo-3-methanesulfonylimidazolidinocarboxamido)phenylacetyl, α-[(6,7-dihydroxy-4-oxo-4H-benzopyran-3-yl)carboxamido)]phenylacetyl, α-[(6,7-dihydroxy-2-oxo-2H-benzopyran-3-yl)carboxamido)]phenylacetyl, α-hydroxy-2-thienylacetyl, α-hydroxy-3-thienylacetyl, α-carboxy-3-thienylacetyl, α-amino-o-(2-aminothiazol-4-yl)acetyl, α-formamido-α-(2-aminothiazol-4-ylacetyl, α-acetamido-α-(2-aminothiazol-4-yl)acetyl, α-formanido-α-(2-amino-5-chlorothiazol-4-yl)acetyl, α-acetamido-α-(2-amino-5-chlorothiazol-4-yl)acetyl, α-formamido-α-(5-amino-1,2,4-thiadiazol-3-yl)acetyl, α-acetamido-α-(5-amino-1,2,4-thiadiazol-3-yl)acetyl, α-hydrazino-α-(2-aminothiazol-4-yl)acetyl, α-hydroxy-α-(2-aminothiazol-4-yl)acetyl, α-ureido-α-(2-aminothiazol-4-yl)acetyl, α-[Nγ-(m-hydroxyphenyl)ureido]-phenylacetyl, α-[Nγ-(2-methyl-6-hydroxypyrimidin-5-yl)ureido]phenylacetyl, α-[Nγ-(3,4-diacetoxybenzoyl)ureido]phenylacetyl, α-[Nγ-(3.4-dihydroxycinnamoyl)ureido]phenylacetyl, α-[Nγ(3,4-diacetoxybenzamidoacetyl)ureido]phenylacetyl, α-[Nγ(2-furylcarbonyl)ureido]phenylacetyl, α-[Nγ-[(6,7-dihydro-4-oxo-4H-benzopyran-3-yl)carbonyl)]ureido]phenylacetyl, α-(2-chlorovinylthio)phenylacetyl, α-carbamoyl-α-(2-chlorovinylthio)acetyl, α-(4-ethyl-2,3-dioxopiperazinocarboxamido)-α-(2-chlorovinylthio)-acetyl, α,α-bis-(4-ethyl-2,3-dioxo-1-piperazinocarboxamido)acetyl, α-(2-amino-4-thiazolyl)-α-(4-ethyl-2,3-dioxo-1-piperazinocarboxamido)acetyl, α-(4-hydroxy-6-methyl-nicotinamido)-α-phenylacetyl, α-(4-hydroxy-6-methyl-nicotinamido)-α-(4-hydroxyphenyl)acetyl, α-{5,8-dihydro-2-(4-formyl-1-piperazinyl)-5-oxopyrido[2,3-d]pyrimidin-6-carboxamido}-α-phenylacetyl, α-(3,5-dioxo-1,2,4-triazine-6-carboxamido)-α-(4-hydroxyphenyl)acetyl, α-(3-furfurylidenamino-2-oxoimidazolidine-1-carboxamido)-α-phenylacetyl, α-(coumarin-3-carboxamido)-α-phenylacetyl, α-(4-hydroxy-7-methyl-1,8-naphthylidine-3-carboxamdio)-α-phenylacetyl, α-(4-hydroxy-7-trifluoromethylquinoline-3-carboxamido)-α-phenylacetyl, N[2-(2-amino-4-thiazolyl-)acetyl]-D-phenylglycyl, α-(6-bromo-1-ethyl-1,4-dihydro-4-oxothieno[2,3-b]pyridine-3-carboxamido)-α-phenylacetyl, α-(4-ethyl-2,3-dioxo-1-piperadinocarboxamido)-α-thienylacetyl, α-(4-n-pentyl2,3-dioxo-1-piperadinocarboxamido)-α-thienylacetyl, α-(4-n-octyl-2,3-dioxo-1-piperdinocarboxamido)-α-thienylacetyl, α-(4-cyclohexyl-2,3-dioxo-1-piperadinocarboxamido)-α-thienylacetyl, α-[4-(2-phenylethyl)2,3-dioxo-1-piperadinocarboxamido]-α-thienylacetyl, and α-(3-furfurylideneamino-2-oxoimidazolidine-1-carboxamido)α(4-hydroxyphenyl)acetyl. The amino acid residue

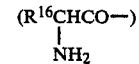

($R^{16}$CHCO—)
    |
   $NH_2$ includes also here an alanyl, valyl, leucyl, isoleucyl, seryl, threonyl, cysteinyl, cystyl, methionyl, asparagyl, glutamyl, lysyl, arginyl, phenylglycyl, phenylalanyl, tyrosyl, hystidyl, tryptophyl, and prolyl residue. The amino group in these amino acid residues may be protected with the amino protective group described below. The "amino acid residue wherein the amino group is protected" includes a N-benzyloxycarbonylalanyl, and N-benzyloxycarboxamidophenylglycyl residue. The amino group in the amino acid residue may be substituted with another amino acid residue. Such an acyl group is a "dipeptide residue", and such an acyl group includes a phenylglycyl-alanyl, benzyl Nα-benzyloxycarbonyl-γ-glutamyl-alanyl, alanylbenzyl phenylglycyl, γ-aspartyl-phenylglycyl, and γ-glutamylalanyl group. The amino group in the amino acid residue may be substitutd with a cyclic carbamoyl group. Such an acyl group includes a N-(4-ethyl-2,3-dioxo-1-piperadinocarbonyl)alanyl, N-(4-ethyl-2,3-dithioxo-1piperadinocarbonyl)phenylglycyl, and N-(4-ethyl-2,3-dioxo-1-piperadinocarbonyl)threonyl gorup.

As one of the acyl groups

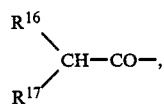

an acyl group represented by

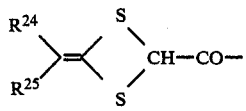

wherein $R^{24}$ and $R^{25}$ are, the same or different, a hydrogen or halogen atom (fluorine, chlorine, bromine, iodine), or a hydroxymethyl, difluoromethyl, trifluoromethyl, formyl, cyano, azido, carboxyl, carbamoyl, $C_{1\text{-}6}$alkylthio or $C_{6\text{-}10}$aryl*thio group, may be used. Such an acyl group includes

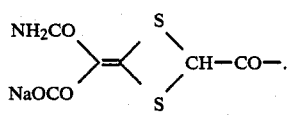

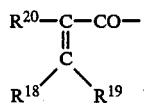 (iii)

The symbol $R^{20}$ means the substituents ($S^1$) described above, among which a $C_{6\text{-}19}$aryl*, $C_{6\text{-}10}$aryl*oxy, $C_{6\text{-}10}$aryl*thio, heterocyclic*, or heterocyclic*thio is frequently used. The symbol $R^{18}$ is a hydrogen atom or a halogen atom (fluorine, chlorine, bromine, iodine and preferably chlorine). The symbol $R^{19}$ means a $C_{1\text{-}6}$alkyl, $C_{6\text{-}10}$aryl*, $C_{1\text{-}6}$alkylthio, halogen atom, cyano, amino, $C_{1\text{-}6}$alkylsulfonyl, $C_{6\text{-}10}$aryl*sulfonyl, carbamoyl, $C_{1\text{-}6}$alkoxyimidoyl or heterocyclic* group. The $C_{1\text{-}6}$alkoxy group in the $C_{1\text{-}6}$alkoxyimidoyl group is preferably the $C_{1\text{-}6}$alkoxy group described above, and therefore such a $C_{1\text{-}6}$alkoxyimidoyl group includes a methoxyimidoyl

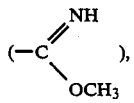

and ethoxyimidoyl group. As for the other groups which are not mentioned here, the groups described before are also applicable. Therefore, an "acyl group

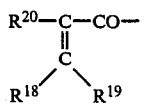

includes a 2-(2-amino-4-thiazolyl)-3-chloroacryloyl, 2-(2-amino-4-thiazolyl)crotonoyl, 2-(2-amino-4thiazolyl)cinnamoyl, 2-(2-amino-4-thiazolyl)-3-methanesulfonylacryloyl, 2-(2-amino-4-thiazolyl)-3-benzenesulfonylacryloyl, 2-(5-amino-1,2,4-thiadiazol-3-yl)-2-pentenoyl, 2-(5-amino-1,2,4-thiadiazol-3-yl)-3-chloroacryloyl, 2-(5-amino-1,2,4-thiadiazol-3-yl-croton-oyl, 2-(2-amino-5-chloro-4-thiazolyl)-3-chloroacryloyl, and 2-(2-amino-5-chloro-4-thiazolyl)crotonoyl.

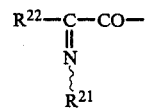 (iv)

The symbol $R^{22}$ means the substituents ($S^1$) described above, among which a $C_{3\text{-}10}$cycloalkyl*, $C_{5\text{-}6}$cycloalkenyl*, $C_{6\text{-}10}$aryl*, $C_{1\text{-}6}$alkoxy, $C_{6\text{-}10}$aryl*oxy, $C_{1\text{-}6}$alkyl*thio, amino$C_{1\text{-}6}$alkylthio, $C_{6\text{-}10}$aryl*thio, $C_{7\text{-}19}$aralkyl*thio, cyano, acyl+, carbamoyl or heterocyclic* group is frequently used.

Among these, a $C_{6\text{-}10}$aryl* group and a heterocyclic* group are, especially preferable. Substituents for these $C_{6\text{-}10}$aryl and heterocyclic groups are preferably a $C_{1\text{-}6}$alkyl, hydroxyl, amino group, and halogen atom (fluorine, chlorine, bromine, or iodine). Therefore, the preferable group as the substituent $R^{22}$ includes a phenyl, p-hydroxyphenyl, 2-furyl, 2-thienyl, 4-oxazolyl, 2-amino-4-oxazolyl, 2-amino-5-chloro-4-oxazolyl, 4-thiazolyl, 2-amino-4-thiazolyl, 2-amino-5-chloro-4-thiazolyl, 2-amino-5-bromo-4-thiazolyl, 2-amino-5-fluoro-4-thiazolyl, 2-amino-4-thiazolyl-3-oxido, 2-imino-3-hydroxythiazoline-4-yl, 3-isoxazolyl, 5-amino-3-isoxazolyl, 3-isothiazolyl, 5-amino-3-isothiazolyl, 1,2,4-oxadiazol-3-yl, 5-amino-1,2,4-oxadiazol-3-yl, 1,2,4-thiadiazol-3-yl, 5-amino-1,2,4-thiadiazol-3-yl, 1,3,4-oxadiazolyl, 2-amino-1,3,4-oxadiazol-5-yl, 1,3,4-thiadiazolyl, 2-amino-1,3,4-thiadiazol-5-yl, 1-($C_{1\text{-}6}$alkyl)-5-amino-1,2,4-triazol-3-yl, 4-($C_{1\text{-}6}$alkyl)-5-amino-1,2,4-triazol-3-yl, 1-($C_{1\text{-}6}$alkyl)-2-amino-4-imidazolyl, 2-amino-6-pyridyl, 4-amino-2-pyrimidyl, 2-amino-5-pyrimidyl, 3-pyrazolyl, and 4-pyrazolyl group. The symbol $R^{21}$ is a $OR^{23}$ group wherein $R^{23}$ is a hydrogen atom or a hydrocarbon residue which may be substituted. The group represented by

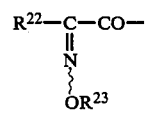

is a syn isomer represented by

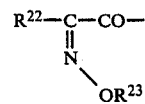

or an anti isomer represented by

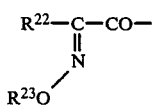

or a mixture thereof, among which a syn isomer having a heterocyclic* group as the substituent $R^{22}$ is desirable. Such an acyl group is represented by the formula

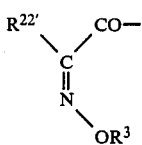

wherein $R^{22'}$ is a heterocyclic* group and $R^3$ is a hydrogen atom or a hydrocarbon residue which may be substituted. The heterocyclic* group $R^{22}$ is most preferably a substituted thiazolyl or thiadiazolyl group, i.e. a group represented by the formula

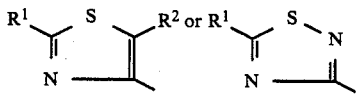

wherein $R^1$ is an amino group which may be protected, and $R^2$ is a hydrogen atom, a halogen atom or a nitro group. Therefore the most desirable $R^b$ group is the group represented by the formula

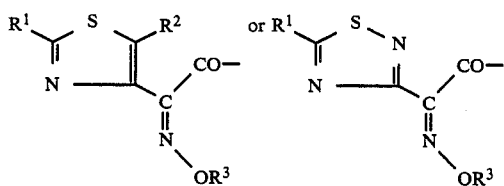

syn isomer (Z configuration) syn isomer (Z configuration) That is, among the compounds [I] having an acyl group $R^b$ as the substituent $R^0$, a compound having the structure

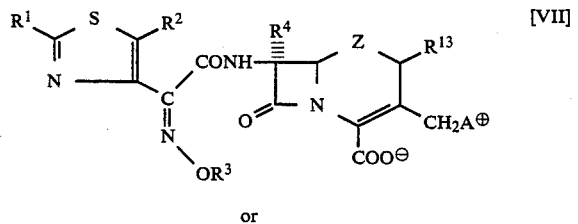

or

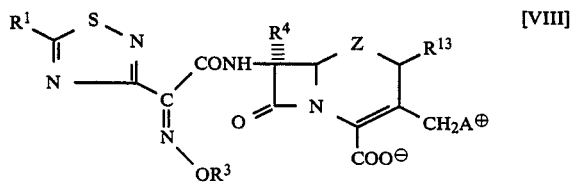

wherein the symbols are the same as described above, is desirable. In the following, the substituents $R^1$, $R^2$ and $R^3$ are described in detail.

The symbol $R^1$ means an amino group which may be protected. In the field of β-lactams and peptides, amino protective groups have been studied extensively and the methods for amino-protection have already been established: such prior art methods are applicable also to the protection of the amino group in this invention. Such an amino protective group includes a $C_{1-6}$alkanoyl*, $C_{3-5}$alkenoyl*, $C_{6-10}$aryl*carbonyl, phthaloyl, heterocyclic*carbonyl, $C_{1-6}$alkyl*sulfonyl, camphorsulfonyl, $C_{6-10}$aryl*sulfonyl, substituted oxycarbonyl, carbamoyl*, thiocarbamoyl*, $C_{6-10}$aryl*methyl, di$C_{6-10}$aryl*methyl, tri$C_{6-1}$aryl*methyl, $C_{6-10}$aryl*methylene, $C_{6-10}$aryl*thio, substituted silyl, and 2-$C_{1-10}$alkoxy-carbonyl-1-methyl-1-ethenyl group The "$C_{1-6}$alkanoyl* group" includes a formyl, acetyl, propionyl, butyryl, valeryl, pivaloyl, succinyl, glutaryl, monochloroacetyl, dichloroacetyl, trichloroacetyl, monobromoacetyl, monofluoroacetyl, difluoroacetyl, trifluoroacetyl, monoiodoacetyl, 3-oxobutyryl, 4-chloro-3-oxo-butyryl, phenylacetyl, p-chlorophenylacetyl, phenoxyacetyl, and p-chlorophenoxyacetyl group.

The "$C_{3-5}$alkenoyl* group" includes an acryloyl, crotonoyl, maleoyl, cinnamoyl, p-chlorocinnamoyl, and β-phenylcinnamoyl group.

The "$C_{6-10}$ aryl*carbonyl group" includes a benzoyl, naphthoyl, p-toluoyl, p-tert-butylbenzoyl, p-hydroxybenzoyl, p-methoxybenzoyl p-tert-butoxybenzoyl, p-chlorobenzoyl, and p-nitrobenzoyl group.

The heterocyclic* carbonyl group includes each of the groups descirbed below.

The "$C_{1-6}$alkyl*sulfonyl group" includes a methanesulfonyl and ethanesulfonyl group.

The "$C_{6-10}$aryl*sulfonyl group" includes a benzenesulfonyl, naphthalenesulfonyl, p-toluenesulfonyl, p-tert-butyl-benzenesulfonyl, p-methoxybenzenesulfonyl, p-chlorobenzenesulfonyl, and p-nitrobenzenesulfonyl group.

The "substituted oxycarbonyl group" includes, in addition to the substituted oxycarbonyl group described above i.e. a $C_{1-10}$alkoxy-carbonyl, $C_{6-10}$aryloxycarbonyl or $C_{7-19}$aralkyloxy-carbonyl group, also the one having substituents(s), such as a methoxycarbonyl, ethoxycarbonyl, n-propoxycarbonyl, isopropoxycarbonyl, n-butoxycarbonyl, tert-butoxycarbonyl, cyclohexyloxycarbonyl, norbornyloxycarbonyl, phenoxycarbonyl, naphthyloxycarbonyl, benzyloxycarbonyl, methoxymethyloxycarbonyl, acetylmethyloxycarbonyl, 2-trimethylsilylethoxycarbonyl, 2-methanesulfonylethoxycarbonyl, 2,2,2-trichloroethoxycarbonyl, 2-cyanoethoxycarbonyl, p-methylphenoxycarbonyl, p-methoxyphenoxycarbonyl, p-chloropheoxycarbonyl, p-methylbenzyloxycarbonyl, p-methoxybenzyloxycarbonyl, p-chlorobenzyloxycarbonyl, p-nitrobenzyloxycarbonyl, benzhydryloxycarbonyl, cyclopropyloxycarbonyl, cyclopentyloxycarbonyl, and cyclohexyloxycarbonyl group.

The "carbamoyl* group" includes carbamoyl, N-methylcarbamoyl, N-ethylcarbamoyl, N,N-dimethylcarbamoyl, N,N-diethylcarbamoyl, Nphenylcarbamoyl, N-acetylcarbamoyl, N-benzoylcarbamoyl, and N-(p-methoxyphenyl)carbamoyl group.

The "carbamoyl*oxy group" includes a carbamoyloxy, N-methylcarbamoyloxy, N,N-dimethylcarbamoyloxy, N-ethylcarbamoyloxy, and N-phenylcarbamoyloxy group.

The "thiocarbamoyl* group" includes a thiocarbamoyl, N-methylthiocarbamoyl, and Nphenylthiocarbamoyl group.

The "$C_{6-10}$aryl*methyl group" includes a benzyl, naphthylmethyl, p-methylbenzyl, p-methoxybenzyl, p-chlorobenzyl, and p-nitrobenzyl group.

The "di$C_{6-10}$aryl*methyl group" includes a benzhydryl and di(p-tolyl)methyl group.

The "tri$C_{6-10}$aryl*methyl group" includes a trityl and tri(p-tolyl)methyl group.

The "C$_{6-10}$aryl*methylene group" includes a benzylidene, p-methylbenzylidene, and p-chlorobenzylidene group.

The "C$_{6-10}$aryl*thio group" includes an o-nitrophenylthio group.

The "an amino group protected by a substituted silyl group" means a silyl group which is represented, combined with an amino group to be protected, by the general formula

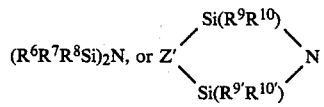

wherein R$^6$, R$^7$, R$^8$, R$^9$, R$^{10}$, R$^{9'}$, and R$^{10'}$ are a C$_{1-6}$alkyl group or C$_{6-10}$aryl* group and these groups may be the same or different from each other, and Z' is a C$_{1-3}$alkylene group such as a methylene, ethylene and propylene group. Trimethylsilyl, tert-butyldimethyl silyl, and -Si(CH$_3$)$_2$CH$_2$CH$_2$Si(CH$_3$)$_2$- groups are examples of such substitued silyl groups.

The C$_{1-10}$alkoxy-carbonyl group in the "2-C$_{1-10}$alkoxycarbonyl-1-methyl-1-ethenyl group" is preferably the one described before, and therefore the 2-C$_{1-10}$alkoxycarbonyl-1-methyl-1-ethenyl group includes a 2-methoxycarbonyl-1-methyl-1-ethenyl, 2-ethoxycarbonyl-1-methyl-1-ethenyl, 2-tert-butoxycarbonyl-1-methyl-1-ethenyl, 2-cyclohexyloxycarbonyl-1-methyl-1-ethenyl, and 2-norbornyloxycarbonyl-1-methy-1-ethenyl group.

The symbol R$^2$ is a hydrogen atom, a halogen atom or a nitro group. Such a halogen atom includes a fluorine, chlorine, and bromine atom, of which a chlorine atom is desirable.

The symbol R$^3$ is a hydrogen atom or a hydrocarbon residue which may be substituted. Such a hydrocarbon residue includes a C$_{1-6}$alkyl, C$_{2-6}$alkenyl, C$_{2-6}$alkynyl, C$_{3-10}$cycloalkyl, and C$_{5-6}$cycloalkenyl, among which a C$_{1-3}$alkyl or a substituted C$^{1-3}$alkyl group is preferable. Such a C$_{1-6}$alkyl group is preferably the C$_{1-6}$alkyl group described above, and exemplified by a methyl, ethyl, n-propyl, isopropyl, n-butyl, isobutyl, sec-butyl, tert-butyl, n-pentyl, and n-hexyl group, among which a methyl, ethyl or n-propyl group is desirable. The C$_{2-6}$alkenyl group is preferably the C$_{2-6}$alkenyl group described above, and in the concrete, a vinyl, allyl, isopropenyl, methallyl, 1,1-dimethylallyl, 2-butenyl, or 3-butenyl group is the example. The C$_{2-6}$alkynyl group is exemplified by an ethynyl, 1-propynyl, 2-propynyl, and propargyl group. The C$_{3-10}$cycloalkyl group is preferably the C$_{3-8}$cycloalkyl group described above, and in the concrete, a cyclopropyl, cyclobutyl, cyclopentyl, cyclohexyl, cycloheptyl, or adamantyl is included. The C$_{5-6}$cycloalkenyl group includes a 2-cyclopentenyl, 3-cyclopentenyl, 2-cyclohexenyl, 3-cyclohexenyl, cyclopentadienyl, and cyclohexadienyl group.

The substituent of these hydrocarbon residues includes a hydroxyl, C$_{1-6}$alkyl, C$_{2-6}$alkenyl, C$_{2-6}$alkynyl, C$_{3-10}$cycloalkyl, C$_{5-6}$cycloalkenyl, C$_{6-10}$aryl, C$_{7-19}$aralkyl, heterocyclic, C$_{1-6}$alkoxy, C$_{3-10}$cycloalkyloxy, C$_{6-10}$aryloxy, C$_{7-19}$aralkyloxy, heterocyclic oxy, mercapto, C$_{1-6}$alkylthio, C$_{3-10}$cycloalkylthio, heterocyclic thio, amino, monoC$_{1-6}$alkylamino, diC$_{1-6}$alkylamino, triC$_{1-6}$alkylammonium, C$_{3-10}$cycloalkylamino, C$_{6-10}$arylamino, C$_{7-19}$aralkylamino, heterocyclic amino, cyclic amino, azido, nitro, halogen atom, cyano, carboxyl, C$_{1-10}$alkoxycarbonyl, C$_{6-10}$aryloxycarbonyl, C$_{7-19}$aralkyloxycarbonyl, C$_{6-10}$aryl-acyl$^+$oxy, C$_{1-6}$alkanoyl, C$_{3-5}$alkenoyl, C$_{6-10}$aryl$^+$oxy, C$_{2-6}$alkanoyloxy, C$_{3-5}$alkenoyloxy, carbamoyl*, thiocarbamoyl*, carbamoyl*oxy, phthalimido, C$_{1-6}$alkanoylamino, C$_{6-10}$aryl-acyl$^+$amino, carboxyamino, C$_{1-10}$alkoxy-carboxamido, C$_{6-10}$aryloxy-carboxamido, and C$_{7-19}$aralkyloxy-carboxamido group; two or more of the same or different substituents may be present in each hydrocarbon residue described above. As for the substituent of hydrocarbon residue, in the concrete, the C$_{1-6}$alkyl group means the one described above, such as a methyl, ethyl, n-propyl, isopropyl, n-butyl, isobutyl, sec-butyl, tert-butyl, n-pentyl, and n-hexyl group; the C$_{2-6}$alkenyl group means the one described above, such as a vinyl, allyl, isopropenyl, mathallyl, 1,1-dimethylallyl, 2-butenyl, and 3-butenyl group; the C$_{2-6}$alkynyl group means the one described above, such as an ethynyl, 1-propynyl, 2-propynyl, and propargyl group; the C$_{3-10}$cycloalkyl group means the one described above, such as a cyclopropyl, cyclobutyl, cyclopentyl, cyclohexyl, cycloheptyl, and adamantyl group; the C$_{5-6}$cycloalkenyl group is the one described above, such as a cyclopropenyl, 2-cyclopentenyl, 3-cyclopentenyl, 2-cyclohexenyl, 3-cyclohexenyl, cyclopentadienyl, and cyclohexadienyl group; the C$_{6-10}$aryl group means the one described above, such as a phenyl, naphthyl and biphenylyl group; the C$_{7-19}$aralkyl group is the one described above, such as a benzyl, 1-phenylethyl, 2-phenylethyl, phenylpropyl, naphthylmethyl, and benzhydryl group; the C$_{1-6}$alkoxy group means the one described above, such as a methoxy, ethoxy, n-propoxy, isopropoxy, n-butoxy, tert-butoxy, n-pentyloxy, and n-hexyloxy group; the C$_{3-10}$cycloalkyloxy group means the one described above, such as a cyclopropyloxy, and cyclohexyloxy group; the C$_{6-10}$aryloxy group means the one described above, such as a phenoxy, and naphthyloxy group; the C$_{7-19}$aralkyloxy group means the one described above, such as a benzyloxy, 1-phenylethyloxy, 2-phenylethyloxy, and benzhydryloxy group; the C$_{1-6}$alkylthio group means the one described above, such as a methylthio, ethylthio, n-propylthio, and n-butylthio, group; the C$_{3-10}$cycloalkylthio group means the one described above, such as a cyclopropylthio and cyclohexylthio group; the C$_{6-10}$arylthio means the one described above, such as a phenylthio, and naphthylthio group; the C$_{7-19}$aralkylthio group means the one described above, such as a benzylthio, phenylethylthio, and benzhydrylthio group; the monoC$_{1-6}$alkylamino group means the one described above, such as a methylamino, ethylamino, n-propylamino, and n-butylamino group; the diC$_{1-6}$alkylamino group means the one described above, such as a dimethylamino, diethylamino, methylethylamino, di-(n-propyl)amino, and di-(n-butyl)amino group; the triC$_{1-6}$alkylammonium group means the one described above, such as a trimethylammonium, and triethylammonium group; the C$_{3-10}$cycloalkylamino group means the one described above, such as a cyclopropylamino, cyclopentylamino, and cyclohexylamino group; the C$_{6-10}$arylamino group means the one described above, such as an anilino, and N-methylanilino group; the C$_{7-19}$aralkylamino group means the one described above, such as a benzylamino, 1-phenylethylamino, 2-phenylethylamino, and benzhydrylamino group; the cyclic amino group means the one described above, such as a pyrrolidino, piperidino, piperazino, morpholino, and 1-pyrrolyl group; the halogen atom means fluorine, chlorine, bromine, or iodine; the C$_{1-10}$alkoxycarbonyl group means the one described above, such as a methoxycarbonyl, ethoxycarbonyl, n-propoxycarbonyl, isopropoxycarbonyl, n-butoxycarbonyl, isobutoxycarbonyl, tert-butoxycarbonyl, cyclopentyloxycarbonyl, cyclohexyloxycarbonyl, and norbornyloxycarbonyl group; the $C_{6\text{-}10}$aryloxycarbonyl group means the one described above, such as a phenoxycarbonyl, and naphthyloxycarbonyl group; the $C_{7\text{-}19}$aralkyloxycarbonyl group is the one described above, such as a benzyloxycarbonyl, and benzhydryloxycarbonyl group; the $C_{6\text{-}10}$aryl-acyl+ group means the one described above, such as a benzoyl, naphthoyl, phthaloyl, and phenylacetyl group; the $C_{1\text{-}6}$alkanoyl group means the one described above, such as a formyl, acetyl, propionyl, butyryl, valeryl, pivaloyl, succinyl, and glutaryl group; the $C_{3\text{-}5}$alkenoyl group means the one described above, such as an acryloyl, crotonoyl, and maleoyl group; the $C_{6\text{-}10}$aryl-acyl+oxy group means the one described above, such as a benzoyloxy, naphthoyloxy, and phenylacetoxy group; the $C_{2\text{-}6}$alkanoyloxy group means the one described above, such as an acetoxy, propionyloxy, butyryloxy, valeryloxy, and pivaloyloxy group; the $C_{3\text{-}5}$alkenoyloxy means the one described above, such as an acryloyloxy, and crotonoyloxy group; the carbamoyl* group means the one described above, such as a carbamoyl, N-methylcarbamoyl, N-ethylcarbamoyl, N,N-dimethylcarbamoyl, N-ethylcarbamoyl, N,N-diethylcarbamoyl, N-phenylcarbamoyl, N-acetylcarbamoyl, N-benzoylcarbamoyl, N-(p-methoxyphenyl)carbamoyl, and also pyrrolidinocarbonyl, piperidinocarbonyl, pieperazinocarbonyl, and morpholinocarbonyl group; the thiocarbamoyl* group means the one described above, such as a thiocarbamoyl, N-methylthiocarbamoyl, and N-phenylthiocarbonyl group; the carbamoyl*oxy group means the one described above, such as a carbamoyloxy, N-methylcarbamoyloxy, N,N-dimethylcarbamoyloxy, N-ethylcarbamoyloxy, and N-phenylcarbamoyloxy group; the "$C_{1\text{-}6}$alkanoylamino group" includes an acetamido, propionamido, butyramido, valeramido, and pivaramido group; the "$C_{6\text{-}10}$arylacy+amino group" includes benzamido, naphthamido, and phthalimido group; the "$C_{1\text{-}10}$alkoxycarboxamido group" includes a methoxycarboxamido($CH_3OCONH-$), ethoxycarboxamido, and tert-butoxycarboxamido group; the "$C_{6\text{-}10}$aryloxycarboxamido group" includes a phenoxycarboxamido($C_6H_5OCONH-$)group; and the "$C_{7\text{-}19}$aralkyloxycarboxamido group" includes a benzyloxycarboxamido($C_6H_5CH_2OCONH-$), and benzhydryloxycarboxamido group. The heterocyclic group, and the heterocyclic group in the heterocyclic oxy, heterocyclic thio and heterocyclic amino group mean the group formed by removal of a hydrogen atom bound to a carbon atom of the heterocyclic ring, and such a heterocyclic ring includes a 5- to 8-membered ring containing 1 to several, preferably 1 to 4, hetero atoms such as a nitrogen which may be oxidized, oxygen and sulfur atom, or a condensed ring thereof. The heterocyclic groups described above in the concrete, such as a 2-pyrrolyl group, are, applicable to the said heterocyclic group. Thus, the "heterocyclic oxy group" includes a thiazolyloxy, and the "heterocyclic thio group" includes a thiazolythio group. The "heterocyclic amino group" includes a thiazolylamino, and thiadiazolylamino group.

The preferable substituted hydrocarbon residue includes a $C_{1\text{-}3}$alkyl group (a $C_{1\text{-}3}$alkyl group means a methyl, ethyl, n-propyl, isopropyl group, etc.) substituted with a hydroxyl, cycloalkyl, alkoxy, alkylthio, amino, trialkylammonium, halogen atom, carboxyl, alkoxycarbonyl, carbamoyl, cyano, azido, heterocyclic group etc., in the concrete, among many others, a cyclopropylmethyl, methoxymethyl, ethoxymethyl, 1-methoxyethyl, 2-methoxyethyl, 1-ethoxyethyl, 2-hydroxyethyl, methylthiomethyl, 2-aminoethyl, 2-(trimethylammonium)ethyl, 2-(triethylammonium)ethyl, fluoromethyl, difluoromethyl, trifluoromethyl, 2-fluoroethyl, 2,2-difluoroethyl, chloromethyl, 2-chloroethyl, 2,2-dichloroethyl, 2,2,2-trichloroethyl, 2-bromoethyl, 2-iodoethyl, 2,2,2-trifluoroethyl, carboxymethyl, 1-carboxyethyl, 2-carboxyethyl, 2-carboxypropyl, 3-carboxypropyl, 1-carboxybutyl, cyanomethyl, 1-carboxy-1-methylethyl, methoxycarbonylmethyl, ethoxycarbonylmethyl, tert-butoxycarbonylmethyl, 1-methoxycarbonyl-1-methylethyl, 1-ethoxycarbonyl-1-methylethyl, 1-tert-butoxycarbonyl-1-methylethyl, 1-benzyloxycarbonyl-1-methylethyl, 1-pivaloyloxycarbonyl-1-methylethyl, carbamoylmethyl, 2-azidoethyl, 2-(pyrazolyl)ethyl, 2-(imidazolyl)ethyl, 2-(2-oxopyrrolidin-3-yl)ethyl, 2-amino-4-thiazolylmethyl group. The most preferable hydrocarbon residue among those described above in the concrete is a straight chain $C_{1\text{-}3}$alkyl group such as a methyl, ethyl, and n-propyl, or a straight chain or branched $C_{1\text{-}3}$alkyl group, an allyl group and a propargyl group substituted with a halogen atom, a hydroxyl, alkoxy, carboxyl, alkoxycarbonyl, or cyano group, e.g. a 2-fluoroethyl, 2-chloroethyl, 2-hydroxyethyl, 2-methoxyethyl, cyanomethyl, carboxymethyl, tert-butoxycarbonylmethyl, 1-carboxy-1-methylethyl, and 1-tert-butoxycarbonyl-1-methylethyl group. When the symbol $R^{3'}$ represents one of the most preferable hydrocarbon residues described above or a hydrogen atom, the compounds of this invention [I] having the acyl group

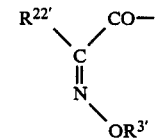

wherein $R^{22'}$ is a heterocyclic* group as the substituent $R^0$ have particularly potent antibacterial activity, and exert excellent bactericidal action especially against resistant bacteria. As described before, the heterocyclic* group $R^{22'}$ is most preferably the one having the formula

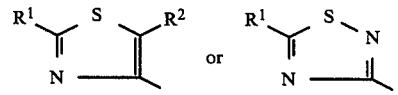

(wherein $R^1$ is an amino group which may be protected, and $R^2$ is a hydrogen atom, a halogen atom or a nitro group) and therefore the most preferable compounds [I] are those having the formula

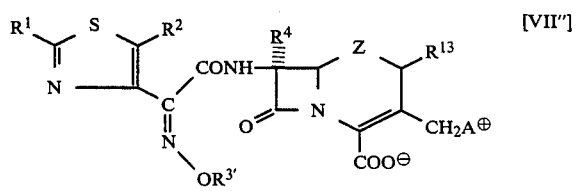

[VII'']

-continued
or

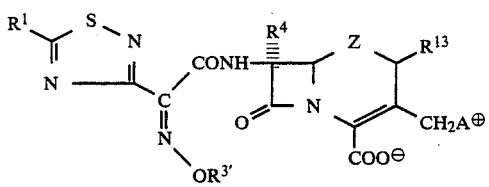

(wherein the symbols are the same as described above).
The preferable "acyl group represented by

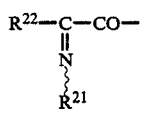

includes a 2-(2-aminothiazol-4-yl)-2(Z)-(hydroxyimino)acetyl, 2-(2-aminothiazol-4-yl)2-(Z)-(methoxyimino)acetyl, 2-(2-chloroacetamidothiazol-4-yl)-2(Z)-(methoxyimino)acetyl, 2-(2-aminothiazol-4-yl)-2(Z)-(ethoxyimino)acetyl, 2-(2-aminothiazol-4-yl)-2(Z)-(n-propoxyimino)acetyl, 2-(2-aminothiazol-4-yl)-2(Z)-(iso-propoxyimino)acetyl, 2-(2-aminothiazol-4-yl)-2(Z)-(n-butoxyimino)acetyl, 2-(2-aminothiazol-4-yl)-2(Z)-(n-hexyloxyimino)acetyl, 2-(2-aminothiazol-4-yl)-2(Z)-(cyclopropylmethyloxyimino)acetyl, 2-(2-aminothiazol-4-yl)-2(Z)-(benzyloxyimino)acetyl, 2-(2-aminothiazol-4-yl)-2(Z)-(allyloxyimino)acetyl, 2-(2-aminothiazol-4-yl)-2(Z)-(propargyloxyimino)acetyl, -(2-aminothiazol-4-yl)-2(Z)-(methoxymethyloxyimino)acetyl, 2-(2-aminothiazol-4-yl)-2(Z)-(ethoxymethyloxyimino)acetyl, 2-(2-aminothiazol-4-yl)-2(Z)-[(1-methoxyethyl)oxyimino]acetyl, 2-(2-aminothiazol-4-yl)-2(Z)-[(2-methoxyethyl)oxyimino]acetyl, 2-(2-aminothiazol-4-yl)-2(Z)-[(2-ethoxyethyl)oxyimino]acetyl, 2-(2-aminothiazol-4-yl)-2(Z)-[(1-ethoxyethyl)oxyimino]acetyl, 2-(2-aminothiazol-4-yl)-2(Z)-[(2-hydroxyethyl)oxyimino]acetyl, 2-(2-aminothiazol-4-yl)-2(Z)-(methylthiomethyloxyimino)acetyl, 2-(2-aminothiazol-4)-2(Z)-[(2-aminoethyl)oxyimino]acetyl, 2-(2-aminothiazol-4-yl)-2(Z)-(fluoromethyloxyimino)acetyl, 2-(2-aminothiazol-4-yl)-2(Z)-(difluoromethyloxyimino)acetyl, 2-(2-aminothiazol-4-yl)-2(Z)-(trifluoromethyloxyimino)acetyl, 2-(2-aminothiazol-4-yl)-2(Z)-[(2-fluoroethyl)oxyimino]acetyl, 2-(2-aminothiazol-4-yl)-2(Z)-[(2,2-difluoroethyl)oxyiminoacetyl, 2-(2-aminothiazol-4-yl)-2(Z)-(chloromethyloxyimino)acetyl, 2-(2-aminothiazol-4-yl)-2(Z)-[(2-chloroethyl)oxyimino]acetyl, 2-(2-aminothiazol-4-yl)-2(Z)-[(2,2-dichloroethyl)oxyimino]acetyl, 2-(2-aminothiazol-4-yl)-2(Z)-[(2,2,2-trichloroethyl)oxyimino]acetyl, 2-(2-aminothiazol-4-yl)-2(Z)-[(2-bromoethyl)oxyimino]acetyl, 2-(2-aminothiazol-4-yl)-2(Z)-[(2-iodoethyl)oxyimino]acetyl, 2-(2-aminothiazol-4-yl)-2(Z)-[(2,2,2-trifluoroethyl)oxyimino]acetyl, 2-(2-aminothiazol-4-yl)-2(Z)-(carboxymethyloxyimino)acetyl, 2-(2-aminothiazol-4-yl)-2(Z)-(1-carboxyethyloxyimino)acetyl, 2-(2-aminothiazol-4-yl)-2(Z)-[(2-carboxyethyl)oxyimino]acetyl, 2-(2-aminothiazol-4-yl)-2(Z)-(1-carboxypropyloxyimino)acetyl, 2-(2-aminothiazol-4-yl)-2(Z)-[(3-carboxypropyl)oxyimino]acetyl, 2-(2-aminothiazol-4-yl)-2(Z)-[(1-carboxybutyl)oxyimino]-acetyl, 2-(2-aminothiazol-4-yl)-2(Z)-(cyanomethyloxyimino)acetyl, 2-(2- aminothiazol-4-yl)-2(Z)-[(1-carboxy-1-methylethyl)oxyimino]acetyl, 2-(2-aminothiazol-4-yl)-2(Z)-(methoxycarbonylmethyloxyimino) acetyl, 2-(2-aminothiazol-4-yl)-2(Z)-(ethoxycarbonylmethyloxyimino)acetyl, 2-(2-aminothiazol4-yl)-2(Z)-[(tert-butoxycarbonylmethyl)oxyimino]acetyl, 2-(2-aminothiazol-4-yl)-[1-(tert-butoxycarbonyl)-ethoxyimino]acetyl, 2-(2-aminothiazol-4-yl)-2(Z)-[(1-methoxycarbonyl-1-methylethyl)oxyimino]acetyl, 2-(2-aminothiazol-4-yl)-2(Z)-[(1-ethoxycarbonyl-1-methylethyloxyimino]acetyl, 2-(2-aminothiazol-4-yl)-2(Z)-[(1-tert-butoxycarbonyl-1-methylethyl)oxyimino]acetyl, 2-(2-aminothiazol-4-yl)-2(Z)-[1-(tert-butoxycarbonyl)propoxyimino]acetyl, 2-(2-aminothiazol-4-yl)-2(Z)-[(1-benzyloxycarbonyl-1-methylethyl)oxyimino]acetyl, 2-(2-aminothiazol-4-yl)-2(Z)-[(1-pivaloyloxycarbonyl-1-methylethyl)oxyimino]acetyl, 2-(2-aminothiazol-4-yl)-2(Z)-(carbamoylmethyloxyimino)acetyl, 2-(2-aminothiazol-4-yl)-2(Z)-[1-(1-carbamoyl-1-methyl)ethyloxyimino] acetyl, 2-(2-aminothiazol-4-yl)-2(Z)-[(2-azidoethyloxyimino)acetyl, 2-(2-aminothiazol-4-yl)-2(Z)-(phenoxycarbonyloxyimino)acetyl, 2-(2-amino-5-chlorothiazol-4-yl)-2(Z)-(hydroxyimino)acetyl, 2-(2-amino-5-chlorothiazol-4-yl)-2(Z)-(methoxyimino)acetyl, 2-(2-amino-5-chlorothiazol-4-yl)-2(Z)-(ethoxyimino)acetyl, 2-(2-amino-5-chlorothiazol-4-yl)-2(Z)-(n-propoxyimino)acetyl, 2-(2-amino-5-chlorothiazol-4-yl)-2(Z)-[(2-fluoroethyl)oxyimino]acetyl, 2-(2-amino-5-chlorothiazol-4-yl)-2(Z)-[(2-chloroethyl)-oxyimino]acetyl, 2-(2-amino-5-chlorothiazol-4-yl)-2(Z)-(carboxymethyloxyimino)acetyl, 2-(2-amino-5-chlorothiazol-4-yl)-2(Z)-[(tert-butoxycarbonylmethyl)-oxyimino]acetyl, 2-(2-amino-5-chlorothiazol-4-yl)-2(Z)-[(1-carboxy-1-methylethyl)oxyimino]acetyl, 2-(2-amino-5-chlorothiazol-4-yl)-2(Z)-[(1-tert-butoxycarbonyl-1-methylethyl)oxyimino]acetyl, 2-(2-amino-5-bromothiazol-4-yl)-2(Z)-(ethoxyimino)acetyl, 2-(5-amino-1,2,4-thiadiazol-3-yl)-2(Z)-(hydroxyimino)acetyl, 2-(5-amino-1,2,4-thiadiazol-3-yl)-2(Z)-(methoxyimino)acetyl, 2-(5-amino-1,2,4-thiadiazol-3-yl)-2(Z)-(ethoxyimino)acetyl, 2-(5-amino-1,2,4-thiadiazol-3-yl)-2(Z)-[(2-fluoroethyl)oxyimino]acetyl, 2-(5-amino-1,2,4-thiadiazol-3-yl)-2(Z)-[(2-chloroethyl)oxyimino]acetyl, 2-(5-amino-1,2,4-thiadiazol-3-yl)-2(Z)-(carboxymethyloxyimino)acetyl, 2(5-amino-1,2,4-thiadiazol-3-yl)-2(Z)-[(1-carboxy-1-methylethyl)oxyimino]acetyl, 2-(5-amino-1,2,4-thiadiazol-3-yl)-2(Z)-[(1-tert-butoxycarbonyl-1methylethyl)oxyimino]acetyl, 2-(5-amino-isoxazol-3-yl)-2(Z)-(ethoxyimino)acetyl, 2-(5-amino-1,2,4-oxadiazol-3-yl)-2(Z)-(ethoxyimino)acetyl, 2-(2-imino-3-hydroxythiazolin-4-yl)-2(Z)-(ethoxyimino)acetyl, 2-(2-amino-3-oxidothiazol-4-yl)-2(Z)-(ethoxyimino)acetyl, 2-thienyl-2(Z)-(methoxyimino)acetyl, 2-thienyl-2(Z)-(ethoxyimino)acetyl, 2-furyl-2(Z)-(methoxyimino)acetyl, 2-furyl-2(Z)-(ethoxyimino)acetyl, 2-(1,3,4-thiadiazolyl)-2(Z)-(ethoxyimino)acetyl, 2-(p-hydroxyphenyl)-2(Z)-(ethoxyimino)acetyl, 2-phenyl-2(Z)-(ethoxyimino)acetyl, 2-phenyl-2(Z)-(hydroxyimino)acetyl, 2-[p-(Y-D-glutamyloxy)phenyl]-2(Z)-(hydroxyimino)acetyl, and 2-[p-(3-amino-3-carboxypropoxy)-phenyl]-2(Z)-(hydroxyimino)acetyl.

The $C_{1-6}$alkanoyl* group described above as an acyl group ($R^b$) includes, in addition to the $C_{1-6}$alkanoyl group described above, e.g. a heterocycle*

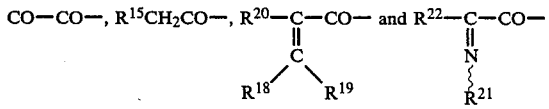

group, also a trifluoroacetyl, 4-carboxybutyryl, 5-amino-5-carboxyvaleryl, 5-oxo-5-carboxyvaleryl, N-[2-(2-amino-4-thiazolyl)-2(Z)-(methoxyimino)acetyl]-D-alanyl, N-[2-(2-amino-4-thiazolyl-2(Z)-(methoxyimino)acetyl]-D-phenylglycyl, and 2-(2-amino-4-thiazolyl)-2-[2-(2-amino-4-thiazolyl)-2(Z)-(methoxyimino)acetamido]acetyl group.

As an acyl group ($R^b$), except the $C_{1-6}$alkanoyl* group, may be mentioned a $C_{3-5}$alkenoyl* group such as an acryloyl, crotonoyl, maleoyl, cinnamoyl, p-chlorocinnamoyl and β-phenylcinnamoyl group described above; a $C_{3-10}$cycloalkylcarbonyl group such as a cyclopropylcarbonyl, cyclobutylcarbonyl, cyclopentylcarbonyl, cyclohexylcarbonyl, cycloheptylcarbonyl, and adamantylcarbonyl group described above; a $C_{5-6}$cycloalkenylcarbonyl group such as a cyclopentenylcarbonyl, cyclopentadienylcarbonyl, cyclohexenylcarbonyl and cyclohexadienylcarbonyl group described above; a $C_{6-10}$aryl*carbonyl group such as a benzoyl, naphthoyl, p-toluoyl, p-tert-butylbenzoyl, p-hydroxybenzoyl, p-methoxybenzoyl, p-tert-butoxybenzoyl, p-chlorobenzoyl, and p-nitrobenzoyl group described above, a "heterocyclic* carbonyl group" such as a 2- or 3-pyrrolylcarbonyl, 3-, 4- or 5-pyrazolylcarbonyl, 2-, 4- or 5-imidazolylcarbonyl, 1,2,3- or 1,2,4-triazolylcarbonyl, 1H- or 2H-tetrazolylcarbonyl, 2- or 3-furylcarbonyl, 2- or 3-thienylcarbonyl, 2-, 4- or 5-oxoazolylcarbonyl, 3-, 4- or 5-isoxazolylcarbonyl, 1,2,3-oxadiazol-4- or 5-ylcarbonyl, 1,2,4-oxadiazol-3 or 5-ylcarbonyl, 1,2,5- or 1,3,4-oxadiazolylcarbonyl, 2-, 4- or 5-thiazolylcarbonyl, 2-amino-4-thiazolylcarbonyl, 3-, 4- or 5-isothiazolylcarbonyl, 1,2,3-thiadiazol-4 or 5-ylcarbonyl, 1,2,4-thiadiazol-3 or 5-ylcarbonyl, 5-amino-1,2,4-thiadiazol-3-yl-carbonyl, 1,2,5- or 1,3,4-thiadiazolylcarbonyl, 2- or 3-pyrrolidinylcarbonyl, 2-, 3- or 4-pyridylcarbonyl, 2-, 3- or 4-pyridylcarbonyl-N-oxido, 3- or 4-pyridazinylcarbonyl, 3- or 4-pyridazinylcarbonyl-N-oxido, 2-, 4- or 5-pyrimidinylcarbonyl, 2-, 4- or 5-pyrimidinylcarbonyl-N-oxido, pyrazinylcarbonyl, 2-, 3- or 4-piperidinylcarbonyl, piperazinylcarbonyl, 3H-indol-2- or 3-ylcarbonyl, 2-, 3- or 4-pyranylcarbonyl, 2-, 3- or 4-thiopyranylcarbonyl, benzopyranylcarbonyl, quinolylcarbonyl, pyrido[2,3-d]pyrimidinylcarbonyl, 1,5-, 1,6-, 1,7-, 1,8-, 2,6- or 2,7-naphthylidylcarbonyl, thieno[2,3-b]pyridylcarbonyl, pyrimidopyridylcarbonyl, pyradinoquinolylcarbonyl, and 3-(2,6-dichlorophenyl)-5-methylisoxazol-4-ylcarbonyl.

The protecting groups for the amino group as the substituent $R^0$ (hereinafter represented by the symbol $R^c$) are the same as described above as the protecting groups for the amino group which may be protected (represented by the symbol $R^1$) such as a phthaloyl, $C_{1-6}$allkyl*sulfonyl, camphorsulfonyl, $C_{1-6}$aryl*sulfonyl, substituted oxycarbonyl*, carbamoyl*, thiocarbamoyl*, $C_{6-10}$aryl*methyl, di$C_{6-10}$aryl*methyl, tri$C_{6-10}$aryl*methyl, $C_{6-10}$aryl*methylene, $C_{6-10}$aryl*thio, substituted silyl, and 2-$C_{1-10}$alkoxy-carbonyl-1-methyl1-ethenyl group, among which a phthaloyl, substituted oxycarbonyl, $C_{6-10}$aryl*methyl, di$C_{6-10}$aryl*methyl, or tri$C_{6-10}$aryl*methyl is preferable. Therefore the protecting group for the amino group as the substituent $R^0$ includes, in the concrete, a phthaloyl, methoxycarbonyl, ethoxycarbonyl, n-propoxycarbonyl, isopropoxycarbonyl, n-butoxycarbonyl, tert-butoxycarbonyl, cyclohexyloxycarbonyl, norbornyloxy carbonyl, phenoxycarbonyl, naphthyloxycarbonyl, benzyloxycarbonyl, methoxymethyloxycarbonyl, acetylmethyloxycarbonyl, 2-trimethylsilylethoxycarbonyl, 2-methanesulfonylethoxycarbonyl, 2,2,2-trichloroethoxycarbonyl, 2-cyanoethoxycarbonyl, p-methylphenoxycarbonyl, p-methoxyphenoxycarbonyl, p-chlorophenoxycarbonyl, p-methylbenzyloxycarbonyl, p-methoxybenzyloxycarbonyl, p-chlorobenzyloxycarbonyl, p-nitrobenzyloxycarbonyl, benzhydryloxycarbonyl, cyclopropyloxycarbonyl, cyclopentyloxycarbonyl, cyclohexyloxycarbonyl, benzyl, naphthylmethyl, p-methylbenzyl, p-methoxybenzyl, p-chlorobenzyl, p-nitrobenzyl, benzhydryl, di(p-tolyl)methyl, or trityl group.

The symbol $R^4$ in the compound (I) of this invention means a hydrogen atom, a methoxy group or a formamido group (HCONH—).

The symbols $R^{13}$ in the compound (I) of this invention means a hydrogen atom, a methyl group, a hydroxyl group, or a halogen atom. The said halogen atom is fluorine, chlorine, bromine or iodine.

The substituent $A\oplus$ in the compound [I] is a condensed triazolio group which may be substituted. The said condensed triazolio group is preferably a group formed by joining a triazolio group with a 5- or 6-membered heterocycle, more preferably, by sharing a C-N tond with each other. One of the two residual nitrogen atoms in the triazole ring extends a binding arm which results in formation of a quaternary nitrogen among the nitrogens of the ring. The said condensed ring means the one formed by condensing a triazolio rin and a 5- or 6-membered aromatic heterocycle and the condensed ring may be condensed further with another aromatic ring (e.g. benzene ring) or aromatic heterocycle ring (e.g. above-mentioned 5 or 6- membered heterocyclic rings). Condensed triazolio group which may be substituted ($A\oplus$) is represented by the following general formulas [$A^1$] to [$A^5$]

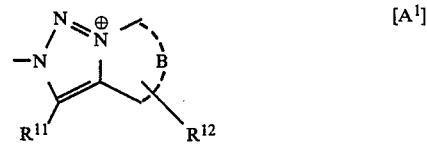

[$A^1$]

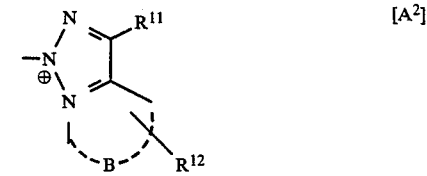

[$A^2$]

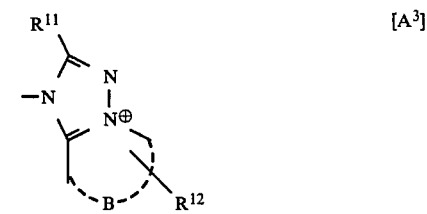

[$A^3$]

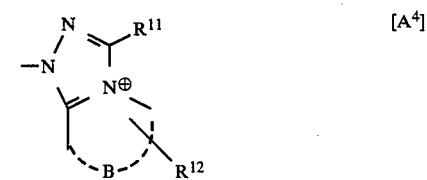

[$A^4$]

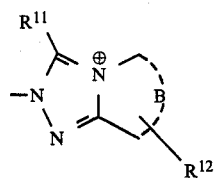

[A⁵]

wherein B is a group which forms a 5- or 6-membered aromatic heterocyclic ring which may be condensed further with another aromatic ring or aromatic heterocyclic ring; $R^{11}$ is a hydrogen atom or a substituent on the triazole ring; and $R^{12}$ is a hydrogen atom or a substituent on the ring which is condensed with the triazole ring. B consists of carbon atom(s), nitrogen atom(s), oxygen atom(s) and/or sulfur atom(s), and one of the nitrogen atom may have a hydrogen atom or a substituent, or form another condensed ring together with an adjacent carbon atom. The ring B preferably contains 1 to 4 hetero atoms selected from nitrogen, oxygen and sulfur. $A^1$ groups include in the concrete,

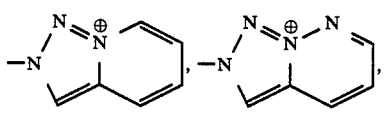

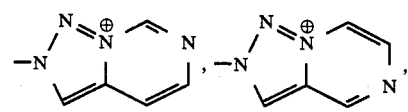

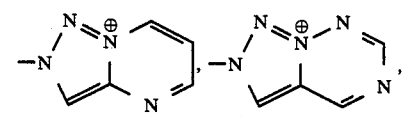

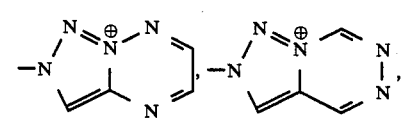

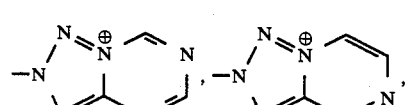

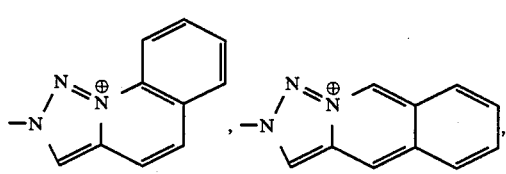

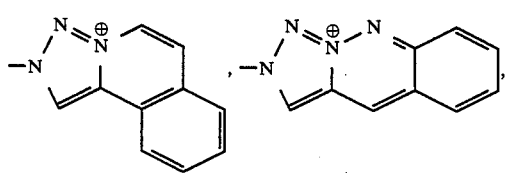

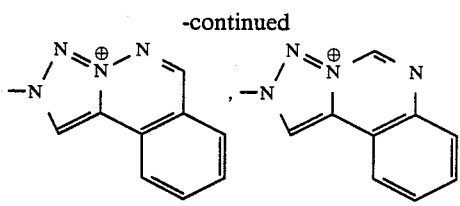

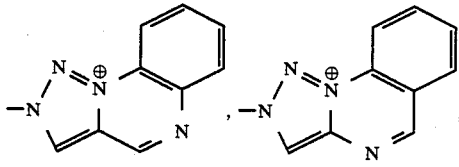

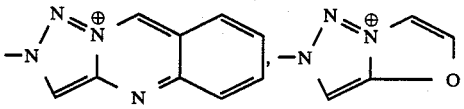

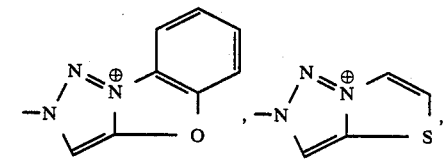

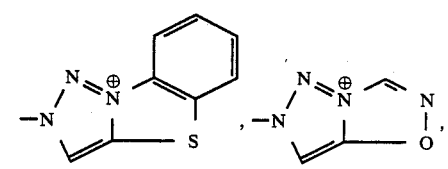

The $A^2$ group may be embodied as follows, for example;

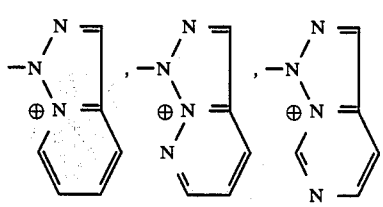

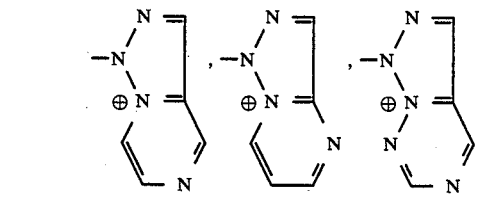

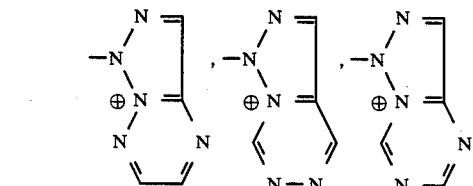
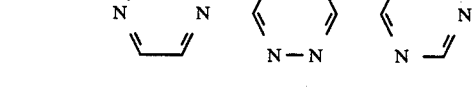

-continued
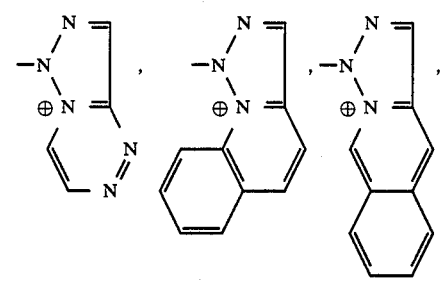
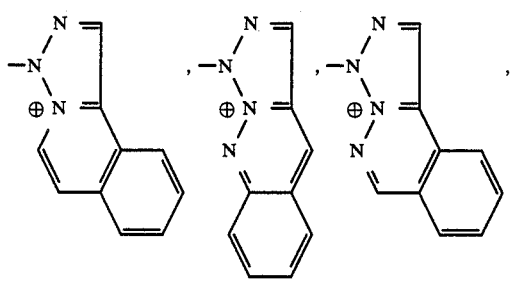
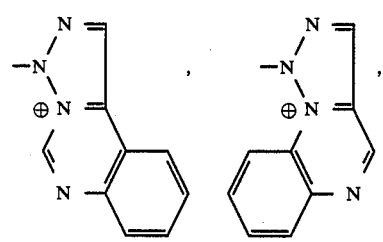
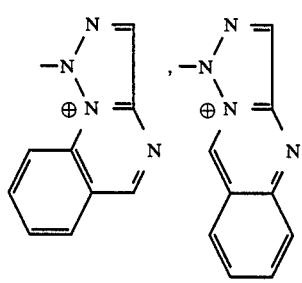
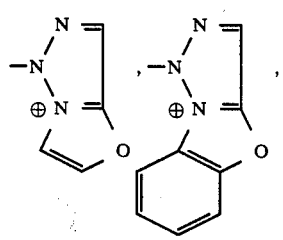
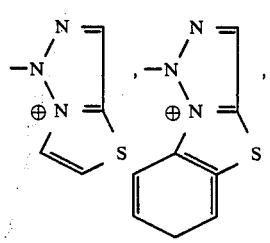
-continued
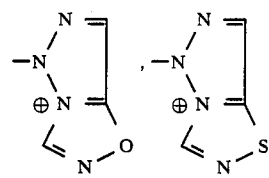
The A³ group may be embodied as follows, for example;
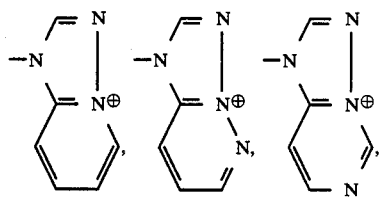
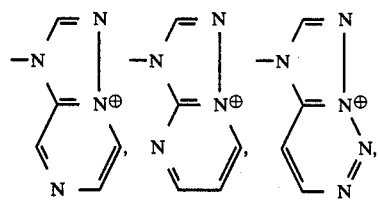
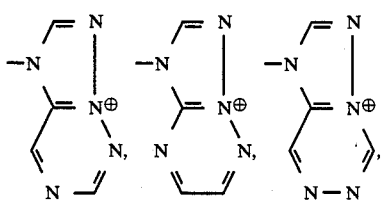
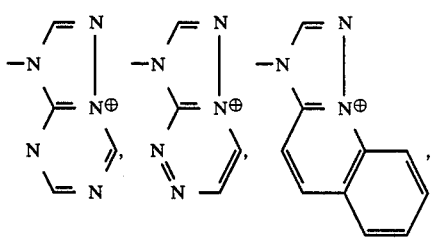
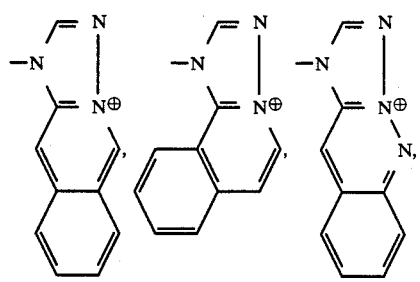
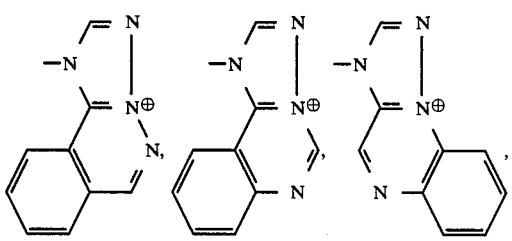

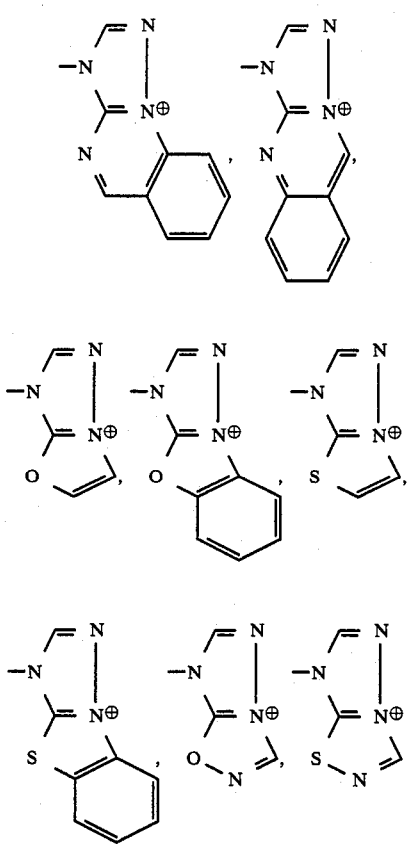
The A⁴ group may be embodied as follows, for example;
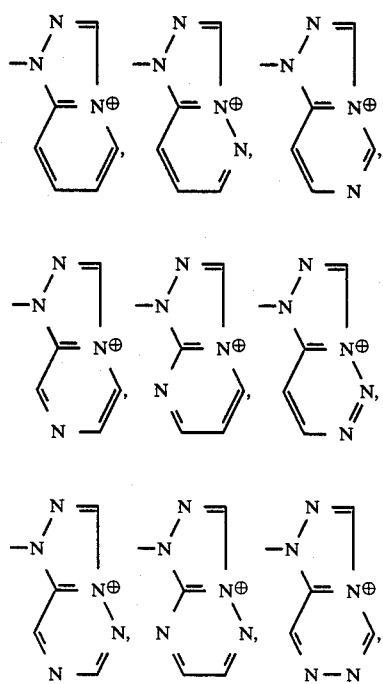
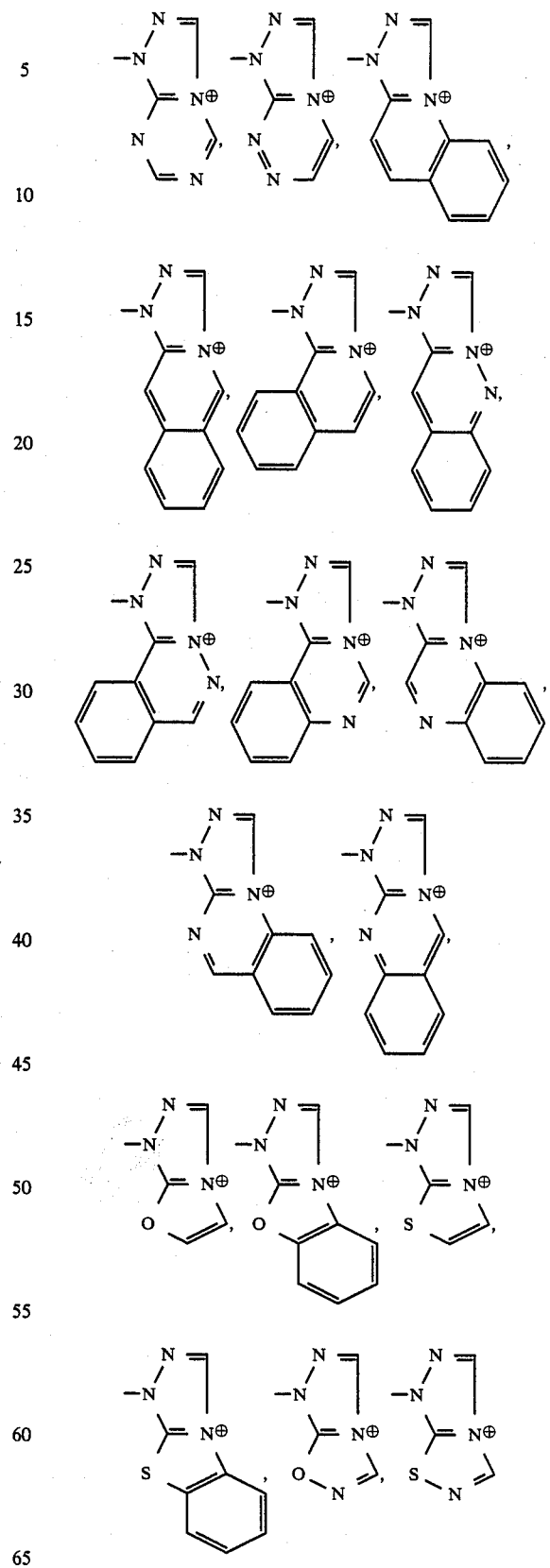
The A⁵ group may be embodied as follows, for example;

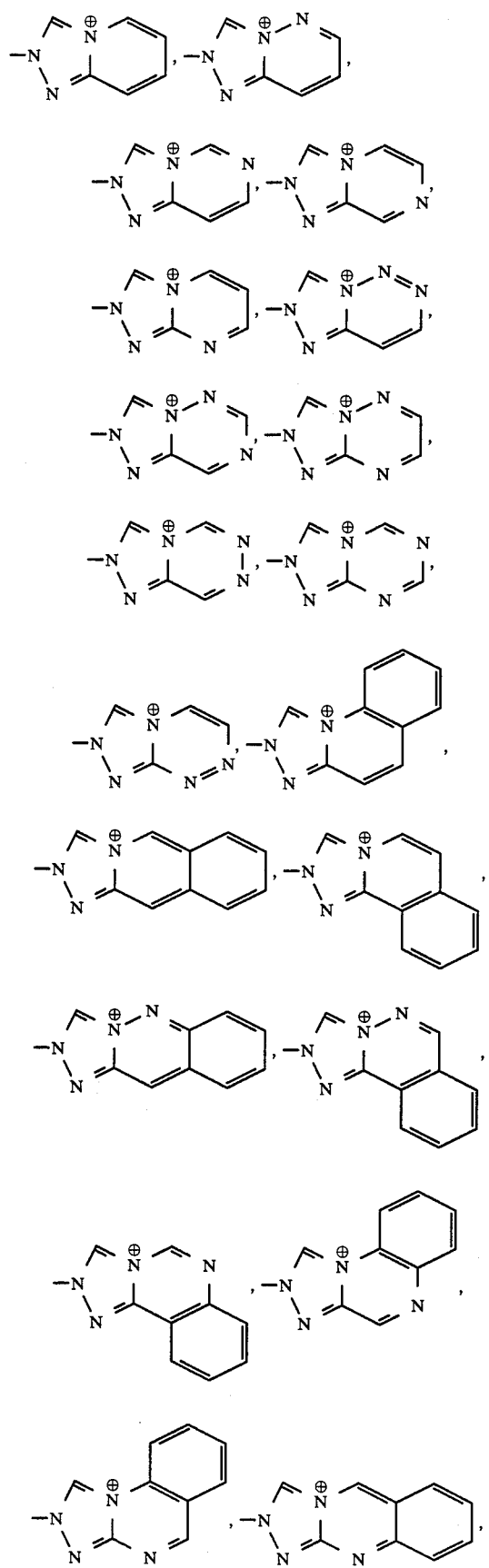
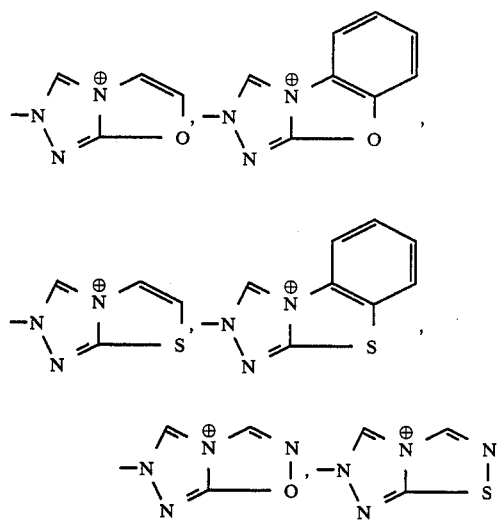
Among them, such groups as a
[1,2,3]triazolo[1,5-a]pyridinium-3-yl
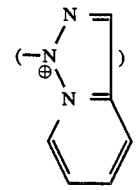
[1,2,3]triazolo[1,5-a]pyridinium-2-yl
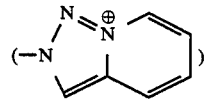
[1,2,4]triazolo[1,5-a]pyridinium-1-yl
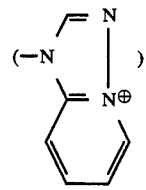
[1,2,4]triazolo[4,3-a]pyridinium-1-yl
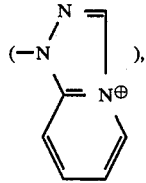
[1,2,4]triazolo[4,3-a]pyridinium-2-yl
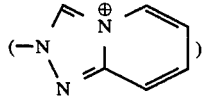
[1,2,4]triazolo[1,5-a]pyrimidinium-1-yl -continued

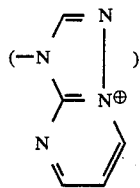

[1,2,4]triazolo[4,3-a]pyrimidinium-1-yl

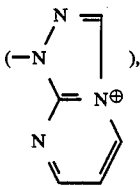

[1,2,4]triazolo[4,3-b]pyridazinium-1-yl

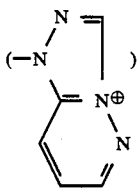

[1,2,4]triazolo[4,3-b]pyridazinium-2-yl or

[1,2,4]triazolo[1,5-b]pyridazinium-1-yl group

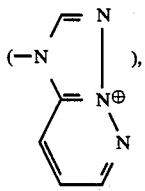

are preferable.

In the formulas [A$^1$]-[A$^5$] described above and the A$^1$ group to A$^5$ group described in the concrete, the positive charge of the substituent A⊕ is attached, for convenience, to the nitrogen atom on the bridge head of the condensed ring, but in some cases the said quaternary nitrogen atom may be assigned to another nitrogen atom in the triazole ring. Futhermore the positive charge may be delocalized in the triazole ring in some cases and in the whole condensed ring in other cases. Therefore, for example,

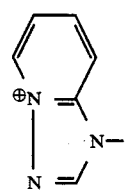

described above can be expressed as

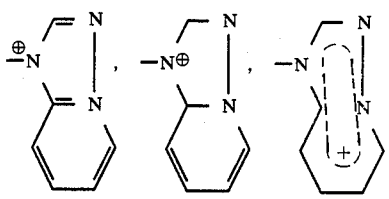

etc. The degree of delocalization of the positive charge various depending upon the states of the compound [I] (whether it is a solid or in a solution, kind of the solvent, acidity of the solution, temperature, kind of the substituent(s), etc.) and therefore this invention covers all the cases, from the one where the positive charge is localized to a certain nitrogen atom to the one where the positive charge is delocalized over the triazole ring or the whole condensed ring. The substituents R$^{11}$ and R$^{12}$ on the condensed ring A include those groups, e.g. a hydroxyl, hydroxyC$_{1-6}$alkyl, C$_{1-6}$alkyl, C$_{2-6}$alkenyl, C$_{2-6}$alkynyl, C$_{4-6}$alkadienyl, C$_{3-10}$cycloaklyl, C$_{5-6}$cycloalkenyl, C$_{3-10}$cycloaklyl-C$_{1-6}$alkyl, C$_{6-10}$aryl, C$_{7-12}$aralkyl, diC$_{6-10}$arylmethyl, triC$_{6-10}$arylmethyl, heterocyclic, C$_{1-6}$alkoxy, C$_{1-6}$alkoxyC$_{1-6}$alkyl, C$_{3-10}$cycloaklyloxy, C$_{6-10}$aryloxy, C$_{7-19}$aralkyloxy, mercapto, mercaptoC$_{1-6}$alkyl, sulfo, sulfoC$_{1-6}$alkyl, C$_{1-6}$alkylthio, C$_{1-6}$alkoxycarbonylC$_{1-6}$alkylthio, hydroxyC$_{1-6}$alkylthio, C$_{1-6}$alkylthioC$_{1-6}$alkyl, C$_{3-10}$cycloalkylthio, C$_{6-10}$arylthio, C$_{7-19}$aralkylthio, amino, amino C$_{1-6}$alkyl, monoC$_{1-6}$alkylamino, diC$_{1-6}$alkylamino, monoC$_{1-6}$alkylamino C$_{1-6}$alkyl, diC$_{1-6}$alkylamino C$_{1-6}$alkyl, C$_{3-10}$cycloalkylamino, C$_{6-10}$arylamino, C$_{7-19}$aralkylamino, cyclic amino, cyclic amino C$_{1-6}$alkyl, cyclic amino C$_{1-6}$alkylamino, azido, nitro, halogen atom, halogeno C$_{1-6}$alkyl, cyano, cyano C$_{1-6}$alkyl, carboxyl, carboxy C$_{1-6}$alkyl, C$_{1-10}$alkoxy-carbonyl, C$_{1-10}$alkoxy-carbonylC$_{1-6}$alkyl, C$_{6-10}$aryloxy-carbonyl, C$_{7-19}$aralkyloxycarbonyl, C$_{6-10}$aryl-acyl$^+$, C$_{1-6}$alkanoyl, C$_{2-6}$alkanoyl C$_{1-6}$alkyl, C$_{3-5}$alkenoyl, C$_{6-10}$aryl-acyl$^+$oxy, C$_{2-6}$alkanoyloxy, C$_{2-6}$alkanoyloxy C$_{1-6}$alkyl, C$_{3-5}$alkenoyloxy, carbamoyl C$_{1-6}$alkyl, carbamoyl*, thiocarbamoyl*, carbamoyl-*oxy, carbamoyloxy C$_{1-6}$alkyl, C$_{1-6}$alkanoylamino, C$_{6-10}$aryl-acyl$^+$amino, sulfonamido, carboxyamino, C$_{1-10}$alkoxy-carboxamido, C$_{6-10}$aryloxycarboxamido, and C$_{7-19}$aralkyloxy-carboxamido group. Among the substituents described above, the "C$_{4-6}$alkadienyl group" is for example a 1,3-butadienyl; the "C$_{3-10}$cycloaklyl C$_{1-6}$alkyl group" is for example a cyclopentylmethyl or cyclohexylmethyl group; and the halogen atom is fluorine, chlorine, or bromine. All other groups include those described before. R$^{12}$ is one or more of these substituents, and in the latter case they are the same or different.

As preferable examples of the substituent R$^{11}$, there may be mentioned a hydroxy C$_{1-6}$alkyl, C$_{1-6}$alkyl, C$_{1-6}$alkoxy, C$_{1-6}$alkylthio, C$_{1-6}$alkoxycarbonylC$_{1-6}$alkylthio, hydroxy C$_{1-6}$alkylthio, amino, monoC$_{1-6}$alkylamino, diC$_{1-6}$alkylamino, cyano or carbamoyl* group, halogen atom or so on. R$^{12}$ is preferably one substituent or two, the same or different, substituents selected from the groups mentioned as preferable example of the substituent R$^{11}$.

Thus, as preferable examples of the substituent A⊕ in Compound [I], there may be mentioned a [1,2,3]triazolo[1,5-a]pyridinium-3- or -2-yl, [1,2,4]triazolo[1,5-a]pyridinium-1-yl, [1,2,4]triazolo[4,3-a]pyridinium-1- or -2-yl, [1,2,4]triazolo[1,5- a]pyrimidinium-1-yl, [1,2,4]triazolo[4,3-a]pyrimidinium-1-yl, [1,2,4]triazolo[4,3-b]pyridazinium-1- or -2-yl, [1,2,4]triazolo[1,5-b]pyridazinium-1-yl or so on which may be substituted by one to three substituents, the same or different, selected from the class of a hydroxy $C_{1-6}$alkyl, $C_{1-6}$alkyl, $C_{1-6}$alkoxy, $C_{1-6}$alkylthio, $C_{1-6}$alkoxycarbonyl$C_{1-6}$alkylthio, hydroxy $C_{1-6}$alkylthio, amino, mono$C_{1-6}$alkylamino, di$C_{1-6}$alkylamino, cyano or carbamoyl* group and a halogen atom.

In the compound [I] described above, the symbol $\ominus$ marked on the shoulder of the carboxyl group (—COO) at the 4-position indicates that the carboxyl group is present as a carboxylate anion, pairing with the positive charge on the substituent A to form an intramolecular salt. On the other hand, as described above, the compound [I] includes a pharmaceutically acceptable salt or ester thereof. The pharmaceutically acceptable salts include the inorganic base salts, ammonium salts, organic base salts, inorganic acid addition salts, organic acid addition salts, and basic amino acid salts. The inorganic bases to form the inorganic base salts include alkali metals (such as sodium and potassium) and alkali earth metals (such as calcium): the organic bases to form the organic base salts include procaine, 2-phenylethylbenzylamine, dibenzylethylenediamine, ethanolamine, diethanolamine, trishydroxymethylaminomethane, polyhydroxyalkylamine, and N-methylglucosamine; the inorganic acids to form the inorganic acid addition salts include hydrochloric, hydrobromic, sulfuric, nitric, and phosphoric acids; the organic acids to form organic acid addition salts include p-toluenesulfonic, methanesulfonic, formic, trifluoroacetic, and maleic acids; the basic amino acids to form basic amino acid salts include lysine, arginine, ornithine, and hystidine. Among these salts, base salts (i.e. inorganic base salts, ammonium salts, organic base salts, and basic amino acid salts) are the base salts which can be formed when an acidic group such as a carboxyl or sulfo group is present in the substituent $R^0$ or A of the compound [I], and acid addition salts (i.e. inorganic acid addition salts and organic acid addition salts) are the salts which can be formed when a basic group such as an amino, monoalkylamino, dialkylamino, cycloalkylamino, arylamino, aralkylamino, cyclic amino, or nitrogen-containing heterocyclic group is present in the substituent $R^0$ or A in the compound [I]. The acid addition salts include also salts in which one mole of an acid is added to the carboxylate moiety (COO$\ominus$) at the 4-position and CH$_2$A$\oplus$ moiety at the 3-position so that a carboxyl group (COOH) at the 4-position and CH$_2$A$\oplus$.M$\ominus$ at the 3-position are formed, wherein M$\ominus$ is an anion formed as a result of removal of a proton H$\oplus$ from an inorganic acid or an organic acid, for example, a chloride, bromide, sulfate, p-toluenesulfonate, methanesulfonate, and trifluoroacetate ion. The pharmaceutically acceptable esters mean esters formed by esterification of the carboxyl group(s) in the molecule, and are (1) the esters which are applicable as intermediates for synthesis and (2) esters which are metabolically unstable and intoxic and are suitable for the oral administration. The esters applicable as the intermediates for synthesis include the $C_{1-6}$alkyl*, $C_{2-6}$alkenyl, $C_{3-10}$cycloaklyl, $C_{3-10}$cycloalkyl-$C_{1-6}$alkyl, $C_{6-10}$aryl*, $C_{7-12}$aralkyl*, biphenyl, di$C_{6-10}$aryl-methyl, tri$C_{6-10}$aryl-methyl, and substituted silyl esters. The "$C_{1-6}$alkyl* groups" constituting the $C_{1-6}$alkyl* esters include methyl, ethyl, n-propyl, isopropyl, n-butyl, isobutyl, sec-butyl, tert-butyl, n-pentyl, n-hexyl, benzyloxymethyl, 2-methylsulfonylethyl, 2-trimethylsilylethyl, 2,2,2,-trichloroethyl, 2-iodoethyl, acetylmethyl, p-nitrobenzoylmethyl, p-mesylbenzoylmethyl, phthalimidomethyl, succinimidomethyl, benzenesulfonylmethyl, phenylthiomethyl, dimethylaminoethyl, pyridyl-1-oxido-2-methyl, methylsulfinylmethyl, and 2-cyano-1, 1-dimethylethyl; the $C_{2-6}$alkenyl groups constituting the $C_{2-6}$alkenyl esters are those described above such as vinyl, alkyl, 1-propenyl, isopropenyl, 1-butenyl, 2-butenyl, 3-butenyl, methylally, 1,1,-dimethylallyl, and 3-methyl-3-butenyl. The $C_{3-10}$cycloalkyl groups constituting the $C_{3-10}$cycloaklyl esters are those described above, such as cyclopropyl, cyclobutyl, cyclopentyl, cyclohexyl, cycloheptyl, norbornyl, and adamantyl; the $C_{3-10}$cycloalkyl-$C_{1-6}$alkyl groups constituting $C_{3-10}$cycloalky-$C_{1-6}$alkyl esters are those described above, such as cyclopropylmethyl, cyclopentylmethyl, and cyclohexylmethyl. The "$C_{6-10}$aryl* groups" constituting the $C_{6-10}$aryl* esters include those groups e.g. phenyl, α-naphthyl, β-naphthyl, p-nitrophenyl, and p-chlorophenyl, The "$C_{7-12}$aralkyl* groups" constituting the $C_{7-12}$aralkyl* esters include those groups e.g. benzyl, 1-phenylethyl, 2-phenylethyl, phenylpropyl, naphthylmethyl, p-nitrobenzyl, p-methoxybenzyl, 1-indanyl, phenacyl, and 3,5-ditertbutyl-4-hydroxybenzyl. The di$C_{6-10}$aryl-methyl groups constituting di$C_{6-10}$aryl-methyl esters are those described above, such as benzhydryl and bis(p-methoxyphenyl)methyl. The tri$C_{6-10}$aryl-methyl groups constituting tri$C_{6-10}$aryl-methyl esters are those described above, such as trityl. The substituted silyl groups constituting substituted silyl esters are those described above, such as trimethylsilyl, tertbutyldimethysilyl, and —Si(CH$_3$)$_2$CH$_2$CH$_2$Si(CH$_3$)$_2$—. The esters described above include also the esters at the 4-position. In these compounds having ester groups described above at the 4-position, the formation of a salt of the type of CH$_2$A$\oplus$.M$\ominus$ wherein M$\ominus$ means the same as described above, occurs at the 3-position.

As the metabolically unstable, nontoxic esters, those which have already been established in the field of penicillin and cephalosporin especially for the purpose of the oral administration can be conveniently adopted also in this invention. Such metabolically unstable, nontoxic esters include $C_{2-6}$alkanoyloxy$C_{1-6}$alkyl, 1-($C_{1-6}$alkoxy) $C_{1-6}$alkyl, and 1-($C_{1-6}$alkylthio)$C_{1-6}$alkyl esters. The $C_{2-6}$alkanoyloxy$C_{1-6}$alkyl esters include acetoxymethyl, 1-acetoxyethyl, 1-acetoxybutyl, 2-acetoxyethyl, propionyloxymethyl, and pivaloyloxymethyl esters. The 1-($C_{1-6}$alkoxy)$C_{1-6}$alkyl esters include methoxymethyl, ethoxymethyl, isopropoxymethyl, 1-methoxyethyl, and 1-ethoxyethyl esters. The 1-($C_{1-6}$alkylthio)$C_{1-6}$alkyl esters include methylthiomethyl and ethylthiomethyl esters. This invention includes not only the esters described above, but also pharmaceutically acceptable compounds which are able to be converted into the compound [I] in the organism. The esters applicable as the intermediates for synthesis and the metabolically unstable, nontoxic esters described above include also the esters at the 4-position. In these compounds having the ester groups described above at the 4-position, formation of a salt represented by CH$_2$A$\oplus$.M$\ominus$, wherein M$\ominus$ is the same as described above, usually occurs at the 3-position.

When the compound [I] has a hydroxyl group, the hydroxyl group may be protected. As the hydroxy protective groups, any of those which are usually usable for protection of a hydroxyl group in the field of β-lactam and organic chemistry are applicable. That is, in addition to a $C_{2-6}$alkanoyl group, a substituted oxycarbonyl, tert-butyl, $C_{7-12}$aralkyl*, diC$_{6-10}$arylmethyl, triC$_{6-10}$aryl-methyl, 1-($C_{1-6}$alkoxy)$C_{1-6}$alkyl, 1-($C_{1-6}$alkylthio)$C_{1-6}$alkyl, or substituted silyl group described above, also an acetal residue such as 2-tetrahydropyranyl or 4-methoxy-4-tetrahydropyranyl is used.

When the compound [I] contains another amino group in addition to the amino group described above, the former amino group may also be protected. The protective groups for the said amino group are the same as described as the amino protective groups described before.

Among the compound [I], those having a nitrogen-containing heterocyclic group ($R^a$) or an acyl group ($R^b$) as the substituent $R^0$ have a broad spectrum of antibacterial activity, and can be used for prevention and treatment of various diseases due to pathogenic bacteria in man and animals, such as a respiratory tract and urinary tract infection. The antibacterial spectrum of the antibacterial compound [I] ($R^0=R^a$ or $R^b$) is characterized by;

(1) a very high activity against many species of Gram-negative bacteria, (2) a high activity against Gram-positive bacteria (such as *Staphylococcus aureus*, and *Corynebacterium diphtheriae*), (3) a remarkable antibacterial action on *Pseudomonas aeruginosa* which is not sensitive to the usual treatment with an antibiotic agent of cephalosporin series, and (4) a high activity even against many β-lactamase-producing Gram-negative bacteria (such as Escherichia sp., Enterobacter sp., Serratia sp., and Proteus sp.). The antibacterial compound [I] has a great advantage, especially against microorganisms of Pseudomonas sp., over aminoglycoside antibiotics such as amikacin and gentamicin which have conventionally been used, because the antibacterial compound [I] not only has antibacterial activities comparable to those of the aminoglycosides, but also is much less toxic to man and animals than the latter.

The antibacterial compound [I] of this invention ($R^0=R^a$ or $R^b$) is also characterized by an excellent stability, high blood level, long duration of the effect, remarkable distribution in the tissues, etc.

Methods for the production of the compound [I] of this invention are described in detail in the following. The reactions used in the methods described below are all known, and the known procedures or the procedures in accordance with the known procedures are applicable. Method of Production (1): Synthesis of the compound [II] ([I], $R^0$=hydrogen atom)

A 7-amino compound [II] ([I], $R^0$=hydrogen atom) or a salt or ester thereof can be synthesized, for example, by the reaction of a compound represented by the general formula

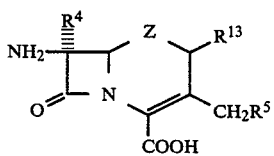

wherein the symbol $R^5$ is a hydroxyl, an acyloxy, a carbamoyloxy, a substituted carbamoyloxy group or a halogen atom, and other symbols are the same as described above, or a salt or an ester thereof, with a condensed triazole compound which may be substituted or a salt thereof (represented by A' hereinafter). That is, the reaction is written by the following formula

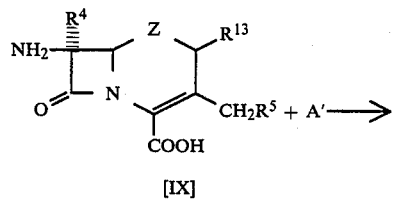

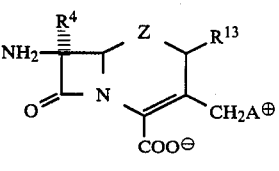

([II], $R^0$ = hydrogen atom)

wherein the symbols Z, $R^4$, $R^{13}$, $R^5$, A and A' are the same as described above.

In this case the starting material, the compound [IX] or a salt or an ester thereof may be easily obtained by using a known method or one anologous thereto. As the salts and esters of the compound [IX], those of the compound [II] described below are also here applicable.

The aryloxy groups represented by $R^5$ described above include the acyl+oxy groups described above, among which the acetoxy, chloroacetoxy, propionyloxy, butyryloxy, pivaloyloxy, 3-oxobutyryloxy, 4-chloro-3-oxobutyrylxoy, 3-carboxypropionyloxy, 4-carboxybutyryloxy, 3-ethoxycarbamoylpropionyloxy, benzoyloxy, o-carboxybenzoyloxy, o-(ethoxycarbonylcarbamoyl)benzoyloxy, and o-(ethoxycarbonylsulfamoyl)benzoyloxy groups are particularly desirable. The substituted carbamoyloxy groups represented by the symbol $R^5$ include those described above, among which the methylcarbamoyloxy, and N,N-dimethylcarbamoyloxy groups are particularly desirable. As the halogen atom represented by the symbol $R^5$, a chlorine, bromine, or iodine atom is preferable. The triazole compounds and the salts thereof (A') and the nucleophilic substitution reaction at the 3 position are described in detail below under method of Production (3-2).

This reaction proceeds in the same way as described above even when the amino group at the 7 position is protected, to yield the same compound as that synthesized by the method described below under Method of Production (4), and if necessary, a 7-amino compound [II] ([I], $R^0$=hydrogen atom) can be obtained by removal of the protective group.

Method of Production (2): Synthesis of the compound [I$^a$]($R^0=R^a$;$R^a$ is a nitrogen-containing heterocyclic group)

(2-1): The compound [I$^a$] ($R^0=R^a$) can be synthesized, for example, by the reaction of the 7-amino compound [II] obtained in the method described above under Method of Production (1) or a salt or an ester thereof (such salts and esters are described below) with a compound having the general formula R$^a$Hal(R$^a$ is a nitrogen-containing heterocyclic group, and Hal is a halogen atom such as fluorine, chlorine, bromine, or iodine) or a salt thereof. This reaction is written by the following formula.

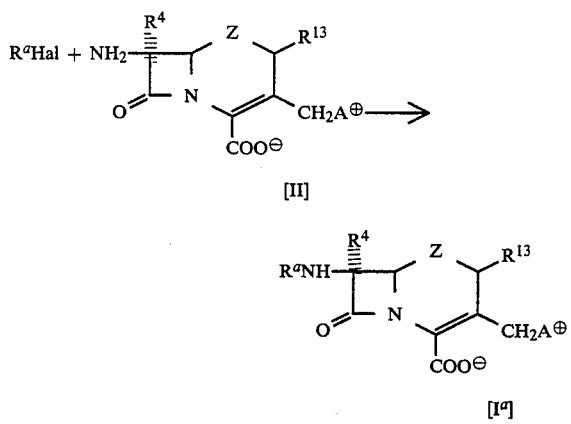

[II]

[Iᵃ]

wherein, the symbol $R^a$ represents a nitrogen-containing heterocyclic group, and the symbols Z, $R^4$, $R^{13}$, A and Hal as the same as described above.

As the halogen atom (Hal) in the compound $R^a$Hal, a fluorine atom is most frequently used. The salts of the compound $R^a$Hal include inorganic acid addition salts such as hydrochlorides, hydrobromides, sulfates, nitrates, and phosphates, and organic acid addition salts such as formates, acetates, trifluoroacetates, methanesulfonates, and p-toluenesulfonates. The reaction is preferably conducted by mixing the compound $R^a$Hal or a salt thereof with the 7-amino compound [II] or a salt or an ester thereof in water or an aqueous solvent at room temperature (about 15° to 30° C). It is necessary to adjust the pH of the reaction mixture lest the compound $R^a$Hal should be hydrolyzed prior to the reaction between the compound $R^a$Hal and the compound [II]. The optimum pH is 6 to 8.5. An acid-binding agent may be used to remove the hydrogen halide formed by the reaction from the reaction system. Such acid-binding agents include inorganic bases such as sodium carbonate, potassium carbonate, calcium carbonate, and sodium hydrogen carbonate, tertiary amines such as triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine, and N-methylmorpholine, and alkylene oxides such as propylene oxide and epichlorohydrin. In some cases an inorganic acid such as hydrochloric acid, hydrobromic acid, sulfuric acid, nitric acid, and phosphoric acid is used to prevent overalkalinity. The reaction may be carried out in an organic solvent or a mixture with water. The organic solvents which are mixed with water and used for the reaction in an aqueous solvent include ethers such as dioxane, tetrahydrofuran, diethyl ether, tert-butyl methyl ether, and diisopropyl ether, amides such as formamide, N,N-dimethylformamide, and N,N-dimethylacetamide, ketones such as acetone, methyl ethyl ketone, and methyl isobutyl ketone, and also dimethylsulfoxide, sulfolane, hexamethylphosphol amide, etc. The amount of the compound $R^a$Hal used is usually 1 to 3 moles, preferably 1 to 2 moles, per 1 mole of the 7-amino compound [II]. The reaction time varies according to the species of the 7-amino compound [II] and the compound $R^a$Hal, the kind of the solvent, reaction temperature, etc., usually being 1 minute to 48 hours, preferably 15 minutes to 3 hours.

The compound $R^a$Hal and the salts thereof are able to be synthesized easily by a known method or one analogous thereto.

By this method the following compound, for example, can be synthesized.

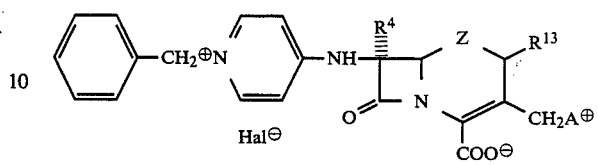

When the compound $R^a$Hal is so reactive that it is apt to be hydrolyzed, the reaction may be conducted, for example, in dry dimethylsulfoxide, in the presence of an organic base such as dry triethylamine. By this method, for example, the following compound can be synthesized.

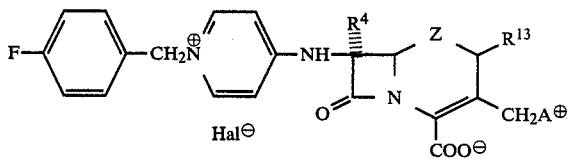

According to a known procedure, the reaction described above may be conducted in the presence of an organic acid such as p-toluenesulfonic acid, methanesulfonic acid, ethanesulfonic acid, acetic acid and butyric acid, or an inorganic acid such as hydrochloric acid, sulfuric acid, and carbon dioxide. Also in these cases fluorine is most frequently used as the halogen atom (Hal) in the compound $R^a$Hal. The reaction is conducted usually in a solvent such as dimethylformamide, tetrahydrofuran, dioxane, chloroform, methanol, acetonitrile, benzene, acetone, and water or a mixture thereof. The reaction temperature is 0° to 150° C., preferably 20° to 80° C. The reaction time is usually 30 minutes to 20 hours. By this method, for example, the following compound can be synthesized.

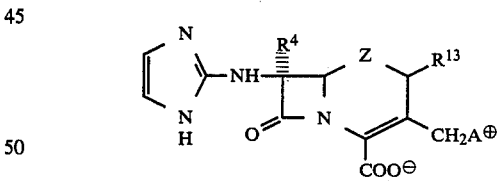

(2-2): The compound [Iᵃ] ($R^0 = R^a$) can be synthesized by the reaction of the starting compound [IX] or a salt or an ester thereof used in the method described above under method of Production (1), with the compound $R^a$Hal or a salt thereof, followed by the reaction with a triazole compound or a salt thereof (A'). This reaction is written by the following formula.

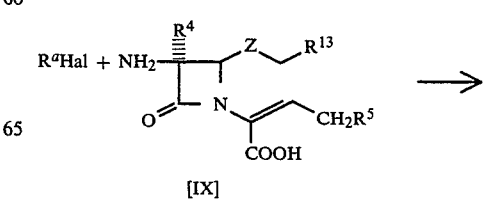

[IX]

-continued

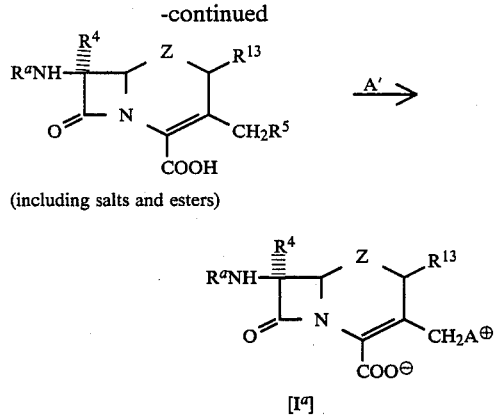

(including salts and esters)

wherein, the symbol $R^a$ is a nitrogen-containing heterocyclic group, and the symbols Z, $R^4$, $R^{13}$, $R^5$, A, A', and Hal are the same as described above. The starting compound [IX] and the salts and esters thereof and the compound $R^a$Hal and the salts thereof are those described above. The triazole compounds and the salt thereof (A') are described in detail below. The methods described under Method of Production (2-1) and Method of Production (1) are applicable.

Method of Production (3): Synthesis of the compound $[I^b]$ ($R^0=R^b$; $R^b$ is an acyl group)

(3-1): The compound $[I^b]$ ($R^0=R^b$) can be synthesized for example, by the reaction of the 7-amino compound [II] or a salt or an ester thereof obtained in the Method of Production (1) above, with a carboxylic acid represented by the general formula $R^bOH$, wherein $R^b$ is an acyl group, or a salt or a reactive derivative thereof. The reaction is written by the following formula.

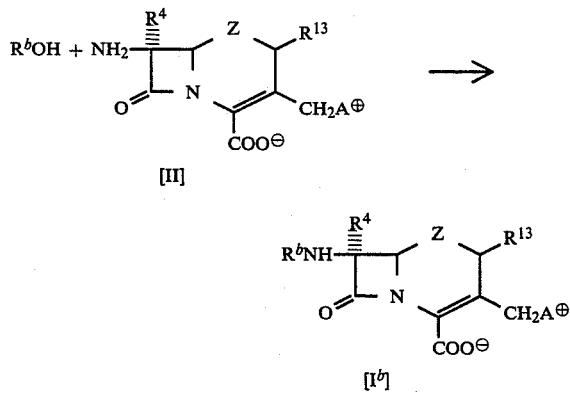

wherein the symbol $R^b$ is an acyl group, and the symbols Z, $R^4$, $R^{13}$, and A are the same as described above.

This method consists in acylating the 7-amino compound [II] with a carboxylic acid $R^bOH$ or a salt or a reactive derivative thereof. In this method the carboxylic acid, free or as a salt or a reactive derivative thereof, is used as an acylating agent of the amino group at the 7 position of the 7-amino compound [II]. That is, a free acid $R^bOH$, or an inorganic or organic salt of a free acid $R^bOH$, or a reactive derivative of a free acid $R^bOH$ such as an acid halide, an acid azide, an acid anhydride, a mixed acid anhydride, an active amide, an active ester, and active thioester are used for the acylation. The inorganic salts include the alkali metal salts (e.g. sodium salts, potassium salts), and alkaline earth metal salts (e.g. calcium salts); the organic salts include the trimethylamine salts, triethylamine salts, tert-butyldimethylamine salts, dibenzylmethylamine salts, benzyldimethylamine salts, N,N-dimethylaniline salts, pyridine salts, and quinoline salts; the acid halides include the acid chlorides and acid bromides; the mixed acid anhydrides include the mono$C_{1-6}$alkylcarboxylic acid mixed acid anhydrides (e.g. mixed acid anhydrides of a free acid $R^bOH$ with a monomethylcarboxylic, monoethylcarboxylic, monoisopropylcarboxylic, monoisobutylcarboxylic, monotert-butylcarboxylic, monobenzylcarboxylic, mono(p-nitrobenzyl)carboxylic, or monoallylcarboxylic acid), the $C_{1-6}$aliphatic carboxylic acid mixed acid anhydrides (e.g. mixed acid anhydrides of a free $R^bOH$ with acetic acid, trichloroacetic acid, cyanoacetic acid, propionic acid, butyric acid, isobutyric acid, valeric acid, isovaleric acid, pivalic acid, trifluoroacetic acid, trichloroacetic acid, or acetoacetic acid), the $C_{7-12}$aromatic carboxylic acid mixed acid anhydrides (e.g. mixed acid anhydrides of a free $R^bOH$ with benzoic acid, p-toluic acid, or p-chlorobenzoic acid), and the organic sulfonic acid mixed acid anhydrides (e.g. mixed acid anhydrides of a free acid $R^bOH$ with methanesulfonic acid, ethanesulfonic acid, benzenesulfonic acid, or p-toluenesulfonic acid); and the active amides include amides with a nitrogen-containing heterocyclic compound (e.g. acid amides of a free acid $R^bOH$ with pyrazole, imidazole, or benzotriazole, and these nitrogen-containing heterocyclic compounds may be substituted by the $C_{1-6}$alkyl group, $C_{1-6}$alkoxy group, halogen atom, oxo group, thioxo group, or $C_{1-6}$alkylthio group described above). As the active esters, any of those that can be used for this purpose in the field of synthesis of $\beta$-lactams and peptides are applicable, including, in addition to the organic phosphoric acid esters (e.g. a diethoxyphosphoric acid and diphenoxyphosphoric acid ester), a p-nitrophenyl, 2,4-dinitrophenyl, cyanomethyl, pentachlorophenyl, N-hydroxysuccinimido, N-hydroxyphthalimido, 1-hydroxybenzotriazole, 6-chloro-1-hydroxybenzotriazole, and 1-hydroxy-1H-2-pyridone ester. The active thioesters include the esters with an aromatic heterocyclic thiol compound (e.g. a 2-pyridylthiol and 2-benzothiazolylthiol ester and these heterocyclic rings may be substituted with a $C_{1-6}$alkyl group, $C_{1-6}$alkoxy group, halogen atom, or $C_{1-6}$alkylthio group). On the other hand, the 7-amino compound [II] may be used in a free form, or as a salt or an ester. The salts of the 7-amino compound [II] include inorganic base salts, ammonium salts, organic base salts, inorganic acid addition salts, and organic acid addition salts. The inorganic base salts include alkali metal salts (e.g. sodium and potassium salts), and alkaline earth metal salts (e.g. calcium salts); the organic base salts include trimethylamine, triethylamine, tert-butyldimethylamine, dibenzylmethylamine, benzyldimethylamine, N,N-dimethylaniline, pyridine, and quinoline salts; the inorganic acid addition salts include hydrochlorides, hydrobromides, sulfates, nitrates, and phosphates; and the organic acid addition salts include formates, acetates, trifluoroacetates, methanesulfonates, and p-toluenesulfonates. As the esters of the 7-amino compound [II], the esters described above as the ester derivatives of the compound [I] are applicable. That is, they include $C_{1-6}$alkyl*, $C_{2-6}$alkenyl, $C_{3-10}$cycloalkyl, $C_{3-6}$cycloalkyl$C_{1-6}$alkyl, $C_{6-10}$aryl*, $C_{7-12}$aralkyl*, di$C_{6-10}$arylmethyl, tri$C_{6-10}$arylmethyl, and $C_{2-6}$alkanoyloxy-$C_{1-6}$alkyl esters. The starting substance $R^bOH$ and the salts and the reactive derivatives thereof can be synthesized easily by a known method or a per se known one. A reactive derivative of the compound $R^bOH$ is allowed to react with the 7-amino compound [II] or a salt or ester thereof after isolation from the reaction mixture, or the reaction mixture containing a reactive derivative of the compound $R^bOH$ before isolation is allowed without being isolated to react with the 7-amino compound [II] or a salt or ester thereof. When the carboxylic acid $R^bOH$ is used in its free acid form or as a salt thereof, an appropriate condensing agent is used. As a condensing agent, a N,N'-disubstituted carbodiimide such as N,N'-dicyclohexylcarbodiimide, an azolide such as N,N'-carbonyldiimidazole and N,N'-thiocarbonyldiimidazole, a dehydrating agent such as N-ethoxycarbonyl-2-ethoxy-1,2-dihyroquinoline, phosphorus oxychloride and alkoxyacetylene, or a 2-halogenopyridinium salt such as 2-chloropyridiniummethyl iodide, 2-fluoropyridiniummethyl iodide. When any of these condensing agent is used, the reaction is supposed to proceed via a reactive derivative of the carboxylic acid $R^bOH$. The reaction is conducted generally in a solvent, and a solvent which does not interfere with the reaction is selected appropriately. Such solvents include ethers such as dioxane, tetrahydrofuran, diethyl ether, tertbutyl methyl ether, diisopropyl ether, and ethyleneglycol dimethyl ether, esters such as ethyl formate, ethyl acetate, and n-butyl acetate, halogenated hydrocarbons such as dichloromethane, chloroform, carbon tetrachloride, trichlene, and 1,2-dichloroethane, hydrocarbons such as n-hexane, benzene, and toluene, amides such as formamide, N,N-dimethylformamide, and N,N-dimethylacetamide, ketones such as acetone, methylethylketone, and methylisobutylketone, and nitriles such as acetonitrile, and propionitrile, and also dimethylsulfoxide, sulfolane, hexamethylphosphoramide, and water, which are used alone or in combination with each other. The amount of the acylating agent ($R^bOH$) is usually 1 to 5 moles, preferably 1 to 2 moles, per 1 mole of the 7-amino compound [II]. The reaction is conducted at $-80°$ to $80°$ C., preferably $-40°$ to $50°$ C., and most desirably $-30°$ to $30°$ C. The reaction time varies according to the species of the 7-amino compound [II] and the carboxylic acid $R^bOH$, the kind of the solvent (also the mixing ratio if a mixed solvent is used), the reaction temperature etc., being usually 1 minute to 72 hours, preferably 15 minutes to 3 hours. When an acid halide is used as the acylating agent, the reaction can be conducted in the presence of an acid-binding agent for removal of the hydrogen halide liberated. Such acid-binding agents include inorganic bases such as sodium carbonate, potassium carbonate, calcium carbonate, and hydrogen sodium carbonate, tertiary amines such as triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine, and N-methylmorpholine, and alkyleneoxides such as propyleneoxide, and epichlorohydrin.

By the method described above, for example, the compound [VII] described above can be synthesized. The reaction is written by the following formula.

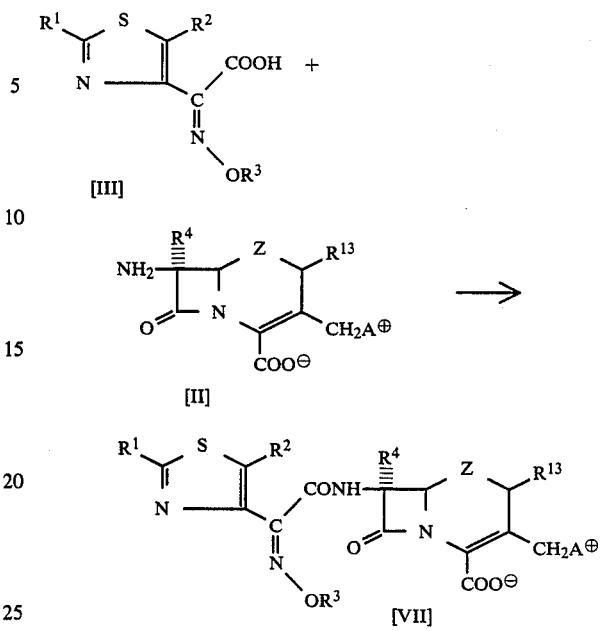

The carboxylic acid [III] can be produced easily by a known method or one analogous thereto.

(3-2): The compound [$I^b$] ($R^0=R^b$) can be synthesized by the the reaction of a compound having the general formula

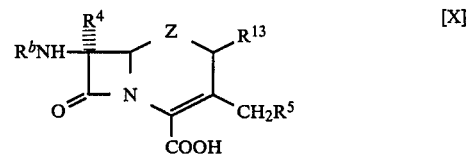

wherein, $R^b$ is an acyl group, and the other symbols are the same as described above, or a salt or an ester thereof, with a triazole compound or a salt thereof (A'). The reaction is written by the following formula.

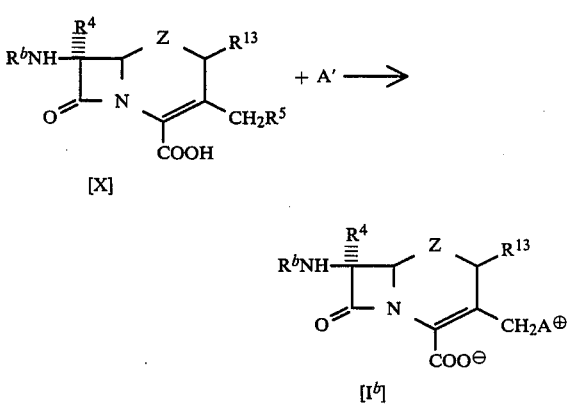

wherein, the symbol $R^b$ is an acyl group, and the symbols Z, $R^4$, $R^{13}$, $R^5$, A and A' are the same as described above. This reaction is essentially the same as that described in the Method of Production (1), consisting in the synthesis of the compound [$I^b$] ($R^0=R^b$) by the nucleophilic substitution reaction of a compound [X] or a salt or an ester thereof with a triazole compound or a salt thereof (A'). In the compound [X], $R^5$ is a hydroxyl, an acyloxy, a carbamoyloxy, a substituted carbamoyloxy group, or a halogen atom. The compound [X] is used as a free form or as a salt or an ester thereof. As the salts and esters of the compound [X], the salts and esters of the 7-amino compound [II] described in the Method of Production (3-1) are applicable. The compound [X], the salts and esters thereof can be produced easily by a known method one analogous thereto. On the other hand the triazole compound (A') is a condensed triazole which may be substituted. Here the condensed ring means the one formed by condensation of a triazole ring with a 5- or 6-membered aromatic heterocyclic ring utilizing a nitrogen atom and an adjacent carbon atom as the bridge head atoms, and this condensed ring may be condensed further with another aromatic ring or aromatic heterocyclic ring. The condensed triazole (A') which may be substituted is represented by the general formula $[A^{1'}]$, $[A^{3'}]$ or $[A^{5'}]$.

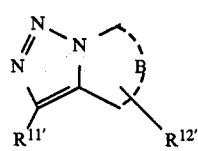

[$A^{1'}$]

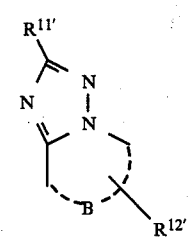

[$A^{3'}$]

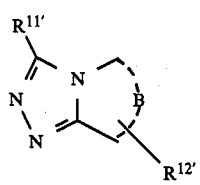

[$A^{5'}$]

A⊕ group in the desired compound $[I^b]$ ($R^0=R^b$) synthesized by the reaction of the compound [X] or a salt or ester thereof with the compound $[A^{1'}]$ is the $A^1$ group or $A^2$ group described above, the A⊕ group in the desired compound $[I^b](R^0=R^b)$ synthesized by the reaction of the compound [X] or a salt or ester thereof with the compound $[A^{3'}]$ is the $A^3$ group described above, and the A⊕ group in the desired compound $[I^b](R^0=R^b)$ synthesized by the reaction of the compound [X] or a salt or ester thereof with the compound $[A^{5'}]$ is the $A^4$ group or $A^5$ group described above. The symbol B in the formula of the condensed triazole $[A^{1'}]$, $[A^{3'}]$ and $[A^{5'}]$ means also here the same as the B in the $A^1$-$A^5$ groups described before, and therefore the compound $[A^{1'}]$ means in the concrete:

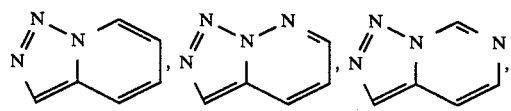

-continued

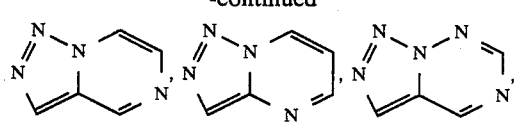

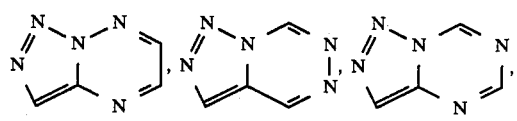

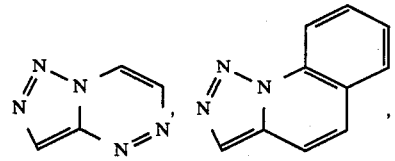

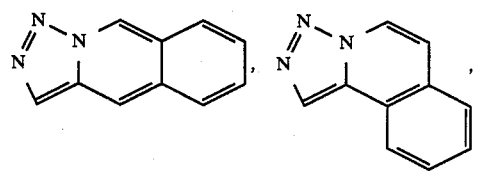

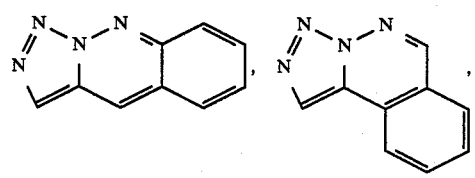

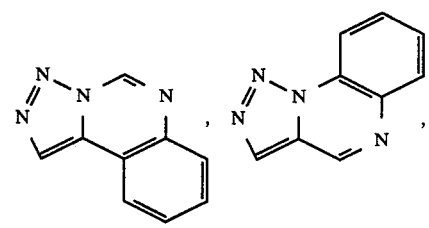

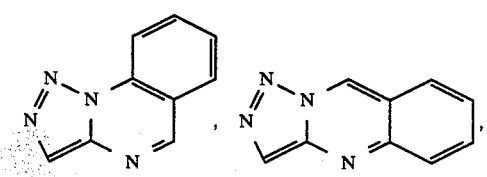

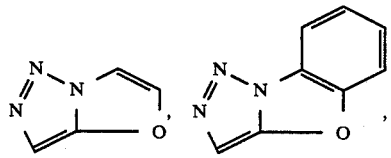

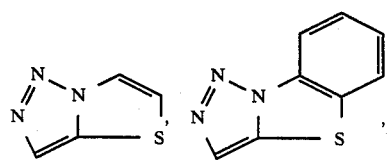

-continued and the compound [A³'] is exemplified by and the compound [A⁵'] is exemplified by

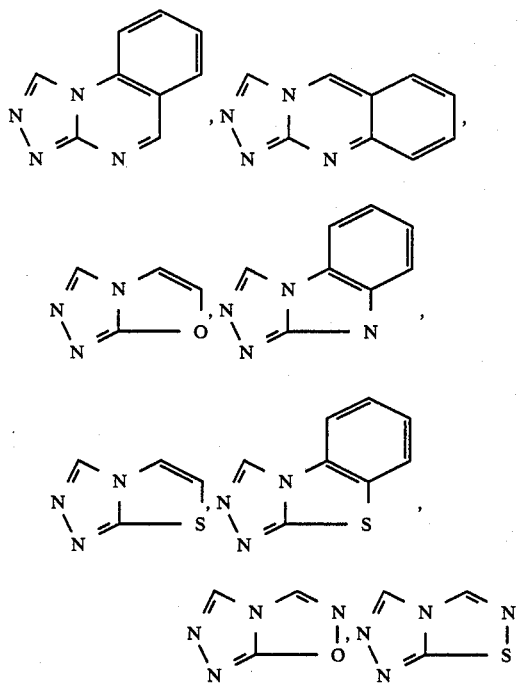

As the symbols $R^{11}$ and $R^{12'}$ on the triazole compound A', the symbols $R^{11}$ and $R^{12}$ for the group A described before are applicable respectively. The substituents $R^{11'}$ and $R^{12}$ may be further substituted. The triazole compound A' includes the salt thereof. The salts of the compound A' include inorganic acid additon salts such as hydrochlorides, hydrobromides, sulfates, nitrates, and phosphates, and organic acid addition salts such as formates, acetates, trifluoroacetates, methanesulfonates, and p-toluenesulfonates. General methods for the synthesis of triazole compounds and the salts thereof (A') are known, and these compounds can be synthesized easily by a known method described in the literatures or by a per se known method. Such literatures include, for example, "Comprehensive Heterocyclic Chemistry Volume 5 Alan R. Katritzky et al." as a comprehensive literature, and specifically the following: relating to [1,2,4]triazolo[1,5-a]pyridine, Journal of Organic Chemistry 31 (1966), 260, and Chemical and Pharmaceutical Bulletin 14 (1966), 506; relating to [1,2,4]triazolo[4,3-b]pyridine, Journal of the Chemical Society 1957, 4510 and Journal of Organic Chemistry 31 (1966), 251; relating to [1,2,4]triazolo[1,5-a]pyrimidine, Tetrahedron Letters 1973, 1677, Journal of Organic Chemistry 39(1974), 2143 and Journal of Heterocyclic Chemistry 12(1975), 107; relating to [1,2,4]triazolo[4,3-b]pyridazine, Journal of Heterocyclic Chemistry 17(1980), 1527 and Australian Journal of Chemistry, 34(1981), 1729; relating to [1,2,4]triazolo[1,5-b]pyridazine, Tetrahedron Letters, 1978, 3059, Journal of Organic Chemistry 39(1974),2143, Organic Preparations Procedure Int. 10(1978),293 and Journal of Heterocyclic Chemistry, 14(1977),1403; and relating to [1,2,3]triazolo[1,5-a]pyridine, Journal of Heterocyclic Chemistry, 12(1975),481 and Yakugaku Zasshi 101 (1981),329. The said nucleophilic substitution reaction of the compound [X] with the triazole compound (A') is a well-known reaction which is conducted usually in a solvent. As the solvent to be used for this reaction, the ethers, esters, halogenated hydrocarbons, hydrocarbons, amides, ketones, nitriles and water, which are used in the Method of Production (3-1), are applicable. Alcohols such as methanol, ethanol, n-propanol, isopropanol, ethylene glycol, and 2-methoxy ethanol are also used. In some cases where the triazole compound A' is a liquid, a large excess of the said compound A' as compared with the amount of the compound [X] (for example 10 to 200 times moles) is used so as to serve also as the solvent. In these cases, the solvents described above need not be used, or a mixed solvent consisting of one of the solvents described above and A' may be used.

(3-2-1): When $R^5$ is an acyloxy, a carbamoyloxy, or a substituted carbamoyloxy group;

Preferable solvents are water and a mixed solvent consisting of an organic solvent miscible with water and water, and preferable organic solvents miscible with water include acetone, methyl ethyl ketone, and acetonitrile. The amount of a nucleophilic reagent A' is usually 1 to 5 moles, preferably 1 to 3 moles, per 1 mole of the compound [X]. The reaction is conducted at 10° to 100° C., preferably at 30° to 80° C. The reaction time varies depending on the species of the compound [X] and the compound A', the kind of the solvent (also the mixing ratio when a mixed solvent is used), reaction temperature, etc., being usually 30 minutes to 5 days, pareferably 1 to 5 hours. The reaction is conducted advantageously at pH 2 to 8, preferably near the neutral region i.e. at pH 5 to 8. The reaction proceeds more easily in the presence of usually 2 to 30 equivalents of an iodide or a thiocyanate. Such salts include sodium iodide, potassium iodide, sodium thiocyanate, and potassium thiocyanate. In addition to the salts described above, a surface active quaternary ammonium salt such as trimethylbenzylammonium bromide, triethylbenzylammonium bromide, and triethylbenzylammonium hydroxide may promote the reaction.

(3-2-2): When $R^5$ is a hydroxyl group;

For example according to the method described in Japanese Patent Application Laid-Open (Tokkai) No. 43979/83 etc., the reaction is conducted in the presence of an organic phosphorus compound. The organic phosphorus compound used here includes o-phenylenephosphorochloridate, o-phenylenephosphorofloridate, methyl o-phenylenephosphate, ethyl o-phenylenephosphate, propyl o-phenylenephosphate, isopropyl o-phenylenephosphate, butyl o-phenylenephosphate, isobutyl o-phenylenephosphate, sec-butyl o-phenylenephosphate, cyclohexyl, o-phenylenephosphate, phenyl o-phenylenephosphate, p-chlorophenyl o-phenylenephosphate, p-acetyl o-phenylenephosphate, 2-chloroethyl o-phenylenephosphate, 2,2,2-trichloroethyl o-phenylenephosphate, ethoxycarbonylmethyl o-phenylenephosphate, carbamoylmethyl o-phenylenephosphate, 2-cyanoethyl o-phenylenephosphate, 2-methylsulfonylethyl o-phenylenephosphate, benzyl o-phenylenephosphate, 1,1-dimethyl-2-propenyl o-phenylenephosphate, 2-propenyl o-phenylenephosphate, 3-methyl-2-butenyl o-phenylenephosphate, 2-thienylmethyl o-phenylenephosphate, 2-furfurylmethyl o-phenylenephosphate, bis-o-phenylenepyrophosphate, 2-phenyl-1,3,2-benzodioxaphosphole-2-oxide(2-phenyl-2-oxo-1,3,2-benzodioxaphosphole-2-(p-chlorophenyl)-1,3,2-benzodioxaphospho-2-oxide, 2-butyl-1,3,2-benzodioxaphospho-2-oxide, 2-anilino-1,3,2-benzodioxaphosphole-2-oxide, 2-phenylthio-1,3,2-benzodioxaphosphole-2-oxide, 2-methoxy-5-methyl-1,3,2-benzodioxaphosphole-2-oxide, 2-chloro-5-ethoxycarbonyl-1,3,2- benzodioxaphosphole-2-oxide, 2-methoxy-5-ethoxycarbonyl-1,3,2-benzodioxaphosphole-2-oxide, 5-ethoxycarbonyl-2-phenyl-1,3,2-benzodioxaphosphole-2-oxide, 2,5-dichloro-1,3,2-benzodioxaphosphole-b 2-oxide, 4-chloro-2-methoxy-1,3,2-benzodioxaphosphole-2-oxide, 2-methoxy-4-methyl-1,3,2-benzodioxaphosphole-2-oxide, 2,3-naphtalenemethylphosphate, 5,6-dimethyl-2-methoxy-1,3,2-benzodioxaphosphor-2-oxide, 2,2-dihydro-4,5,6,7-tetrachloro-2,2,2-trimethoxy-1,3,2-benzodioxaphosphole, 2,2-dihydro-4,5,6,7-tetrachloro-2,2,2-triphenoxy-1,3,2-benzodioxaphosphole, 2,2-dihydro-2,2-ethylenedioxy-2-methoxy-1,3,2-benzodioxaphosphole, 2,2-dihydro-2-benzyl-2,2-dimethoxy-1,3,2-benzodioxaphosephole, 2,2-dihydro-4,5-benzo-2,2,2-trimethoxy-1,3,2-benzodioxaphosphole, 2,2-dihydro-2,2,2-triphenoxy-1,3,2-benzodioxaphosphole, 2,2-dihydro-2,2-(o-phenylenedioxy)-2-phenoxy-1,3,2-benzodioxaphosphole, 2-chloro-2,2-dihydro-2,2-(o-phenylenedioxy)-1,3,2-benzodioxaphosphole, 2,2-dihydro-2-methoxy-2,2-(o-phenylenedioxy)-1,3,2-benzodioxaphosphole, 2,2-dihydro-2,2,2-trichloro-1,3,2-benzodioxaphosphole, 9,10-phenanthrenedioxytrimethoxyphosphorus, o-phenylenephosphorochloridite, o-phenylenephosphorobromidite, o-phenylenephosphorofloridite, methyl o-phenylenephosphite, butyl o-phenylenephosphite, methoxycarbonylmethyl o-phenylenephosphite, phenyl o-phenylenephosphite, p-chloro(or p-nitro)phenyl o-phenylenephosphite, 2-phenyl-1,3,2-benzodioxaphosphole, bis-o-phenylenepyrophosphite, 2-methoxy-5-methyl-1,3,2-benzodioxaphosphole, 5-acetyl-2-phenoxy-1,3,2-benzodioxaphosphor, 9,10-phenanthrenephosphorochloridite, 2-chloro-4-methyl-1,3,2-benzodixoaphosphole, 5-ethoxycarbonyl-2-phenyl-1,3,2-benzodioxaphosphole, 2-chloro-2-thioxo-1,3,2-benzodioxaphosphole, 2-pheoxy-2-oxo-1,3,2-benzodiazaphosphor, 2-phenoxy-1,3,2-benzodioxaazaphosphole, 2,2-dihydro-2-oxo-2-methoxy-4,5-dimethyl-1,3,2-dioxaphosphole, 2,2-dihydro-2-oxo-2-chloro-4,5-dimethyl-1,3,2-dioxaphosphole, 2,2-dihydro-2-oxo-2-(1-imidazolyl)-4,5-dimethyl-1,3,2-dioxaphosphole, 2,2-dihydro-2,2-ethylenedioxy-2-methoxy-4,5-dimethyl-1,3,2-dioxaphosphole, 2,2-dihydro-2,2-dimethoxy-2-phenoxy-4,5-dimethyl-1,3,2-dioxaphosphole, 2,2-dihydro-2,2,2-trimethoxy-4,5-dimethyl-1,3,2-dioxaphosphole, 2,2-dihydro-2,2,2-triphenoxy-4,5-dimethyl-1,3,2-dixoaphosphole, 2,2-dihydro-2,2,2-triethoxy-4,5-diphenyl-1,3,2-dioxaphosphole, 2,2-dihydro-2,2,2-trimethoxy-4,5-diphenyl-1,3,2-dioxap-hosphole, 2,2-dihydro-2-oxo-2-methoxy-4,5-diphenyl-1,3,2-dioxaphosphole-2,2-dihydro-2,2,2-trimethoxy-1,3,2-dioxaphosphole, 2,2-dihydro-2,2,2-trimethoxy-4-phenyl-1,3,2-dioxaphosphole, 2,2-dihydro-2,2,2-trimethoxy-4-methyl-1,3,2-dioxaphosphole, 2,2-dihydro-2,2,2-trimethoxy-4-methyl-5-phenylcarbamoyl-1,3,2-dioxaphosphor, 2,2,4,5,6,7-hexahydro-2,2,2-trimethoxy-1,3,2-benzodioxaphosphole, 2,2'-oxybis(4,5-dimethyl-2,2-dihydro-1,3,2-dioxaphosphole), and 2,2'-oxybis(4,5-dimethyl-2,2-dihydro-1,3,2-dioxaphosphole-2-oxide). Among these, lower alkyl o-phenylenephosphates such as methyl o-phenylenephosphate and ethyl o-phenylenephosphate, and 2-phenyl-1,3,2-benzodioxaphosphole-2-oxide are preferable. The reaction may be carried out in any solvent which does not interfere with the reaction. The solvents which may preferably be used are the ethers, esters, halogenated hydrocarbons, hydrocarbons, amides, ketones and nitriles described above, which may be used separately or in combination as a mixed solvent. Good results are obtained especially when a solvent such as dichloromethane, 1,2-dichloroethane, acetonitrile, ethyl acetate, formamide, tetrahydrofuran, a mixed solvent consisting of formamide and acetonitrile, and a mixed solvent consisting of dichloromethane and acetonitrile is used. The use of dichloromethane is particularly desirable. The amount of the nucleophilic reagent A' and that of the organic phosphorus compound are 1 to 5 moles and 1 to 10 moles, respectively, per 1 mole of the compound [X], preferably 1 to 3 moles and 1 to 6 moles, respectively. The reaction is conducted usually at −50° to 100° C., preferably at −35° to 35° C. The reaction time is usually 1 minute to 15 hours, preferably 5 minutes to 2 hours. An organic base may be added to the reaction system. Such organic bases include amines such as triethylamine, tri(n-butyl)amine, di(n-butyl)amine, di(n-butyl)amine, diisobutylamine, dicyclohexylamine, or 2,6-lutidine. Preferably 1 to 5 moles of the base is added per 1 mole of the compound [X].

(3-2-3): When $R^5$ is a halogen atom;

The preferable solvents for the reaction are such ethers, esters, halogenated hydrocarbons, hydrocarbons, amides, ketones, nitriles, alcohols and water as described above. The amount of the nucleophilic reagent A' used is usually 1 to 5 moles, preferably 1 to 3 moles, per 1 mole of the compound [X]. The reaction is conducted at 0° to 80° C., preferably at 20° to 60° C. The reaction time is usually 30 minutes to 15 hours, preferably 1 to 5 hours. The reaction may be conducted in the presence of an acid-binding agent to accelerate the reaction. As such acid-binding agents, those described in the section of the Method of Production (3-1) such as inorganic bases, tertiary amines, and alkylene oxides are also here applicable, and the nucleophilic reagent A' itself may serve as the acid-binding agent. In the latter case, 2 or more moles of the compound A' is used per 1 mole of the compound [X]. The halogen atom represented by $R^5$ is chlorine, bromine or iodine, among which iodine is preferable. The compound [X] in which $R^5$ is iodine can be produced easily by the method described in Japanese Patent Application Laid-Open (Tokkai) No. 57390/83 or by a method analogous thereto.

With these methods described above, the compound [VII] or [VIII] described above can be synthesized. The reaction formula is shown in the following.

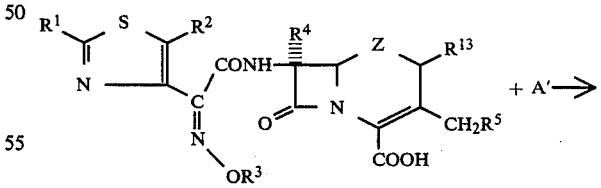

[III]

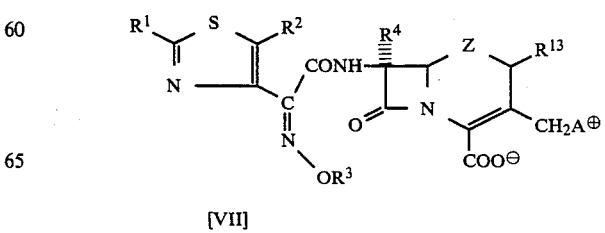

[VII]

-continued

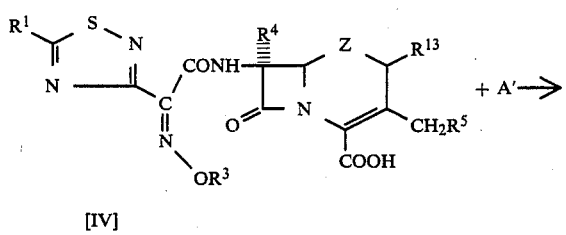

[IV]

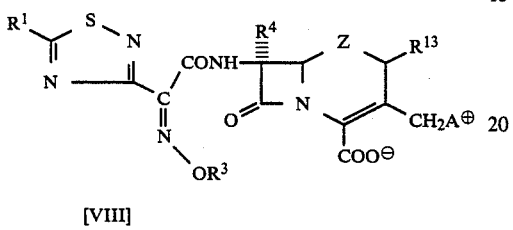

[VIII]

The compounds [III] and [IV] can be produced easily by a known method or by one analogous thereto.

The compound [IX] including the compounds [VII] and [VIII] can be produced not only by the Method of Production (3-1) or (3-2) described above but also by the Method of Production (3-3) described below. The compound [VII] can be produced nor only by the Method (3-1), (3-2), or (3-3) but also by the Method (3-4) described below. (3-3): The reaction formula is as follows.

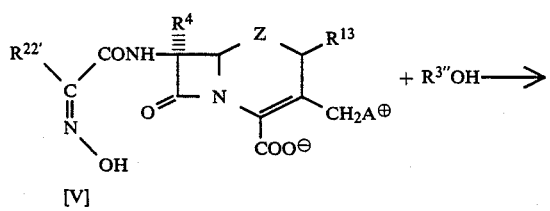

[V]

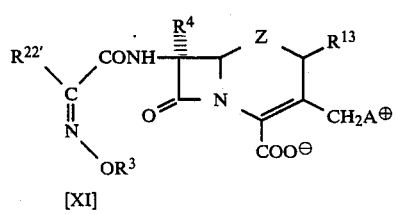

[XI]

wherein, the symbol $R^{22'}$ is a heterocyclic group which may be substituted, and the symbols Z, $R^4$, $R^{13}$, A and $R^3$ are the same as described above.

This method consists in the synthesis of the compound [XI] by the reaction of the hydroxyimino compound [V] with a compound having the general formula $R^{3''}OH$ or a reactive derivative thereof, a well-known reaction of ether formation. When $R^{22'}$ is

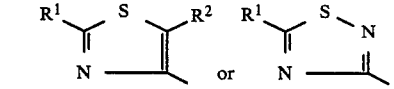

the product [XI] is the compound [VII] or [VIII]. $R^{3''}$ is a hydrocarbon residue which may be substituted, and as such hydrocarbon residues the hydrocarbon residues which may be substituted described before as $R^3$ are also here applicable. $R^{3''}OH$ may be used as it is or in a form of its reactive derivative. The reactive derivative of $R^{3''}OH$ means the derivative of $R^{3''}OH$ having a group which is removed together with the hydrogen atom of hydroxyimino compound [V], i.e. a compound represented by the general formula $R^{3''}Y$. The group Y which is removed together with the hydrogen atom is a halogen atom, a sulfo group, monosubstituted sulfonyloxy group, etc. The halogen atoms include chlorine, bromine and iodine. The monosubstituted sulfonyloxy groups include $C_{1-6}$alkylsulfonyloxy groups such as a methanesulfonyloxy, ethanesulfonyloxy, benzenesulfonyloxy, and p-toluenesulfonyloxy, and $C_{6-10}$arylsulfonyloxy group. Particularly when $C_{1-4}$alkylether derivatives of the compound [V] are produced, in addition to the reactive derivatives described above, $C_{1-4}$diazoalkane such as diazomethane and diazoethane, $diC_{1-4}$alkyl sulfate such as dimethyl sulfate and diethyl sulfate can be used.

The compound [V] can be synthesized by the acylation described in the Method of Production (3-1) or by the nucleophilic substitution described in the Method of Production (3-2). That is, the reactions are written by the following formulas.

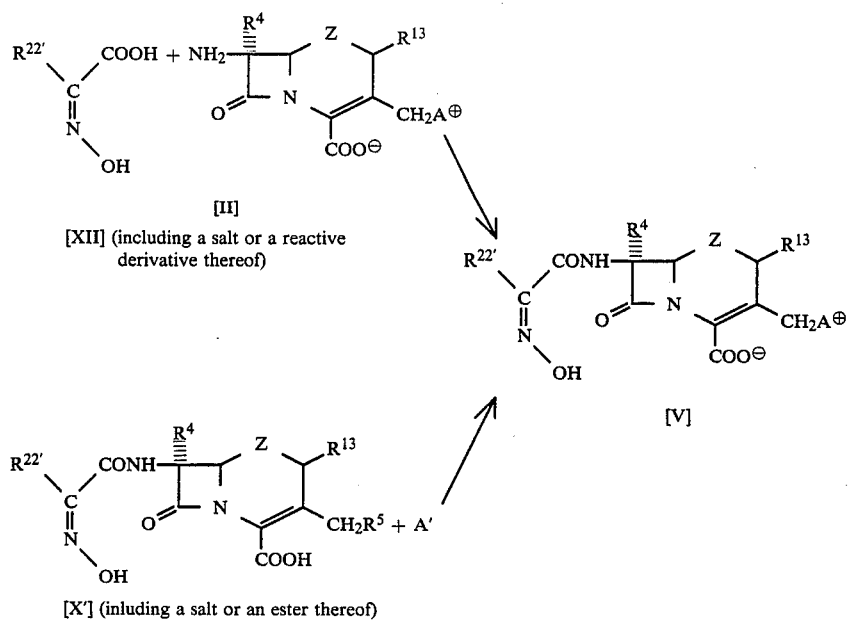

[XII] (including a salt or a reactive derivative thereof)

[X'] (including a salt or an ester thereof)

Also the starting compounds [XII] and [X'] can be synthesized easily by a known method or a per se known method. Also the compound $R^{3''}$OH and the reactive derivatives thereof can be synthesized easily by a known method or one analogous thereto.

(3-3-1): When $R^{3''}$OH is used;

The compound [XI] is synthesized by the reaction with a hydroxyimino compound [V] in the presence of an appropriate dehydrating agent. The dehydrating agents used for this purpose include phosphorus oxychloride, thionyl chloride, dialkyl azodicarbonate (which is used usually in the presence of phosphine), and N,N'-dicyclohexylcarbodiimide, among which diethyl azodicarbonate in the presence of triphenylphosphine is preferable. The reaction using diethyl azodicarbonate in the presence of triphenylphosphine is usually conducted in an anhydrous solvent such as ethers and hydrocarbons described above. One to 1.5 moles each of the compound $R^{3''}$OH, ethyl azodicarbonate and triphenylphosphine are used per 1 mol of the hydroxyimino compound [V]. The reaction takes 1 to 4 days at 0° to 50° C.

(3-3-2) When $R^{3''}$Y is used;

The reaction of $R^{3''}$Y with the hydroximino compound [V] is a usual ether formation reaction and is preferably conducted in a solvent. As the solvents, ethers, esters, halogenated hydrocarbons, hydrocarbons, amides, ketones, nitriles, alcohols, and water or the mixed solvents described in the Method of Production (3-1) are also here applicable, among which a mixed solvent consisting of a solvent miscible with water and water (for example aqueous methanol, aqueous ethanol, aqueous acetone, and aqueous dimethylsulfoxide) is preferable. This reaction can be conducted smoothly in the presence of an appropriate base. Such bases include inorganic bases such as alkali metal salts, for example, sodium carbonate, sodium hydrogen carbonate, and potassium carbonate, and alkaline metal hydroxides, for example, sodium hydroxide and potassium hydroxide. This reaction may be conducted in a buffer solution of pH 7.5 to 8.5. One to 5 moles, preferably 1 to 3 moles of the reagent $R^{3''}$Y and 1 to 10 moles, preferably 1 to 3 moles of a base are used per 1 mole of the starting compound [V]. The reaction temperature is −30° to 100° C., preferably 0° to 80° C. The reaction time is 10 minutes to 15 hours, preferably 30 minutes to 5 hours.

(3-3-3): When $C_{1-4}$diazoalkane is used;

The reaction is conducted usually in a solution. As the solvent, ethers and hydrocarbons described above are used. The reaction proceeds when the solution of the diazoalkane compound is added to a solution of the hydroxyimino compound [V]. One to 10 moles, preferably 1 to 5 moles of the reagent is used per 1 mole of the compound [V]. The reaction is conducted at a relatively low temperature, at −50° to 20° C., preferably at −30° to 0° C. The reaction time is 1 minute to 5 hours, preferably 10 minutes to 1 hour.

(3-3-4): When $diC_{1-4}$alkyl sulfate is used;

The reaction is conducted usually in water or in a mixed solvent consisting of a solvent miscible with water and water. As the mixed solvent, the aqueous solvents described in the Method of Production (3-3-2) are also here applicable. This reaction is conducted usually in the presence of an inorganic base such as an alkali metal hydroxide, for example sodium hydroxide or potassium hydroxide. Per 1 mole of the compound [V], 0.5 to 10 moles, preferably 1 to 2 moles of the reagent is used. The reaction temperature is 20° to 100° C., preferably 50° to 100° C. The reaction time is 10 minutes to 5 hours, preferably 30 minutes to 3 hours.

(3-4): The reaction formula is as follows.

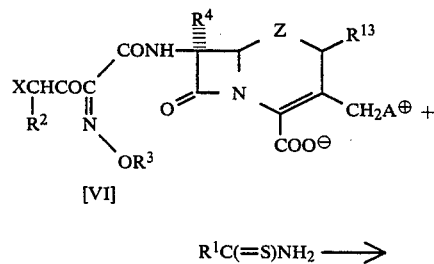

[VI]

$R^1C(=S)NH_2 \longrightarrow$

-continued

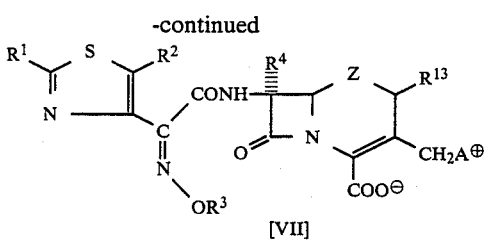

[VII]

wherein the symbols Z, $R^4$, $R^{13}$, A, $R^1$, $R^2$ and $R^3$ are the same as described above.

This is a method of synthesis of the desired compound [VII] by the reaction of the compound [VI] with thiourea or a thiourea derivative having the general formula $R^1C(=S)NH_2$. The compound [VI] is used in a free form or as a salt or an ester thereof. X in the compound [VI] is a halogen atom such as chlorine, bromine and iodine. As the salts of the compound [VI], the salts of the 7-amino compound [II] described in te Method of Prcduction (3-1) (such as incrganic base salts, ammonium salts, organic base salts, inorganic acid addition salts, and organic acid addition salts) are also here applicable. As the esters of the compound [VI], the esters of the 7-amino compound [II] described also in the Method of Production (3-1) (such as the $C_{1-6}$alkyl*, $C_{2-6}$alkenyl, $C_{3-10}$cycloalkyl, $C_{3-6}$cycloalkyl-$C_{1-6}$alkyl, $C_{6-10}$aryl*, $C_{7-12}$aralkyl*, di$C_{6-10}$aryl-methyl, tri$C_{6-10}$aryl-methyl, and $C_{2-6}$alkanoyloxy-$C_{1-6}$alkyl esters) are also here applicable. The starting compound [VI] can be easily produced by the reaction of a compound having the general formula

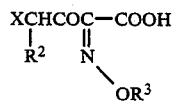

wherein the symbols are the same as desribed above, or a salt or a reactive derivative thereof, with the 7-amino compound [II] described above or a salt or an ester thereof, by a method in accordance with the method described in the Method of Production (3-1) The compound having the general formula

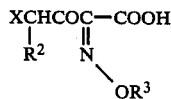

or a reactive derivative thereof can be produced easily by a known procedure or one analogous thereto. The reaction of the compound [VI] or with a salt or ester thereof with $R^1C(S=)NH_2$ is conducted usually in a solvent. As the solvent, an ether such as dioxane, tetrahydrofuran, or diethyl ether, an alcohol such as methanol, ethanol, or n-propanol, and an amide such as dimethylformamide or dimethylacetamide is used. The amount of thiourea or a derivative thereof $R^1C(S=)NH_2$ is usually 1 to 5 moles, preferably 1 to 3 moles, per 1 mole of the compound [VI]. The reaction is conducted at 0° to 100° C., preferably at 20° to 60° C. The reaction time is usually 30 minutes to 15 hours, preferably 1 to 5 hours.

When a hydroxyimino group (or a substituted hydroxyimino group) is present in the substituent $R^b$ in the compound [$I^b$] produced by the Methods of Production (3-1) to (3-4) (for example, the compounds [VII] and [VIII]), the compound [$I^b$] is sometimes obtained as a mixture of syn[Z]- and anti[E]-isomers. For the isolation of the desired syn-isomer, a known procedure or one analogous thereto can be applied. Such methods include fractionation by taking advantage of the difference in solubility or crystalinity, chromatographic separation, and separation by taking advantage of the difference in rate of hydrolysis of the ester derivatives. Method of Production (4): Method of synthesis of the compound [I] ($R^0=R^c$; $R^c$ is an amino protective group). For example, the compound can be synthesized by the reaction of the 7-amino compound [II]([I], $R^0$=a hydrogen atom) or a salt or an ester thereof synthesized in the Method of Production (1), with an amino protective agent. The method is described in the concrete in the following.

(4-1): When $R^c$ is a phthaloyl group;

As the phthaloylating agent, phthalic anhydride, or a phthaloyl halide (e.g. phthaloyl chloride) or the like is used. The reaction is conducted usually in a solvent; when a phthaloyl halide is used, an anhydrous solvent is preferable. As the solvent, ethers such as dioxane, tetrahydrofuran, diethyl ether, tert-butyl methyl ether, diisopropyl ether, and ethyleneglycol dimethyl ether, halogenated hydrocarbons such as dichloroethane, chloroform, carbon tetrachloride, trichlene, and 1,2-dichloroethane, and hydrocarbons such as n-hexane, benzene, and toluene are frequently used, which may be used singly or in combination as a mixed solvent. The amount of the agent is usually 1 to 3 moles, preferably 1 to 1.5 moles, per 1 mole of the 7-amino compound [II]. The reaction can be conducted at −80° to 150° C., but at 30° to 150° C., preferably at 70° to 140° C., when phthalic anhydride is used, and at −80° to 100° C., preferably at −30° to 80° C., when a phthaloyl halide is used. The reaction time varies depending upon the species of the 7-amino compound [II] and the phthaloylating agent, the kind of the solvent, the reaction temperature, etc., being usually 1 minute to 24 hours, preferably 10 minutes to 4 hours.

When phthalic anhydride is used, the reaction can sometimes be conducted more effectively by removing the water formed in the reaction out of the reaction system. When a phthaloyl halide is used, the reaction can be conducted in the presence of an acid-binding agent to remove the liberated hydrogen halide out of the reaction system. Such acid-binding agents include inorganic bases such as sodium carbonate, potassium carbonate, calcium carbonate, and sodium hydrogen carbonate, tertiary amines such as triethylamine, tri(n-propyl)amine, tri(n-butyl)amine, diisopropylethylamine, cyclohexylmethylamine, pyridine, lutidine, γ-collidine, N,N-dimethylaniline, N-methylpiperidine, N-methylpyrrolidine, and N-methylmorpholine, and alkylene oxides such as propylene oxide and epichlorohydrin.

(4-2) When $R^c$ is a substituted oxycarbonyl group (e.g. benzyloxycarbonyl or the like above-mentioned);

As the substituted oxycarbonylating agent, for example, substituted oxycarbonyl halides (the halogen means chlorine, bromine, iodine, etc.), substituted oxycarbonyl azides, substituted oxycarbonic anhydrides, substituted oxycarbonyl sulfides, substituted oxycarbonyl azolides (the azoles include imidazole, N-methylimidazole, triazole, 2-thiooxazolidine, 2-oxooxazolidine, etc.) are used. The reaction is conducted usually in a solvent, and an anhydrous solvent is preferable. Such solvents include ethers such as dioxane, tetrahydrofuran, diethyl ether, tert-butyl methyl ether, diisopropyl ether, and ethylene glycol dimethyl ether, halogenated hydrocarbons such as dichloroethane, chloroform, carbon tetrachloride, trichlene, and 1,2-dichloroethane, nitriles such as acetonitrile, alcohols such as methanol, ethanol, propanol, and butanol, hydrocarbons such as n-hexane, benzene, and toluene, amides such as dimethylformamide, dimethylacetamide, and hexamethylphosphoramido, and sulfoxides such as dimethylsulfoxide are frequently used, which are used singly or in combination as a mixed solvent. The amount of the substituted oxycarbonylating agent is usually 1 to 5 moles, preferably 1 to 2 moles, per 1 moe of the 7-amino compound [II]. The reaction is conducted at $-80°$ to $80°$ C., preferably at $-40°$ to $50°$ C., most desirably at $-30°$ to $30°$ C. The reaction time varies depending on the species of the 7-amino compound [II] and the substituted oxycarbonylating agent, the kind of the solvent, the reaction temperature, etc., being usually 1 minute to 48 hours, preferably 10 minutes to 2 hours. When a substituted oxycarbonyl halide is used as the substituted oxycarbonylating agent, the reaction can be conducted in the presence of an acid-binding agent to remove the liberated hydrogen halide from the reaction system. Such acid-binding agents include inorganic bases such as sodium carbonate, potassium carbonate, calcium carbonate, and sodium hydrogen carbonate, tertiary amines such as triethylamine, tri(n-propyl)amine, tri(n-butyl)amine, diisopropylethylamine, cyclohexyldimethylamine, pyridine, lutidine, $\gamma$-collidine, N,N-dimethylaniline, N-methylpiperidine, N-methylpyrrolidine, and N-methylmorpholine, and alkylene oxides such as propylene oxide and epichlorohydrin.

(4-3): When $R^c$ is a $C_{6-10}$aryl*methyl, di$C_{6-10}$aryl*methyl, or tri$C_{6-10}$aryl*methyl group;

As the agents, usually the corresponding halides, that is, $C_{6-10}$aryl*methyl halides, di$C_{6-10}$aryl*methyl halides, and tri$C_{6-10}$aryl*methyl halides are used, and among those halides, the corresponding iodides, bromides, and chlorides are preferable. As the solvent, those described in the Method of Production (4-2) are also here applicable. The amount of the agent is usually 1 to 3 moles, preferably 1 to 1.5 moles, per 1 mole of the 7-amino compound [II]. The reaction is conducted at $-80°$ to $100°$ C., preferably at $-30°$ to $70°$ C. The reaction time varies depending on the species of the 7-amino compound [II] and the halides to react, the kind of the solvent, the reaction temperature etc., being usually 1 minute to 24 hours, preferably 10 minutes to 5 hours. This reaction can be conducted in the presence of an acid-binding agent for removal of hydrogen halide formed as a by-product from the reaction system. As such an acid-binding agent, those described in the Method or Production (4-1) are also here applicable. After the reaction of the Methods of Production (1)-(4) described above, the desired compound [I] of this invention can be obtained by removal of the protective group, followed by purification, if necessary. In the following the method of removal of the protective group and the purification are explained.

Method of Removal of the Protective Group: As described above, in the fields of $\beta$-lactams and peptides, the amino protective groups have been extensively investigated and the methods of protection have been established. Also the methods of removal of the amino protective groups have been established, and the known procedure for removal of the amino protective groups is applicable also to the present invention. For example, a monohalogenoacetyl group (such as chloroacetyl or bromoacetyl) can be removed with thiourea, an alkoxycarbonyl group (such as methoxycarbonyl, ethoxycarbonyl or tert-butoxycarbonyl) with an acid (such as hydrochloric acid), an aralkyloxycarbonyl group (such as benzyloxycarbonyl, p-methylbenzyloxycarbonyl, or p-nitrobenzyloxycarbonyl) by catalytic reduction, and the 2,2,2-trichloroethoxycarbonyl group with zinc and an acid (such as acetic acid). When the compound [I] is esterified, the ester residue can be also removed by a per se known procedure or a method in accordance with the known procedure. For example, the 2-methylsufonyl ethyl ester group can be removed with alkali, an aralkyl ester group (such as a benzyl, p-methoxybenzyl, or p-nitrobenzyl ester) with an acid (such as trifluoroacetic acid) or by catalytic reduction, the 2,2,2-trichloroethyl ester group with zinc and an acid (such as acetic acid), and a silyl ester group (such as a trimethylsilyl, or tert-butyl dimethylsilyl ester) with water alone.

Method of Purification of the Compound [I]: The compound [I] produced in the reaction mixture by the method described in detail in the Methods of Production (1)-(4), if necessary, followed by the removal of the protective group by the method described above, can be purifed by a known procedure such as extraction, column chromatography, precipitation, recrystallization, etc. When the compound [I] isolated is not a salt or an ester, the product can be converted into desired pharmaceutically acceptable salt or a desired metabolically unstable nontoxic ester by a known procedure or one analogous thereto.

The sulfoxides ([I], Z=S→O) of cephem compounds ([I], Z=S) are obtained by oxidation of the compounds ([I], Z=S). Such oxidation is well known. Oxidizing agents suitable for the oxidation of the sulfur atom in the cephem ring include oxygen, peracids, hydroperoxides, and hydrogen peroxide, and peroxides can be produced by mixing of an acid with a peroxide during the reaction As the peracids, peracetic acid, perbenzoic acid, and p-chloroperbenzoic acid are frequently used. The reaction is conducted usually in a solvent. The solvents used for this reaction include ethers such as dioxane and tetrahydrofuran, halogenated hydrocarbons such as dichloromethane, chloroform and chlorobenzene, organic acids such as formic acid, acetic acid and trifluoroacetic acid, and amides such as dimethylformamide and dimethylacetamide. The reaction is conducted at $-20°$ to $80°$ C., preferably at a temperature as low as possible, desirably at $-20°$ to $20°$ C. Oxidation of a cephem compound ([I], Z=S) is generally known to produce predominantly a sulfoxide of S-configuration. R-Sulfoxides and S-sulfoxides are fractionated by taking advantage of the difference in their solubility or mobility in chromatographic separation. The oxidation reactions described above to produce sulfoxides may be conducted prior to the reactions described in the Methods of Production (1) to (4), or subsequently to the reactions (1) to (4).

The compound [I] of this invention including the compound [VII] and [VIII], as the known penicillins and cephalosporins, is able to be administered intramuscularly or intravenously in the form of injections. Especially the metabolically unstable intoxic esters are able to be administered orally in the form of capsules, tablets, and granules. The dose is 0.5 to 80 mg/day/kg body weight of a man or an animal infected with a pathogenic bacteria described above, more desirably 1 to 20 mg/day/kg, given 3 or 4 times a day. On account of their antibacterial properties, the compounds of this invention may be used as an antiinfective agent or a disinfectant for removing bacteria including the aforementioned bacteria from surgical instruments or hospital rooms.

For example, surgical instruments are put for 2 days in an aqueous solution containing 1000 μg/ml of any compound of this invention for the above purpose. However, in the case where esters of this invention are employed for this purpose, the corresponding deesterified are put put into use. Excipients used for injections include distilled water and physiological saline, and when the compound is used in the form of capsules, powders, granules, and tablets, the compound is mixed with a known pharmaceutically acceptable excipient (such as starch, lactose, sucrose, calcium carbonate, and calcium phosphate), a binder (such as starch, gum arabic, carboxymethylcellulose, hydroxypropylcellulose, and crystalline cellulose), a lubricant (such as magnesium stearate and talc), or a disintegrating agent (such as carboxymethylcellulose calcium and talc).

This invention is illustrated in further detail in the following Reference Examples and Working Examples, but these are only examples and do not limit this invention. Modifications within the scope of this invention are permissible.

Elution in a column chromatography in the Reference Examples and Working Examples was carried out while monitoring with TLC (Thin Layer Chromatography). In the TLC monitoring, TLC plate used was $BOF_{254}$ manufactured by Merck Co., the solvent used for the development was the same to the one used for elution in the column chromatography, and UV detector was employed for detection. As the silica gel for the column, Kieselgel 60 manufactured by Merck Co. (230–400 mesh) was used. "Sephadex" is a product of Pharmacia Fine Chemicals Co. XAD-II resin is a product of Rohm & Haas Co. NMR spectra were measured by using tetramethylsilane as an internal or external standard with a spectrometer XL-100 (100 MHz), EM360 (60 MHz), EM390 (90 MHz) or $T_{60}$ (60 MHz) type, and all δ values were expressed in ppm. The value shown in ( ) for a mixed solvent indicates the mixing ratio by volume of the constituent solvents. The percentage (%) for a solution indicates grams (g) in 100 ml of the solution. The symbols used in the Reference Examples and Examples mean as follows.

s: singlet
d: doublet
t: triplet
q: quartet
ABq: AB type quartet
d.d: double doublet
m: multiplet
br.: broad
J: coupling constant
Hz: Herz
mg: milligram
g: gram
ml: milliliter
l: liter
%: percent
DMSO: dimethyl sulfoxide
$D_2O$: deuterium oxide
$CDCl_3$: deuterochloroform
$CD_3CN$: deuteroacetonitrile

REFERENCE EXAMPLE 1

7β-[2-(2-Chloroacetamidothiazol-4-yl)-2(Z)-methoxyiminoacetamido]-3-(3-oxobutyryloxymethyl)-3-cephem-4-carboxylic acid 7β-Amino-3-(3-oxobutyryloxymethyl)-3-cephem-4-carboxylic acid, 157 g, is suspended in a mixture consisting of 500 ml of tetrahydrofuran and 500 ml of water, and to this, 141 g of sodium hydrogen carbonate is added in small portions with stirring. With stirring at 5° C., 150 g of 2-(2-chloroacetamidothiazol-4-yl)-2(Z)-methoxyiminoacetylchloride hydrochloride is added over 20 minutes, and the reaction mixture is stirred for further 1 hour at the same temperature. After completion of the reaction, the pH is adjusted to 3.0 with 10% hydrochloric acid, and the reaction mixture is extracted twice with 1 liter each of a mixture of ethyl acetate-tetrahydrofuran (1:1). The extract is dried over anhydrous magnesium sulfate, the solvent is evaporated off under reduced pressure to leave colorless powder, which is washed with 200 ml of ethyl acetate and filtered, to give 253 g of the desired compound.

Elemental analysis for $C_{20}H_{20}ClN_5O_9S_2$, Calc. (%): C, 41.85; H, 3.51; N, 12.20.
Found (%): C, 41.39; H, 3.57; N, 11.94.
IR spectrum $\nu_{max}^{KBr}$ cm$^{-1}$; 1780, 1740, 1700, 1655, 1540, 1410.
NMR spectrum ($d_6$-DMSO) δ: 2.20(3H,s), 3.45 and 3.68(2H, ABq,J=18 Hz), 3.65(2H,s), 3.92(3H,s), 4.38(2H,s), 4.79 and 5.09(2H, ABq, J=13 Hz), 5.18(1H,d, J=5 Hz), 5.85(1H,d.d, J=5 Hz and 8 Hz), 7.44(1H,s), 9.66(1H,d,J=8 Hz), 12.85(1H, br.s).

REFERENCE EXAMPLE 2

7β-[2-(2-Aminothiazol-4-yl)-2(Z)-methoxyiminoacetamido]-3-(3-oxobutyryloxymethyl)-3-cephem-4-carboxylic acid.

7β-2-[2-(Chloroacetamidothiazol-4-yl)-2(Z)-methoxyiminoacetamido]-3-cephem-4-carboxylic acid, 150 g, is dissolved in 500 ml of a mixture of tetrahydrofuran-water (1:1), to which 51 g of sodium N-methydithiocarbamate is added, and the mixture is stirred at 20° C. for 3 hours. To the reaction mixture 200 ml of ethyl acetate is added, the organic phase is removed, and the aqueous layer is adjusted to pH 4 with 10% hydrochloric acid, to give an oil. This oil is extracted with 1 liter of a mixed solvent of tetrahydrofuran-ethyl acetate (1:1), and the aqueous phase is extracted with 200 ml of 1-butanol. The extract is dried over anhydrous sodium sulfate, and the solvent is evaporated off under reduced pressure. The residue is treated with 200 ml of ethyl acetate with stirring, and the deposited crystals are collected by filtration giving 90 g of the desired compound.

Elemental analysis for $C_{18}H_{19}N_5O_8S_2$, Calc. (%): C,42.19; H,4.30; N,13.55. Found (%): C,41.94; H,4.11; N,13.59.
IR spectrum $\nu_{max}^{KBr}$ cm$^{-1}$: 1770, 1710, 1620, 1520.
NMR spectrum ($d_6$-DMSO) δ: 2.20(3H,s), 3.43 and 3.65(2H, ABq, J=18 Hz), 3.63(2H,s), 3.86(3H,s), 4.78 and 5.06(2H, ABq, J=13 Hz), 5.14(1H,d,J=5 Hz), 5.79(1H,d.d,J=5 Hz and 8 Hz), 6.73(1H,s), 7.17(2H,br.s), 9.56(1H,d,J=8 Hz).

REFERENCE EXAMPLE 3

7β-[2-(2-Aminothiazol-4-yl)-2(Z)-ethoxyiminoacetamido]-3-(3-oxobutyryloxymethyl)-3-cephem-4-carboxylic acid.

2-(2-Aminothiazol-4-yl)-2(Z)-ethoxyiminoacetic acid, 23 g, is dissolved in 100 ml of dimethylformamide, to which 15 g of 1-hydroxybenzotriazole and 20.6 g of dicyclohexylcarbodiimide are added, and the mixture is stirred at 20° C. for 1.5 hours. Insoluble substances are filtered off, and the filtrate is added to 100 ml of dimethylformamide solution of 31 g of 7β-amino-3-(3-oxobutyryloxymethyl)-3-cephem-4-carboxylic acid and 28 ml of triethylamine under ice cooling. The reaction mixture is stirred at 20° C. for 3 hours, to which 500 ml of diethyl ether is added and the deposited solid is collected by filtration. The solid is dissolved in 100 ml of water and the pH is adjusted to 3.0 with 10% of hydrochloric acid, followed by extraction twice with 200 ml each of methyl ethyl ketone. The extract is washed with water and dried over anhydrous sodium sulfate, and the solvent is evaporated under reduced pressure. The resulting solid is washed with ethyl acetate to give 31 g of the desired compound.

IR spectrum $\nu_{max}^{KBr}$ cm$^{-1}$: 1780, 1720, 1660.

NMR spectrum (d$_6$-DMSO) δ: 1.30(3H,t,J=7.5 Hz), 2.25(3H,s), 3.45–3.65(4H,m), 4.20(2H,q,J=7.5 Hz), 4.70 and 5.10(2H, ABq,J=18 Hz), 5.25(2H,d,J=5 Hz), 5.90(1H,d.d,J=5 Hz and 8 Hz), 6.90(1H,s), 7.20–7.80(2H,br.s), 9.80(1H,d,J=7.5 Hz).

REFERENCE EXAMPLE 4

7β-[2-(5-tert-Butoxycarbonylamino-1,2,4-thiadiazol-3-yl)-2(Z)-methoxyiminoacetamido]-3-(3-oxobutyryloxymethyl)-3-cephem-4-carboxylic acid.

2-(5-tert-Butoxycarbonylamino-1,2,4-thiadiazol-3-yl)-2(Z)-methoxyiminoacetic acid, 302 mg, is added to 4 ml of dichloromethane, followed by addition of 208 mg of phosphorus pentachloride, and the mixture is stirred for 15 minutes under ice cooling. The solvent is evaporated off under reduced pressure, and the residue is treated with hexane, which is then evaporated to dryness again under reduced pressure. The residue is dissolved in dichloromethane. This solution is added to a solution of 300 mg of 7β-amino-3-(3-oxobutyryloxymethyl)-3-cephem-4-carboxylic acid and 0.6 ml of triethylamine in 5 ml of dimethylacetamide, and the mixture stirred under ice cooling for 30 minutes. The reaction mixture is treated with 1 g of phosphoric acid dissolved in 10 ml of water, and the mixture extracted with methyl ethyl ketone (10 ml). The extract is washed with water and dried over magnesium sulphate. The solvent is evaporated off under reduced pressure and the residue is treated with ethyl acetate and the solvent is evaporated off again to give 390 mg of the desired compound.

IR spectrum $\nu_{max}^{KBr}$ cm$^{-1}$: 2980, 2940, 1780, 1715, 1540, 1370, 1245, 1150, 1040, 855.

NMR spectrum (d$_6$-DMSO) δ: 1.56(9H,s), 2.20(3H,s), 3.43 and 3.70(2H, ABq, J=18 Hz), 3.65(2H,s), 4.00(3H,s), 4.80 and 5.12(2H,ABq,J=12 Hz), 5.18(1H,d,J=4.5 Hz), 5.88(1H,d.d,J=9 Hz and 4.5 Hz), 9.63(1H,d,J=9 Hz).

REFERENCE EXAMPLE 5

(i) 7β-[2-(5-Chloro-2-chloroacetamidothiazol-4-yl)-2(Z)-methoxyiminoacetamido]-3-(3-oxobutyryloxymethyl)-3-cephem-4-carboxylic acid.

2-(5-Chloro-2-chloroacetamidothiazol-4-yl)-2(Z)-methoxyiminoacetic acid, 2.39 g, is added to 50 ml of dichloromethane, to which 2.13 g of phosphorus pentachloride is added under cooling at −5° to −8° C., and the mixture is stirred for 45 minutes. To the reaction mixture, 150 ml in total of hexane is added in 30 ml portions, and the resulting dark-colored oil is separated and washed with hexane to give a crude corresponding chloride. To a solution of 2.06 g of sodium bicarbonate in 15 ml of water, a solution of 2.06 g of 7β-amino-3-(3-oxobutyryloxymethyl)-3-cephem-4-carboxylic acid in 15 ml of tetrahydrofuran is added followed by addition of the chloride described above while keeping the inner temperature at 0°–3° C. After completion of the addition the mixture is stirred at 5° C. or below for 1 hour and at room temperature for another 1 hour, to which 50 ml of methyl ethyl ketone is added and the mixture is acidified with concentrated hydrochloric acid. The organic layer is separated. The aqueous layer is extracted with methyl ethyl ketone. The organic layer and the extract are combined and dried over anhydrous sodium sulfate, and the solvent is evaporated off under reduced pressure to give 2.94 g of the desired compound as a pale orange powder.

NMR spectrum (CDCl$_3$+d$_6$-DMSO) δ: 2.23(3H,s), 3.24–3.73 (2H,m), 3.50(2H,s), 4.01(3H,s), 4.21(2H,s), 4.91 and 5.18 (2H,ABq, J=13 Hz), 5.05(1H,d,J=4.5 Hz), 5.88(1H,d.d,J=4.5 Hz and 9 Hz), 6.43(2H,br.s), 8.79(1H,d,J=9 Hz).

(ii) 7β-[2-(2-Amino-5-chlorothiazol-4-yl)-2(Z)-methoxyiminoacetamido]-3-(3-oxobutyryloxymethyl)-3-cephem-4-carboxylic acid.

7β-[2-(5-Chloro-2-chloroacetamidothiazol-4-yl)-2(Z)-methoxyiminoacetamido]-3-(3-oxobutyryloxymethyl)-3-cepehm-4-carboxylic acid, 2.94 g, is dissolved in a mixture of 13 ml of water and 13 ml of tetrahydrofuran, to which 1.15 g in total of N-methyldithiocarbamate in 3 portions is added with stirring at room temperature for 3 hours. To the reaction mixture, ethyl acetate is added and the ethyl acetate layer is separated and discarded. The aqueous layer is acidified and extracted with 200 ml of methyl ethyl ketone. The extract is washed with saline and dried over anhydrous sodium sulfate, and the solvent is evaporated off to give 2.28 g of the desired compound.

NMR spectrum: (d$_6$-DMSO+CDCl$_3$) δ: 2.21(3H,s), 3.3–3.75 (2H,m), 3.57(2H,s), 3.90(2H,s), 4.81 and 5.09(2H,ABq,J=13 Hz), 5.07(1H, d ,J=5 Hz), 5.77(1H,d.d,J=5 Hz and 9 Hz), 7.10(2H, br.s), 9.46(1H,d,J=9 Hz).

REFERENCE EXAMPLE 6

7β-[2-(2-Aminothiazol-4-yl)-2(Z)-(1-tert-butoxycarbonyl-1-methylethoxyimino)acetamido]-3-(3-oxobutyryloxymethyl)-3-cephem-4-carboxylic acid.

2-(2-Aminothiazol-4-yl)-2(Z)-(1-tert-butoxycarbonyl-1-methylethoxyimino)acetic acid, 12 g, is dissolved in 60 ml of N,N-dimethylformamide, to which 5.86 g of 1-hydroxybenzotriazole and 7.5 g of dicyclohexylcarbodiimide are added and the mixture stirred at room temperature for 30 minutes. Insoluble substances are filtered off, and the filtrate is added to 30 ml of N,N-dimethylformamide suspension of 11 g of 7β-amino-3-(3-oxobutyryloxymethyl)-3-cephem-4-carboxylic acid and 10 ml of triethylamine, and the mixture stirred room temperature for 6 hours. Insoluble substances are filtered off, and the filtrate is treated with 1.3 l of diethyl ether and the mixture stirred for a while and the supernatant ether layer is removed. The residue is dissolved in water and the pH of the mixture is adjusted to 3-4 with 1N-HCl, followed by extraction with methyl ethyl ketone (1 liter). The organic layer is washed with saturated aqueous sodium chloride and dried over anhydrous magnesium sulfate. The solvent is evaporated off under reduced pressure, and the residue is solidified by addition of n-hexane, and the resultant powder is collected by filtration to give 18.7 g of the desired compound.

IR spectrum $\nu_{max}^{KBr}$ cm$^{-1}$: 1780, 1720, 1660, 1530.

NMR spectrum (d$_6$-DMSO) δ: 1.42(s,15H), 2.20(s,3H), 3.4–3.7 (m,4H), 4.70 and 5.10(ABq,J=14 Hz,2H), 5.19(d,J=4.5 Hz,1H), 5.82(d.d,J=4.5 Hz and 8 Hz,1H), 6.73(s,1H), 7.19(br.s,2H), 9.29(d,J=8 Hz,1H).

REFERENCE EXAMPLE 7

7β-[2-(5-Amino-1,2,4-thiadiazol-3-yl)-2(Z)-methoxyiminoacetamido]-3-(3-oxobutyryloxymethyl)-3-cephem-4-carboxylic acid.

To 50 ml of trifluoroacetic acid which is being stirred under ice cooling, 13 g of 7-[2-(5-tert-butyloxycarbonylamino-1,2,4-thiadiazol-3-yl)2(Z)-methoxyiminoacetamido-3-(3-oxobutyryloxymethyl)-3-cephem-4-carboxylic acid is added. After stirring for further 30 minutes without cooling, trifluoroacetic acid is evaporated under reduced pressure. The residue is treated with 100 ml of ethyl acetate, and the ethyl acetate is evaporated under reduced pressure. To the residue, 100 ml of ethyl ether is added. The resulting powder is filtered to give 10 g of the desired compound.

IR spectrum $\nu_{max}^{KBr}$ cm$^{-1}$: 1770, 1730, 1700, 1680, 1520, 1400, 1180, 1140, 1040.

NMR spectrum (d$_6$-DMSO) δ: 2.20(3H,s), 3.43 and 3.64(2H,ABq, J=18 Hz), 3.64(2H,s), 3.93(3H,s), 4.77 and 5.07(2H,ABq, J=12 Hz), 5.14(1H,d,J=4.8 Hz), 5.82(1H,d.d,J=4.8 Hz and 8 Hz), 8.00–9.00(2H,br.s), 9.53(1H,d,J=8 Hz).

REFERENCE EXAMPLE 8

Triethylamine salt of 7β-(tert-butoxycarbonylamino)-3-hydroxymethyl-3-cephem-4-carboxylic acid.

7β-Amino-3-hydroxymethyl-3-cephem--carboxylic acid, 2.37 g, is suspended in 15 ml of water, to which 3 ml of triethylamine is added with stirring under ice cooling, followed by addition of 4.5 g of di-tert-butyl dicarbonate and 15 ml of dioxane. After stirring at room temperature for 16 hours, 2.18 g of di-tert-butyl dicarbonate and 1.4 ml of triethylamine are added further. After stirring at room temperature further for 16 hours, the reaction mixture is treated with water and ethyl acetate, and the aqueous layer is separated. The separated aqueous layer is cooled to 0° C., adjusted to pH 2 with dilute hydrochloric acid, and extracted with ethyl acetate. The extract is washed with aqueous sodium chloride soln., dried over anhydrous magnesium sulfate, and poured into a cooled solution of 2.9 ml of triethylamine in 50 ml of dichloromethane. The solvent is evaporated under reduced pressure, and the residue is dried in a desiccator, to give 3.18 g of the desired compound as a yellow foam.

IR spectrum $\nu_{max}^{KBr}$ cm$^{-1}$: 3300(br.), 1770, 1710, 1600.

NMR spectrum (d$_6$-DMSO) δ: 1.13(9H,t), 1.39(9H,s), 2.93(6H, q,J=7 Hz), 3.38(2H,ABq,J=18 Hz), 4.08(2H,ABq,J=12 Hz), 4.87 (1H,d,J=5 Hz), 5.26(1H,d.d,J=5 Hz,9 Hz), 7.74(1H,d,J=9 Hz).

REFERENCE EXAMPLE 9

7β-[2-(2-Aminothiazol-4-yl)-2(Z)-methoxyiminoacetamido]-3-hydroxymethyl-3-cephem-4-carboxylic acid. 7β-Amino-3-hydroxymethyl-3-cephem-4-carboxylic acid, 16.97 g, is suspended in a mixture of 400 ml of water and 400 ml of tetrahydrofuran, to which 27.72 g of sodium hydrogen carbonate is added with stirring under ice cooling. Then 29.4 g of 2-(2-chloroacetamidothiazol-4-yl)-2(Z)-methoxyiminoacetyl chloride hydrochloride is added in small portions and stirred for 30 minutes. To the reaction mixture 150 ml of water and 200 ml of ethyl acetate are added and the aqueous layer is separated, and then brought to pH 7 with 1N hydrochloric acid under ice cooling. To this, with stirring at room temperature, 18.9 g of sodium N-methyldithiocarbamate is added in small portions and stirred for further 3 hours. The reaction mixture is washed with 300 ml of ethyl acetate, concentrated to 70 ml and purified by column chromatography (on 1 liter of XAD-2, eluted with water). The eluate is concentrated to 100 ml and brought to pH 2.5 with 4N hydrochloric acid under ice cooling, and the deposited crystals are collected by filtration. The crystals are washed successively with 100 ml of water, 50 ml of ethyl acetate, and 50 ml of tetrahydrofuran, and dried under reduced pressure to give 19.3 g of the desired compound.

m.p. 200°–210° C. (with decomposition).

Elemental analysis for $C_{14}H_{15}N_5O_6S_2 \cdot \frac{1}{2}H_2O$, Calc. (%): C,39.81; H,3.82; N,16.58. Found (%): C,39.73; H,3.74: N,16.39.

IR spectrum $\nu_{max}^{KBr}$ cm$^{-1}$: 3330, 3250, 2930, 1760, 1655.

NMR spectrum (d$_6$-DMSO) δ: 3.55(2H,s), 3.84(3H,s), 4,25(2H,s), 5.08(1H,d,J=5 Hz), 5.75(1H,d.d,J=5 Hz,8 Hz), 6.73(1H,s), 7.16 (2H,s), 9.55(1H,d,J=8 Hz).

Tri(n-butyl)amine, 185 mg, is dissolved in 15 ml of methanol and the solution is cooled to −20° C., to which 422 mg of the crystals described above is added with stirring. The methanol is evaporated off under reduced pressure, and the residue is treated with dry dichloromethane and the solvent is evaporated again. Drying the residue in a desiccator under reduced pressure gives the tri(n-butylamine salt of the desired compound.

REFERENCE EXAMPLE 10

7-Ethoxycarbonylmethylthio-5-methyl-[1,2,4]triazolo[1,5-a]pyrimidine.

Ethyl thioglycollate, 1.2 g, is dissolved in 30 ml of dry ethanol, to which 400 mg of sodium hydride (60% in an oil) is added under cooling with ice water and stirred for 10 minutes. Then 1.7 g of 7-chloro-5-methyl-[1,2,4]triazolo[1,5-a]pyrimidine and 10 ml of dry dichloromethane are added and stirred for 16 hours. To the reaction mixture, water and dichloromethane are added and the organic layer is separated. The separated organic layer is washed with saline and dried over anhydrous potassium carbonate. The solvent is evaporated under reduced pressure and the residue is purified by column chromatography [on 40 g of silica gel, developed and eluted with ethyl acetate] to give 2.2 g of the desired compound as a colorless powder.

Elemental analysis for $C_{10}H_{12}N_4O_2S$, Calcd. (%): C, 47.61; H, 4.79; N, 22.21 Found (%): C, 47.65; H, 4.73; N, 22.19.

NMR spectrum (CDCl$_3$) δ:1.27 (3H,t), 2.67(3H,s), 3.97(2H,s), 4.24(2H(2H,q,J=7 Hz), 6.90(1H,s), 8.42(1H,s).

REFERENCE EXAMPLE 11

7-Methoxy-5-methyl-[1,2,4]triazolo[1,5-a]pyrimidine.

A 28% methanol solution of sodium methoxide, 2.52 g, is diluted with 50 ml of dry methanol To this, 2.00 g of 7-chloro-5-methyl-[1,2,4]triazolo[1,5-a]pyrimidine is added at room temperature and stirred for 30 minutes. The solvent is evaporated under reduced pressure and the residue is treated with water and extracted twice with dichloromethane. The combined extract is washed with saline and dried over anhydrous potassium carbonate. Evaporation of the solvent under reduced pressure gives 1.69 g of the desired compound as colorless crystals.

Elemental analysis for $C_7H_8N_4O$, Calcd. (%): C,51.21; H,4.91; N,34.13. Found (%): C,51.22; H,4.98; N,34.05.

IR spectrum $\nu_{max}^{KBr}$ cm$^{-1}$: 3130, 1635, 1626.

NMR spectrum (CDCl$_3$) δ: 2.67(3H,s), 4.24(3H,s), 6.33(1H,s), 8.38(1H,s).

REFERENCE EXAMPLE 12

6-Ethoxycarbonylmethylthio-[1,2,4]triazolo[4,3-b]pyridazine.

Ethyl thioglycollate, 1.2 g, is dissolved in 30 ml of dry ethanol, to which 400 mg of sodium hydride (60% in an oil) is added under cooling with ice water and the mixture stirred for 10 minutes. Then 1.55 g of 6-chloro-[1,2,4]triazolo[4,3-b]pyridazine is added and stirred at room temperature for 67 hours. The reaction mixture is treated with water and extracted twice with chloroform. The combined extract is washed with saline and dried over anhydrous potassium carbonate. The solvent is evaporated under reduced pressure, and the residue is purified by column chromatogaraphy (on 40 g of silica gel, developed and eluted with ethyl acetate), to give 1.93 g of the desired compound as colorless crystals of m.p. 130°–133° C.

Elemental analysis for $C_9H_{10}N_4O_2S$, Calcd. (%): C,45.37; H,4.23; N,23.51. Found (%): C,45.45; H,4.25; N,23.71.

IR spectrum $\nu_{max}^{KBr}$ cm$^{-1}$: 3140, 3090, 3035, 2985, 2925, 1720.

NMR spectrum (CDCl$_3$) δ: 1.39(3H,t,J=7.5 Hz), 4.28(2H,s), 4.54(2H,q,J=7.5 Hz), 7.44(1H,d,J=10 Hz), 8.49(1H,d,J=10 Hz), 9,57(1H,s).

REFERENCE EXAMPLE 13

6-(2-Hydroxyethylthio)-[1,2,4]triazolo[4,3-b]pyridazine.

The desired compound is obtained in a way similar to that in Reference Example 12.

IR spectrum $\nu_{max}^{KBr}$ cm$^{-1}$: 3235, 3035, 3080, 2880.

NMR spectrum (CDCl$_3$-d$_6$-DMSO) δ: 3.47(2H,t,J=6 Hz), 3.95(2H,d.t,J=5.5 Hz,6 Hz), 4.97(1H,t,J=5.5 Hz), 7.08(1H,d, J=10 Hz), 8.07(1H,d,J=10 Hz), 9.22(1H,s).

REFERENCE EXAMPLE 14

7-[2-(5-Amino-1,2,4-thiadiazol-3-yl)-2(Z)-methoxyiminoacetamido-3-hydroxymethyl-3-cephem-4-carboxylic acid tributylamine salt

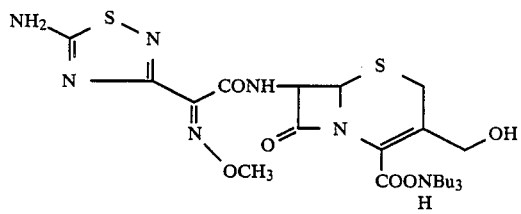

(1) 7-Amino-3-acetoxymethyl-3-cephem-4-carboxylic acid (5.44 g) is dissolved in 40 ml of 1N NaOH with stirring under ice-cooling and the solution is stirred at 0° to 5° C. for an hour. To this, 40 ml of acetone and 5.2 g of 2-(5-amino-1,2,4-thiadiazol-3-yl)-2(Z)-methoxyiminoacetyl chloride hydrochloride are added at the same temperature and the resulting solution is stirred at the same temperature for an hour. The acetone is evaporated off under reduced pressure and the residue is chromatographed on a column of MCI gel CHP 20P (Mitubishi Chemical Ind. Ltd.) using water as eluent. Fractions containing the desired product are combined and concentrated under reduced pressure and the residue is lyophilized giving 4.3 g of a sodium salt of the title compound.

NMR spectrum (d$_6$-DMSO) δ: 3.90(3H,s), 3.83 & 4.21(2H, ABq, J=13 Hz), 4.90(1H,d,J=4.5 Hz), 5.59(1H,d.d,J=9 Hz & 4.5 Hz), 8.11(2H,br.s), 9.42(1H,d,J=9 Hz).

(2) The sodium salt (3.1 g) is dissolved in 20 ml of water, and the solution is acidified under ice-cooling with conc. hydrochloric acid. The mixture obtained is extracted with a mixture of tetrahydrofuran-methyl ethyl betone (1:1) and, the organic layer combined is washed with a saturated aqueous NaCl solution and dried over anhydrous magnesium sulfate. After removal of the MgSO$_4$ by filtration, tributylamine (2 ml) is added to the filtrate. The solvent is then removed by evaporation under reduced pressure. Ethyl ether (10 ml) is added to the residue and the solidified material is pulverized and collected by filtration giving 4.5 g of the title compound as a pale yellow powder.

NMR spectrum (d$_6$-DMSO)δ: 0,91(9H,t,J-7 Hz), 1.1–1.9(12H,m), 2.8–3.1(6H,m), 3.47(2H,br.s), 3.92(3H,s), 4.18(2H,br.s), 5.02(1H,d,J=4.5 Hz), 5.71(1H,d.d,J=4.5 Hz & 9 Hz), 8.13(2H, br.s), 9.48(1H,d,J=9 Hz).

REFERENCE EXAMPLE 15

6-Dimethylamino[1,2,4]triazolo[1,5-b]pyridazine.

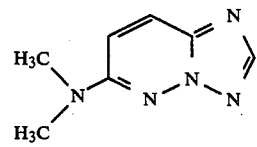

6-Chloro[1,2,4]triazolo[1,5-b]pyridazine (0.9 g) is dissolved in 10 ml of ethanol, to which 10 ml of a 7.2% solution of dimethylamine in ethanol is added. The mixture is stirred at room temperature for 24 hours. After the solvent is evaporated off under reduced pressure, the residue is dissolved in methylene chloride, washed with water and a saturated aqueous solution of sodium chloride, and dried over magnesium sulfate.

The solvent is evaporated off under reduced pressure to give 0.82 g of the titled compound as a white crystal.

NMR spectrum (CDCl$_3$)δ: 3.17 (6H, s), 7.04 (1H, d, J=10 Hz), 7.84 (1H, d, J=10 Hz), 8.20 (1H, s).

REFERENCE EXAMPLE 16

6-methyl[1,2,4]triazolo[1,5-b]pyridazine.

The titled compound is produced with the use of 3-amino-6-methylpyridazine in accordance with the method described in the Journal of Organic Chemistry 39 (1974), 2143 S. Polanc et al.

NMR spectrum (CDCl$_3$)δ: 2.70 (3H, s), 7.29 (1H, d, J=10 Hz), 8.05 (1H, d, J=10 Hz), 8.43 (1H, s)

EXAMPLE 1

7β-[2-(2-Aminothiazol-4-yl)-2(Z)-methoxyiminoacetamido]-3-[(5-methyl-[1,2,4]triazolo[1,5-a]pyridinium-1-yl)methyl]-3-cephem-4-carboxylate.

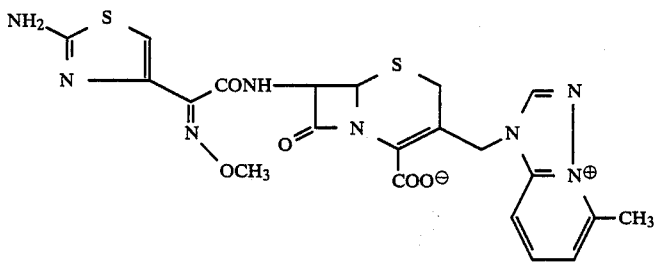

7β-[2-2-Aminothiazol-4-yl)-2(Z)-methoxyiminoacetamido]-3-(3-oxobutyryloxymethyl)-3-cephem-4-carboxylic acid, 1.8 g, 5-methyl-[1,2,4]triazolo[1,5-a]pyridine, 1.34 g, and sodium iodide, 2.2 g, are dissolved in 40 ml of 50% aqueous acetonitrile, and the solution is stirred at 50°-60° C. for 2 hours. After cooling, the reaction mixture is subjected to column chromatography on silica gel with acetone and then with aqueous acetone. The fractions containing the desired compound are combined and concentrated under reduced pressure. The residue is subjected to column chromatography on MCI gel CHP20P (manufactured by Mitsubishi Chemical Industries Ltd., 150–300μ) with water and then with aqueous alcohol. The fractions containing the desired compound are combined and concentrated under reduced pressure. The residue is lyophilized to give the desired compound.

IR spectrum $\nu_{max}^{KBr}$cm$^{-1}$:1770, 1670, 1610, 1530.

NMR spectrum (d$_6$-DMSO)δ: 2.86(3H,s), 3.11(2H×½, a half of ABq,J=18 Hz), 3.80(3H,s), 4.95(1H,d,J=4.5 Hz), 5.30 and 5.52(2H,ABq,J=14 Hz), 5.60(1H,d.d,J=4.5 Hz,J=8 Hz), 6.68(1H, s), 7.13(2H,br.s), 7.52–7.80(1H,m), 8.12–8.42(1H,m), 8.62–8.88 (1H,m), 9.45(1H,d,J=8 Hz), 9.80(1H,s).

Elemental analysis for C$_{21}$H$_{20}$N$_8$O$_5$S$_2$.9/2H$_2$O, Calcd. (%): C,41.37; H,4.79; N,18.38. Found (%): C,41.45; H,4.93; N,17.77.

EXAMPLE 2

7β-[2-(2-Aminothiazol-4-yl)-2(Z)-methoxyiminoacetamido]-3-[([1,2,4]triazolo[1,5-a]pyridinium--1-yl)methyl]-3-cephem-4-carboxylate.

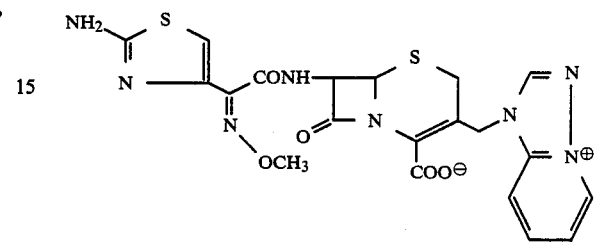

7β(2-(2-Aminothiazole-4-yl)-2(Z)-methoxyiminoacetamido]-3-(3-oxobutyryloxymethyl)-3-cephem-4-carboxylic acid and [1,2,4]triazolo[1,5-a]pyridine are treated in a way analogous to that in Example 1 to yield the desired compound.

IR spectrum $\nu_{max}^{KBr}$cm$^{-1}$: 1770, 1670, 1650, 1610, 1535.

NMR spectrum (d$_6$-DMSO-D$_2$O)δ: 3.00 and 3.34(2H,ABq,J=18 Hz), 3.83(3H,s), 5.00(1H,d,J=4.5 Hz), 5.5–5.25(2H,m), 5.63(1H,d, J=4.5 Hz), 6.69(1H,s), 7.6–7.9(1H,m), 8.2–8.5(1H,m), 8.7–8.9(1H,m), 9.29(1H, d,J=7 Hz), 9.67(1H,s).

Elemental analysis for C$_{20}$H$_{18}$N$_8$O$_5$S$_2$.5H$_2$O, Calcd. (%): C,39.73; H,4.67; N,18.53. Found (%): C,39.81; H,4.18; N,18.57.

EXAMPLE 3

7β-[2-(2-Aminothiazol-4-yl)-2(Z)-methoxyiminoacetamido]-2-[(6-methyl-[1,2,4]triazolo[1,5-a]pyridinium-1yl)methyl]-3-cephem-4-carboxylate.

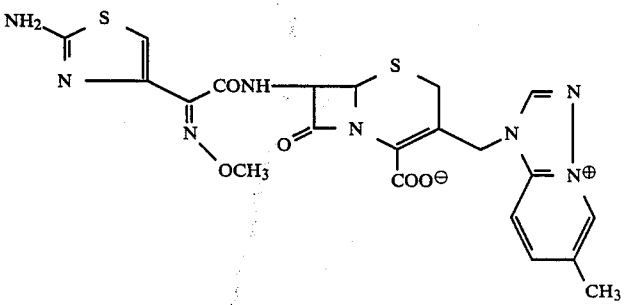

7β-[2-(2-Aminothiazol-4-yl)-2(Z)-methoxyiminoacetamido]-3-(3-oxobutyryloxymethyl)-3-cephem-4-carboxylic acid and 6-methyl-[1,2,4]triazolo[1,5-a]pyridine are treated by the same procedure as that in Example 1 to yield the desired compound.

IR spectrum $\nu_{max}^{KBr}$cm$^{-1}$:1770, 1670, 1610, 1535.

NMR spectrum (d$_6$-DMSO)δ: 2.38(3H,s), 3.09(2H×½, a half of ABq, J=18 Hz), 3.80(3H,s), 4.99(1H,d,J=4.5 Hz), 5.25 and 5.48(2H,ABq,J=14 Hz), 5.61(1H,d.d,J=4.5 Hz,J=8 Hz), 6.68(1H,s), 7.14(2H,br.s), 8.21(1H,d,J=9 Hz), 8.82(1H,d,J=9 Hz), 9.21(1H, s), 9.46(1H,d,J=8 Hz), 9.79(1H,s).

Elemental analysis for C$_{21}$H$_{20}$N$_8$O$_5$S$_2$.9/2H$_2$O, Calcd. (%): C,41.37; H,4.79; N,18.38. Found (%): C,40.92; H,4.75; N,18.55.

EXAMPLE 4

7β-[2-(2-Aminothiazol-4-yl)2-(Z)-methoxyiminoacetamido]-3-[(7-methyl-[1,2,4]triazolo[1,5-a]pyridinium-1-yl)methyl]-3-cephem-4-carboxylate.

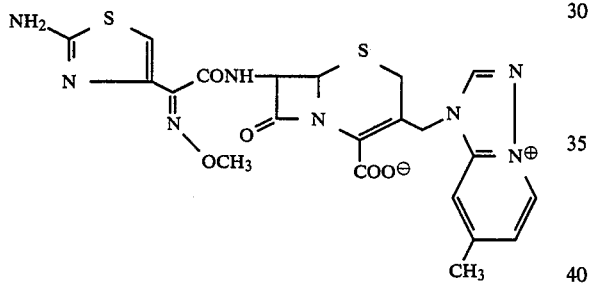

7β-[2-(2-Aminothiazol-4-yl)-2(Z)-methoxyiminoacetamido]-3-(3-oxobutyryloxymethyl)-3-cephem-4-carboxylic acid and 7-methyl-[1,2,4]triazolo[1,5-a]pyridine are treated by the same procedure as that in Example 1 to yield the desired compound.

IR spectrum $\nu_{max}^{KBr}$cm$^{-1}$:1770, 1670, 1620, 1530.

NMR spectrum (d$_6$-DMSO)δ: 2.63(3H,s), 3.17(2H×½, a half of ABq,J=18 Hz), 3.81(3H,s), 5.01(1H,d,J=4.5 Hz), 5.1-5.5(2H,m), 5.61(2H,d.d,J=4.5 Hz,J=8 Hz), 6.70(1H,s), 7.16(2H,br.s), 7.52-7.72(1H,m), 8.6-8.78(1H,m), 9.01(1H,d,J=7 Hz), 9.48(1H,d,J=8 Hz), 9.72(1H,s).

Elemental analysis for C$_{21}$H$_{20}$N$_8$O$_5$S$_2$.5H$_2$O, Calcd. (%): C,40.77; H,4.89; N,18.11. Found (%): C,40.98; H,4.94; N,18.30.

EXAMPLE 5

7β-[2-(2-Aminothiazol-4-yl)-2(Z)-methoxyiminoacetamido]-3-[(8-methyl-[1,2,4]triazolo[1,5-a]pyridinium-1-yl)methyl]-3-cephem-4-carboxylate.

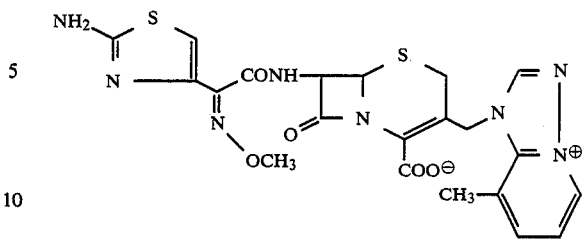

7β-[2-(2-Aminothiazol-4-yl)-2(Z)-methoxyiminoacetamido]-2-(3-oxobutyryloxymethyl)-3-cephem-4-carboxylic acid and 8-methyl-[1,2,4]triazolo[1,5-a]pyridine are treated by the same procedure as that in Example 1, to yield the desired compound.

IR spectrum $\nu_{max}^{KBr}$cm$^{-1}$: 1770, 1670, 1620, 1535.

Elemental analysis for C$_{21}$H$_{20}$N$_8$O$_5$S$_2$.5H$_2$O, Calcd. (%): C,40.77; H,4.89; N,18.11. Found (%): C,40.87; H,5.11; N,18.09.

EXAMPLE 6

7β-[2-(2-Aminothiazol-4-yl)-2(Z)-methoxyiminoacetamido]-3-[((1,2,4]triazolo[4,3-a]pyridinium-1-yl)methyl]-3-cephem-4-carboxylate.

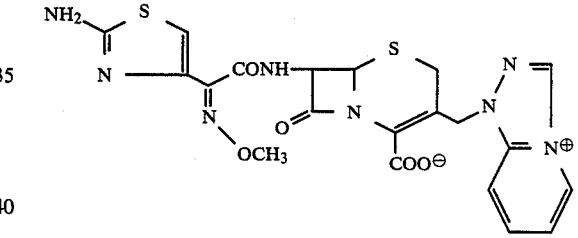

7β-[2-(2-Aminothiazol-4-yl)-2(Z)-methoxyiminoacetamido]-3-(3-oxobutyryloxymethyl)-3-cephem-4-carboxylic acid and [1,2,4]triazolo[4,3-a]pyridine are treated in a analogous way to that in Example 1, to yield the desired compound.

IR spectrum $\nu_{max}^{KBr}$cm$^{-1}$: 1770, 1670, 1615, 1525.

NMR spectrum (d$_6$-DMSO)δ: 3.17 and 3.45 (2H, ABq, J=18 Hz), 3.80(3H,s), 4.96(1H,d,J=4.5 Hz), 5.45 and 5.86(2H,ABq, J=15 Hz), 5.60(1H,d.d,J=4.5 Hz,J=8 Hz), 6.67(1H,s), 7.13(2H, br.s), 7.46-7.73(1H,m), 8.0-8.35(1H,m), 8.85-9.14(2H,m), 9.45(1H,d,J=8 Hz), 9.83(1H,s).

Elemental analysis for C$_{20}$H$_{18}$N$_8$O$_5$S$_2$.7/2H$_2$O, Calcd. (%): C,41.59; H,4.36; N,18.40. Found (%): C,41.74; H,4.46; N,19.10.

EXAMPLE 7

7β-[2-(2-Aminothiazol-4-yl)-2(Z)-methoxyiminoacetamido]-3-[3-methyl-[1,2,4]triazolo[4,3-a]pyridinium-1and 2-yl)methyl]-3-cephem-4-carboxylate.

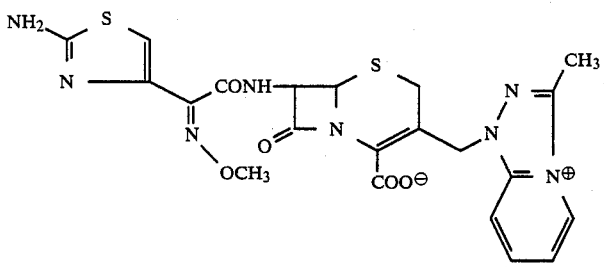

and

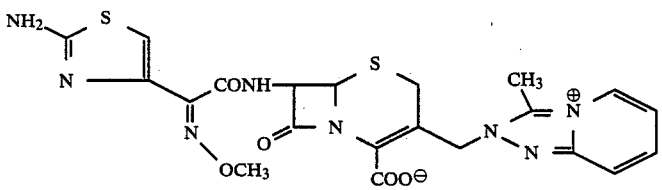

7β-[2-(2-Aminothiazol-4-yl)-2(Z)-methoxyiminoacetamido]-3-(3-oxobutyryloxymethyl)-3-cephem-4-carboxylic acid and 3-methyl-[1,2,4]triazolo[4,3-a]pyridine are treated by the same procedure as that in Example 1, to yield the desired compounds as a 2:1-mixture.

IR spectrum $\nu_{max}^{KBr}$cm$^{-1}$:1770, 1665, 1610, 1520.

NMR spectrum (d$_6$-DMSO)δ: 2.68(3H×⅓,s), 2.83(3H×⅔,s), 3.13 and 3.48(2H,ABq,J=18 Hz), 3.80(3H×⅔,s), 3.83(3H×⅓), 4.98(1H,d,J=4.5 Hz), 5.43 and 5.61(2H,ABq,J=14 Hz), 5.64(1H, d.d,J=4.5 Hz,J=8 Hz), 6.69(1H×⅔,), 6.72(1H×⅓,s), 7.16(2H,br.s), 7.3–7.76(1H,m), 7.8–8.4(1H,m), 8.64–9.14(2H, m)9.45(1H×⅔,d,J=8 Hz), 9.49(1H×⅓,d,J=8 Hz).

Elemental analysis for C$_{21}$H$_{20}$N$_8$O$_5$S$_2$.3H$_2$O, Calcd. (%): C,43.29; H,4.50; N,19.23. Found (%): C,43.48; H,4.33; N,19.30.

EXAMPLE 8

7β-[2-(2-Aminothiazol-4-yl)-2(Z)-methoxyiminoacetamido]-3-[([1,2,3]triazolo[1,5-a]pyridinium-2-yl)methyl]-3-cephem-4-carboxylate.

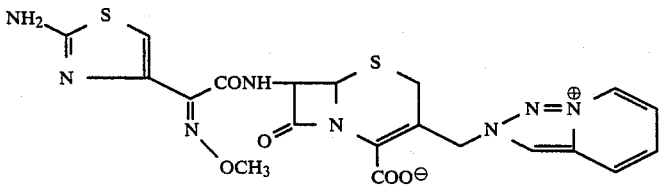

7β-[2-(2-Aminothiazol-4-yl)-2(Z)-methoxyiminoacetamido]-3-3(3-oxobutyryloxymethyl)-3-cephem-4-carboxylic acid and [1,2,3]triazolo[1,5-a]pyridine are treated by the same procedure as that in Example 1, to yield the desired compound.

IR spectrum $\nu_{max}^{KBr}$cm$^{-1}$: 1770, 1760, 1670, 1600, 1525.

NMR spectrum (d$_6$-DMSO-D$_2$O)δ: 3.15 and 3.46(2H,ABq,J=18 Hz) 3.86(3H,s), 5.02(1H, d,J=4.5 Hz), 5.3–5.72(2H,m), 5.90(1H, d,J=4.5 Hz), 6.74(1H,s), 7.06–7.27(1H,m), 7.3–7.5(1H,m), 7.84–8.06(1H,m), 8.19(1H,s), 8.94–9.08(1H,m).

Elemental analysis for C$_{20}$H$_{18}$N$_8$O$_5$S$_2$.9/2H$_2$O, Calcd. (%): C,40.33; H,4.57; N,18.81. Found (%): C,40.45; H,4.05; N,18.29.

EXAMPLE 9

7β-[2-(2-Aminothiazol-4-yl)-2(Z)-methoxyiminoacetamido]-3-[(5-methyl-[1,2,3]triazolo[1,5-a]pyridinium-2-yl)methyl]-3-cephem-4-carboxylate.

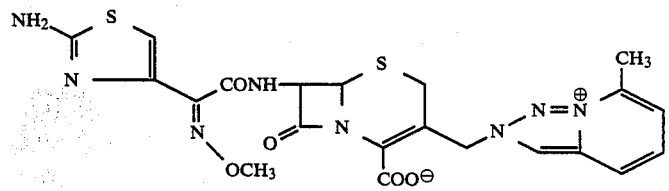

7β-[2-(2-Aminothiazol-4-yl)-2(Z)-methoxyiminoacetamido]-3-(3-oxobutyryloxymethyl)-3-cephem-4-carboxylic acid and 5-methyl[1,2,3]triazolo[1,5-a]pyridine are treated by the same procedure as that in Example 1, to yield the desired compound.

IR spectrum $\nu_{max}^{KBr}$cm$^{-1}$:1765, 1660(sh), 1605, 1520.

NMR spectrum (d$_6$-DMSO)δ: 2.84(3H,s), 3.81(3H,s), 5.03(1H,d, J=4.5 Hz), 5.27–6.00(3H,m), 6.70(1H,s), 7.14(2H,br.s), 7.55–7.95(2H,m), 8.2–8.4(2H,m), 9.43(1H,d,J=8 Hz), 9.82(1H,s).

Elemental analysis for $C_{21}H_{20}N_8O_5S_2.4H_2O$, Calcd. (%): C,41.99; H,4.70; N,18.66. Found (%): C,41.72; H,4.90; N,18.44.

EXAMPLE 10

7β-[2-(2-Amino-5-chlorothiazol-4-yl)-2(Z)-methoxyiminoacetamido]-3-[(5-methyl-[1,2,3]triazolo[1,5-a]pyridinium-2-yl)methyl]-3-cephem-4-carboxylate.

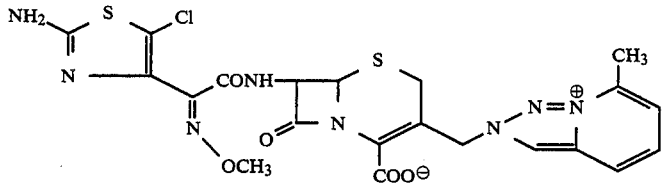

7β-[2-(2-Amino-5-chlorothiazol-4-yl)-2(Z)-methoxyiminoacetamido]-3-(3-oxobutyryloxymethyl)-3-cephem-4carboxylic acid and 5-methyl-[1,2,3]trizolo[1,5-a]pyridine are treated by the same procedure as that in Example 1, to yield the desired compound.

IR spectrum $v_{max}^{KBr}cm^{-1}$:1670, 1610, 1530.

NMR spectrum $(d_6\text{-DMSO-}D_2O)\delta$: 2.83(3H,s), 3.88(3H,s), 5.03(2H,br.s), 5.15(1H,d,J=4.5 Hz), 5.90(1H,d,J=4.5 Hz), 6.96–7.12(1H,m), 7.25–7.48(1H,m), 7.78–7.94(1H,m), 8.23(1H,s).

Elemental analysis for $C_{12}H_{19}N_8O_5S_2Cl.9/2H_2O$, Calcd. (%): C,39.16; H,4.38; N,17.40. Found (%): C,39.03; H,4.36; N,17.23.

EXAMPLE 11

7β-[2-(2-Amino-5-chlorothiazol-4-yl)-2(Z)-methoxyiminoacetamido]-3-[(5-methyl-[1,2,4]triazolo[1,5-a]pyridinium-1-yl)methyl]-3-cephem-4-carboxylate.

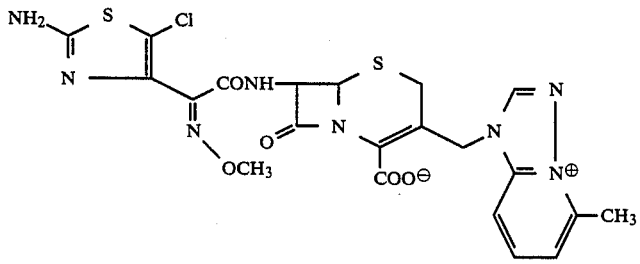

7β-[2-(2-Amino-5-chlorothiazol-4-yl)2(Z)-methoxyiminoacetamido]-b 3-(3-oxobutyryloxymethyl)-3-cephem-4-carboxylic acid and 5-methyl-[1,2,4]triazolo[1,5-a]pyridine are treated by the same procedure as that in Example 1, to yield the desired compound.

IR spectrum $v_{max}^{KBr}cm^{-1}$: 1770, 1660, 1610, 1530.

NMR spectrum $(d_6\text{-DMSO})\delta$: 2.86(3H,s), 3.09 and 3.46(2H,ABq, J=18 Hz), 3.80(3H,s), 4.97(1H,d,J=4.5 Hz), 5.30 and 5.53(2H, ABq,J=14 Hz), 5.61(1H,d.d,J=4.5 Hz,J=8 Hz), 7.31(2H,br.s), 7.55–7.80(1H,m), 8.10–8.4(1H,m), 8.78(1H,d,J=9 Hz), 9.41(1H,d,J=8 Hz), 9.78(1H,s).

Elemental analysis for $C_{21}H_{19}N_8O_5S_2Cl.4H_2O$, Calcd. (%): C,39.72; H,4.29; N,17.64. Found (%): C,39.77; H,4.32; N,17.86.

EXAMPLE 12

7β-[2-(5-Amino-1,2,4-thiadiazol-3-yl)-2(Z)-methoxyiminoacetamido]-3-[(5-methyl-[1,2,4]triazolo[1,5-a]pyridinium-1-yl)methyl]-3-cephem-4-carboxylate.

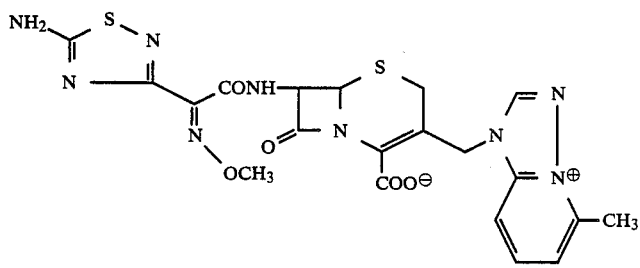

7β-[2-(5-Amino-1,2,4-thiadiazol-3-yl)-2(Z)-methoxyiminoacetamido]-3-(3-oxobutyryloxymethyl)-3-cephem-4-carboxylic acid and 5-methyl-[1,2,4]triazolo[1,5-a]pyridine are treated by the same procedure as that in Example 1, to yield the desired compound.

IR spectrum $\sigma_{max}^{KBr}cm^{-1}$: 1765, 1670, 1650, 1610, 1520.

NMR spectrum $(d_6\text{-DMSO})\delta$: 2.88(3H,s), 3.13 and 3.31(2H, ABq,J=18 Hz), 5.01(1H,d,J=4.5 Hz), 5.39(2H,br.s), 5.67(1H, d.d,J=4.5 Hz,J=8 Hz), 7.58–7.74(1H,m), 8.05–8.35(1H,m), 8.4–8.6(1H,m), 9.50(1H,J=8 Hz), 9.57(1H,s).

Elemental analysis for $C_{20}H_{19}N_9O_5S_2.5H_2O$, Calcd. (%): C,38.77; H,4.72; N,20.34. Found (%): C,39.03; H,4.78; N,20.29.

EXAMPLE 13

7β-[2-(2-Aminothiazol-4-yl)-2(Z)-ethoxyiminoacetamido]-3-[(6-methyl-[1,2,4]triazolo[1,5-a]pyridinium-1yl)methyl]-3-cephem-4-carboxylate.

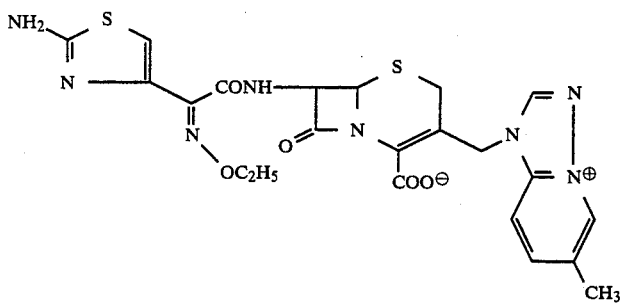

7β-[2-(2-Aminothiazol-4-yl)-2(Z)-ethoxyiminoacetamido]-3-(3-oxobutyryloxymethyl)-3-cephem-4-carboxylic acid and 6-methyl-[1,2,4]triazolo[1,5-a]pyridine are treated by the same procedure as that in Example 1, to IR spectrum $\nu_{max}^{KBr} cm^{-1}$: 1770, 1670, 1650, 1610, 1525.

NMR spectrum (d$_6$-DMSO)δ: 1.19(3H,t,J=7 Hz), 2.38(3H,s), 4.06(2H,q,J=7 Hz), 4.98(1H,d,J=4.5 Hz), 5.12–5.74(3H,m), 6.66(1H,s), 7.13(2H,br.s), 8.08–8.32(1H,m), 8.7–8.9(1H,m), 9.20(1H,br.s), 9.41(1H,d,J=8 Hz), 9.70(1H,s).

Elemental analysis for $C_{22}H_{20}N_8O_5S_2 \cdot 6H_2O$, Calcd. (%): C,40.74; H,4.97; N,17.27. Found (%): C,41.39; H,4.77; N,17.04.

EXAMPLE 14

7β-[2-(2-Aminothiazol-4-yl)-2(Z)-methoxyiminoacetamido]-3-[(3-carbamoyl-[1,2,4]triazolo[43-a]pyridinium-1yl)methyl]-3-cephem-4-carboxylate

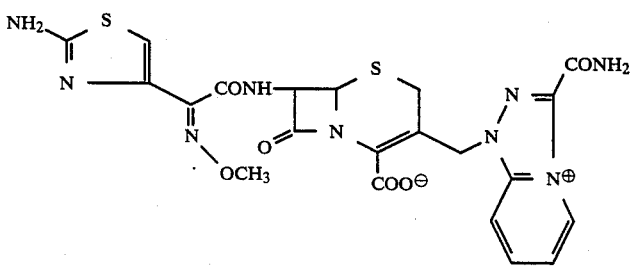

7β-[2-(2-Aminothiazol-4-yl)-2(Z)-methoxyiminoacetamido]-3-(3-oxobutyryloxymethyl)-3-cephem-4-carboxylic acid and 3-carbamoyl-[1,2,4]triazolo[4,3-a]pyridine are treated by the same procedure as that in Example 1, to yield the desired compound.

IR spectrum $\nu_{max}^{KBr} cm^{-1}$: 1760, 1680, 1650, 1530.

NMR spectrum (d$_6$-DMSO-D$_2$O)δ: 2.93 and 3.23 (2H,ABq,J=17 Hz), 3.86(3H,s), 5.00(2H,br.s), 5.16(1H,d,J=4.5 Hz), 5.37(1H, d,J=4.5 Hz), 6.65–7.14(2H,m), 6.86(1H,s), 7.80–8.32(2H,m).

Elemental analysis for $C_{21}H_{19}N_9O_6S_2 \cdot 5H_2O$, Calcd. (%): C,38.94; H,4.51; N,19.46. Found (%): C,38.91; H,4.07; N,18.94.

EXAMPLE 15

7β-[2-(2-Aminothiazol-4-yl)-2(Z)-methoxyiminoacetamido]-3-[(5,7-dimethyl-[1,2,4]triazolo[1,5-a]pyrimidinium-1-yl)methyl]-3-cephem-4-carboxylate.

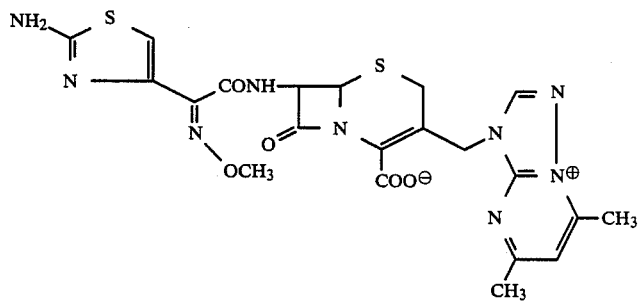

Triethylamine salt of 7β-(tert-butoxycarbonylamino)-3-hydroxymethyl-3-cephem-4-carboxylic acid, 1.296 g, and 666 mg of 5,7-dimethyl-[1,2,4]triazolo[1,5-a]pyrimidine are dissolved in 60 ml of dry dichloromethane, and the solution cooled to −30° C. To this, 1.392 g of 2-phenyl-2-oxo-1,3,2-benzo-dioxaphosphor is added. The reaction mixture is stirred so that the temperature is allowed to rise gradually up to 10° C. in 3 hours. The reaction mixture is diluted with 30 ml of dichloromethane, washed successively with a 5% aqueous solution of potassium hydrogen sulfate, water and saturated saline, and dried over anhydrous magnesium sulfate. The solvent is evaporated off under reduced pressure. The residue is purified by column chromatography (on 450 g of silica gel, developed and eluted with acetonitrile and aqueous acetonitrile) and the eluate lyophilized, to give 333 mg of 7β-(tertbutoxycarbonylamino)-3-[(5,7-dimethyl-[1,2,4]triazolo[1,5-a]pyrimidinium-1-yl)methyl]-3-cephem-4-carboxylate as a pale yellow powder. To 311 mg of this product, 1 ml of anisole and 10 ml of trifluoroacetic acid are added and the mixture is stirred at room temperature for 1 hour. The trifluoroacetic acid is evaporated off under reduced pressure, and the residue is treated with 20 ml of water. The mixture is adjusted to pH 7.5 by addition of an aqueous solution of sodium hydrogen carbonate under ice cooling. To this, 245 mg of S-(2-benzothiazolyl) 2-(2-aminothiazol-4-yl)-2(Z)-methoxyiminoacetic acid thioester and 20 ml of tetrahydrofuran are added and the mixture is stirred at room temperature for 21 hours. The same amount of the thioester described above is supplemented and the mixture is stirred further at room temperature for 24 hours. The reaction mixture is washed with ether, concentrated under reduced pressure, and purified by column chromatography (on 100 ml of XAD-2, developed and eluted with water and 10% ethanol). The eluate is concentrated to 3 ml under reduced pressure, to which 80 ml of acetone is added and the mixture is kept in a refrigerator, and the doposited powder is collected by filtration. The powder is washed with acetone and dried to give 18 mg of the desired compound. The mother liquor is purified on Sephadex LH-20 and treated in the same way, to give further 55 mg of the desired compound as a powder.

IR spectrum $\nu_{max}^{KBr}$cm$^{-1}$: 3420, 1772, 1640, 1610.

NMR spectrum (d$_6$-DMSO)δ: 2.79(3H,s), 2.86(3H,s), 3.79(3H,s), 5.07(1H,d,J=5 Hz), 5.13(2H,ABq,J=15 Hz), 5.65(1H, d.d,J=5 Hz,J=7 Hz), 6.70(1H,s), 7.81(1H,s), 10.07(1H,s).

Elemental analysis for $C_{21}H_{21}N_9O_5S_2y/2H_2O$, Calcd. (%): C,41.58; H,4.65; N,20.78. Found (%): C,41.25; H,4.35; N,20.53.

EXAMPLE 16

7β-[2-(2-Aminothiazol-4-yl)-2(Z)-methoxyiminoacetamido]-3-[([1,2,4]triazolo[1,5-a]pyrimidinium-1-yl)methyl]-3-cephem-4-carboxylate.

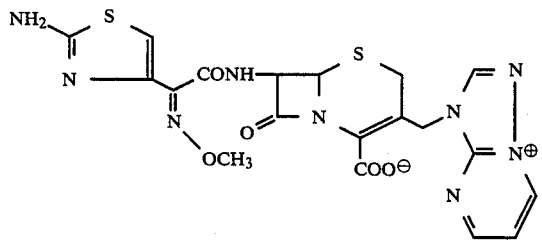

Triethylamine salt of 78-(tert-butoxycarbonylamino)-3-hydroxymethyl-3-cephem-4-carboxylic acid is allowed to react with [1,2,4]-triazolo[1,5-a]pydimidine by the same procedure as that in Example 15, to yield 7β(tert-butoxycarbonylamino)-3-[([1,2,4]-triazolo[1,5-a]pyrimidinium-1-yl)methyl]-3-cephem-4-carboxylate, which is treated with 5-(2-benzothiazolyl) 2-(2-aminothiazole-4-yl)-2(Z)methoxyiminothioacetate in a similar way to that in Example 15 to give the desired compound.

IR spectrum $\nu_{max}^{KBr}$cm$^{-1}$:3430, 1765, 1660, 1630, 1610.

NMR spectrum (d$_6$-DMSO-D$_2$O)δ: 4.06(3H,s), 5.27(1H,d,J=5 Hz), 5.48(2H,ABq,J=14 Hz), 5.88(1H,d,J=5 Hz), 7.05(1H,s), 8.02(1H,d.d,J=5 Hz,J=7 Hz), 9.43(1H,d.d,J=2 Hz,J=5 Hz), 9.60(1H,s), 9.60(1H,d.d,J=2 Hz,J=7 Hz).

EXAMPLE 17

7β-[2-(2-Aminothiazol-4-yl)-2(Z)-methoxyiminoacetamido]-3-[(2-methyl-[1,2,4]triazolo[1,5-a]pyrimidinium-1yl)methyl]-3-cephem-4-carboxylate.

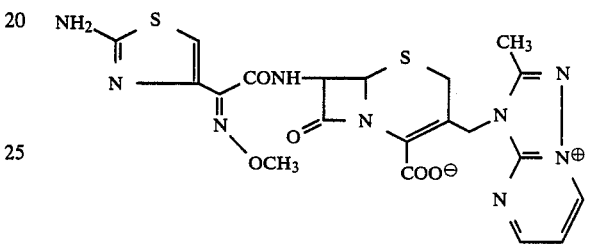

Tri(n-butyl amine salt of 7β-[2-(2-aminothiazol-4-yl)-2(Z)-methoxyiminoacetamido]-3-hydroxymethyl-3-cephem-4-carboxylic acid, 898 mg, and 604 mg of 2-methyl[1,2,4]triazolo[1,5-a]pyrimidine are dissolved in 30 ml of dry dichloromethane, and the mixture is cooled to −30° C. To this, 901 mg of ethyl o-phenylenephosphate is added. While stirring, the temperature of the reaction mixture is allowed to rise gradually up to −15° C. in 1.5 hours. After further stirring in an ice water bath for 8 hours and at room temperature for 15 hours, the solvent is evaporated under reduced pressure. The residue is treated with a mixture of acetonitrile and water (6:1) and filtered. The filtrate is purified by column chromatography (on 100 g of silica gel, developed and eluted with aqueous acetonitrile), and the eluate is concentrated under reduced pressure, and purified again with column chromatography (on 100 ml of XAD-2, developed and eluted with water and 5% and 10% ethanol). The eluate is concentrated under reduced pressure and lyophilized to give 91 mg of the desired compound as a pale yellow powder.

IR spectrum $\nu_{max}^{KBr}$cm$^{-1}$:1 3400, 1764, 1660, 1610.

NMR spectrum (D$_6$-DMSO)δ: 2.89(3H,s), 3.83(3H,s), 5.02(1H,d,J=5 Hz), 5.66(1H,d.d,J=5 Hz,J=7 Hz), 6.72(1H,s), 7.17(2H,s), 7.97(1H,d.d,J=5 Hz,J=7 Hz), 9.34(1H,d.d,J=2 Hz, J=5 Hz), 9.53(1H,d,J=7 Hz), 9.81(1H,d.d,J=2 Hz,J=7 Hz).

Elemental analysis for $C_{20}H_{19}N_9O_5S_2.4H_2O$, Calcd. (%): C,39.93; H,4.52; N,20.95. Found (%): C,39.88; H,4.65; N,20.79.

EXAMPLE 18

7β-[2-(2-Aminothiazol-4-yl)-2(Z)-methoxyiminoacetamido]- 3-(7-ethoxycarbonylmethylthio-5-methyl-[1,2,4]-triazolo[1,5-a]pyrimidiniium-1-yl)methyl-3-cephem-4-carboxylate.

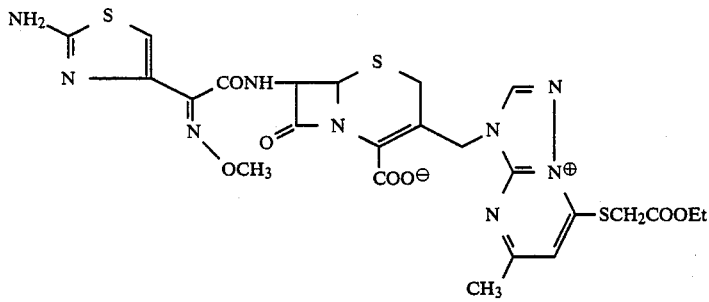

Tri(n-butyl)amine salt of 7β-[2-(2-aminothiazol-4-yl)-2(Z)-methoxyiminoacetamido]-3-hdyroxymethyl-3-cephem-4-carboxylic acid and 7-ethoxycarbonylmethylthio-5-methyl[1,2,4]triazolo[1,5-a]-pyrimidine are treated by the same procedure as to that in Example 17 to yield the desired compoundas a pale yellow powder.

IR spectrum $\nu_{max}^{KBr}$cm$^{-1}$: 3420, 1765, 1735, 1670, 1610.

NMR spectrum (d$_6$-DMSO)δ: 1.26(3H, t,J=7 Hz, 2.76(3H,s), 3.79(3H,s), 4.24(2H,q,J=7 Hz, 4.57(2H,s), 5.01(1H,d,J=5 Hz), 5.09(2H,ABq,J=14 Hz), 5.67(1H,d.d,J=5 Hz,J=8 Hz), 6.71(1H,s), 7.18(2H,s), 7.81(1H,s), 9.51(1H,d,J=8 Hz), 10.05 (1H,s).

EXAMPLE 19

7β-[2-(2-Aminothiazol-4-yl)-2(Z)-methoxyiminoacetamido]-3-[(6-ethoxycarbonylmethylthio-[1,2,4]triazolo[4,3-b]pyridazinium-1- and -2-yl)methyl]-3-cephem-4-carboxylate.

gradually up to 0° C. in 2 hours. The mixture is stirred further for 6 hours in an ice water bath, and the solvent is evaporated off under reduced pressure. The residue is purified by column chromatography (on 70 g of silica gel, developed and eluted with aqueous acetonitrile). The eluate is concentrated under reduced pressure and the residue is purified again by column chromatography (on 100 ml of XAD-2, developed and eluted successively with water, 10% and 20% ethanol). The eluate is then lyophilized, to yield the desired compounds as a 2:1 mixture (pale yellow powder, 131 mg).

IR spectrum $\nu_{max}^{KBr}$cm$^{-1}$:3420, 1772, 1765, 1770, 1610.

NMR spectrum (d$_6$-DMSO-D$_2$O)δ: 1.36(3H,t,J=7 Hz), 4.02(3H,s), 4.34(2H,q,J=7 Hz), 6.95(1H,s), 7.77, 8.07(total 1H, each d,J=10 Hz), 8.35, 8.81 (total 1H, each d, J=10 Hz).

Elemental analysis for C$_{23}$H$_{23}$N$_9$O$_7$S$_3$.7/2H$_2$O, Calcd. (%): C,39.65; H,4.34; N,18.09. Found (%): C,39.49; H,4.23; N,17.87.

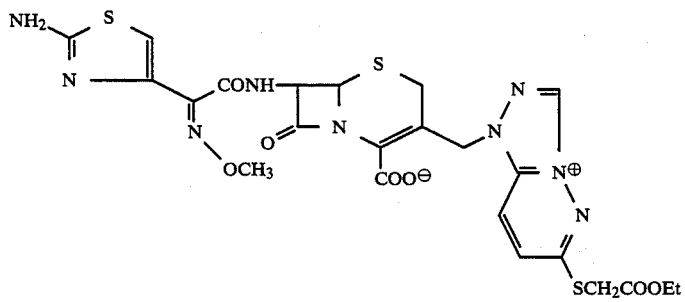

and

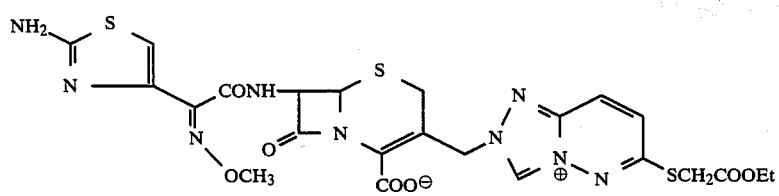

Tri(n-butyl)amine salt of 7β-[2-(2-aminothiazol-4-yl)-b 2(Z)-methoxyiminoacetamido]-3-hydroxymethyl-3-cephem-4-carboxylic acid, 599 mg, and 715 mg of 6-ethoxycarbonylmethylthio-[1,2,4]triazolo[4,3-b]pyridazine are dissolved in 20 ml of dry dichloromethane and cooled to −30° C., to which 697 mg of 2-phenyl-2-oxo-1,3,2-benzodioxaphosphor is added. While stirring, the temperature of the reaction mixture is allowed to rise

EXAMPLE 20

7β-[2-(2-Aminothiazol-4-yl)-2(Z)-methoxyiminoacetamido]-3-[(6-methoxy-[1,2,4]triazolo[4,3-b]pyridazinium-1- and 2-yl)methyl]-3-cephem-4-carboxylate.

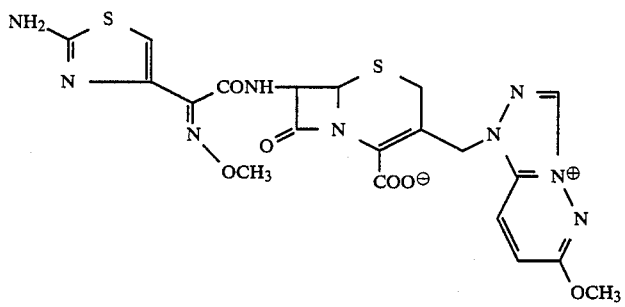

and

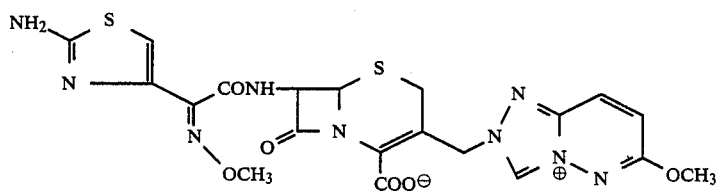

Tri(n-butyl)amine salt of 7β-[2-(2-aminothiazol-4-yl)-2(Z)-methoxyiminoacetamido]-3-hydroxymethyl-3-cephem-4-carboxylic acid and 6-methoxy-[1,2,4]triazolo[4,3-b]pyridazine are treated by the same procedure as that in Example 19 to yield the desired compounds as a 4:3 mixture.

IR spectrum $\nu_{max}^{KBr}$cm$^{-1}$: 3410, 1765, 1660, 1610.

NMR spectrum (D$_2$O)δ: 4.06(3H,s), 4.19, 4.22(total 3H, each s), 6.96, 6.97 (total 1H, each s), 7.45, 7.74 (total 1H, each d, J-10 Hz), 8.28, 8.71 (total 1H, each d, J=10 Hz).

EXAMPLE 21

7β-[2-(2-Aminothiazol-4-yl)-2(Z)-methoxyiminoacetamido]-3-[(6-methoxy-3-methyl-[1,2,4]triazolo[4,3-b]pyridazinium-1- and 2-yl)methyl]-3-cephem-4-carboxylate.

Trin(n-butyl)amine salt of 7β-[2-(2-aminothiazol-4-yl)-2(Z)-methoxyiminoacetamido]-3-hydroxymethyl-3-cephem-4carboxylic acid and 6-methoxy-3-methyl-[1,2,4]triazolo[4,3-b]pyridazine are treated by the same procedure as that in Example 19, to yeild the desired compounds in a 3:2 mixture.

IR spectrum $\nu_{max}^{KBr}$cm$^{-1}$:3400, 1768, 1665, 1614.

NMR spectrum (d$_6$-DMSO)δ: 2.75, 3.06 (total 3H, each s), 3.80, 3.82 (total 3H, each s), 4.10(3H,s), 6.69, 6.72 (total 1H, each s), 7.19 (2H,br.s), 7.52, 7.86 (total 1H, each d, J=10 Hz), 8.51, 9.54 (total 1H, each d, J=10 Hz), 9.45, 9.51 (total 1H, each d, J=8 Hz).

EXAMPLE 22

7β-[2(2-Aminothiazol-4-yl)-2(Z)-methoxyiminoacetamido]-3-[6-chloro-3-methyl-[1,2,4]triazolo[4–3,b]pyridazinium-1- and 2-yl)methyl]-3-cephem-4-carboxylate.

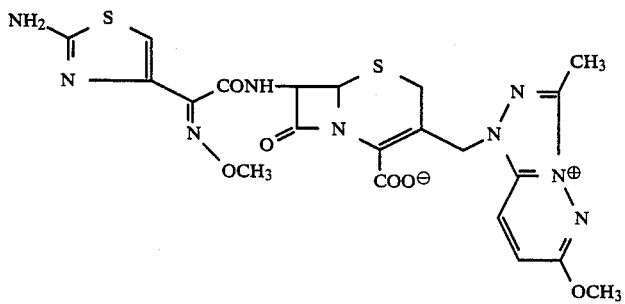

and

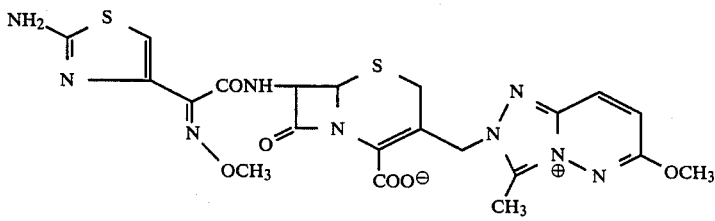

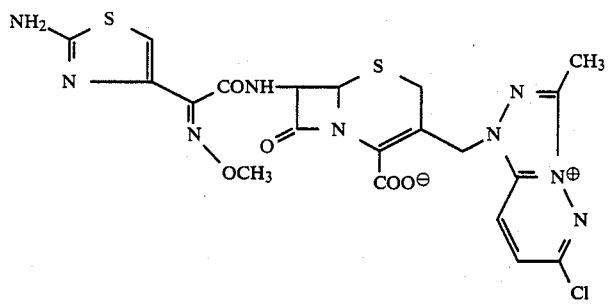

and

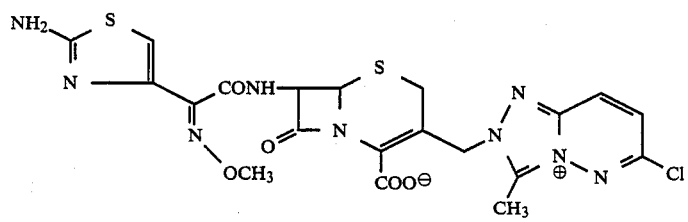

Tri(n-butyl)amine salt of 7β-[2-(2-aminothiazol-4-yl)-2(Z)-methoxyiminoacetamido]-3-hydroxymethyl-3-cephem-4-carboxylic acid and 6-chloro-3-methyl-[1,2,4]triazolo[4,3-b]pyridazine are treated by the same procedure as to that in Example 19, to yield the desired compounds in a 2:1 mixture.

IR spectrum $\nu_{max}^{KBr}$cm$^{-1}$: 3420, 1762, 1660, 1608.

NMR spectrum (d$_6$-DMSO-D$_2$O)δ: 2.95, 3.17 (total 3H, each s), 4.07(3H,s), 7.04(1H,s), 7.88, 8.21 (total 1H, each d, J=10 Hz), 8.48, 8.92 (total 1H, each d, J=10 Hz).

EXAMPLE 23

7β-[2-(2-Aminothiazol-4-yl)-2(Z)-methoxyiminoacetamido]-3-[(6-chloro-[1,2,4]trizolo[4,3-b]pyridazinium-1- and 2-yl)methyl]-3-cephem-4-carboxylate.

Tri(n-butyl)amine salt of 7β-[2-(2-aminothiazol-4-yl)-2(Z)-methoxyiminoacetamido]-3-hydroxymethyl-3-cephem-4-carboxylic acid and 6-chloro-[1,2,4]triazolo[4,3-b]pyridazine are treated by the same procedure as that in Example 19, to yield the desired compounds as a 2:1 mixture.

IR spectrum $\nu_{max}^{KBr}$cm$^{-1}$: 3410, 1768, 1662, 1610.

NMR spectrum (d$_6$-DMSO-D$_2$O)δ: 4.04(3H,s), 6.99(1H,s), 7.94, 8.25(total 1H, each d, J=10 Hz), 8.59, 9.02 (total 1H, each d, J=10 Hz).

EXAMPLE 24

7β-[2-(2-Aminothiazol-4-yl)-2(Z)-methoxyiminoacetamido]-3-[6-(2-hydroxyethylthio)-[1,2,4]triazolo[4,3-b]- pyridazinium-1- and 2-yl)methyl]-3-cephem-4-carboxylate.

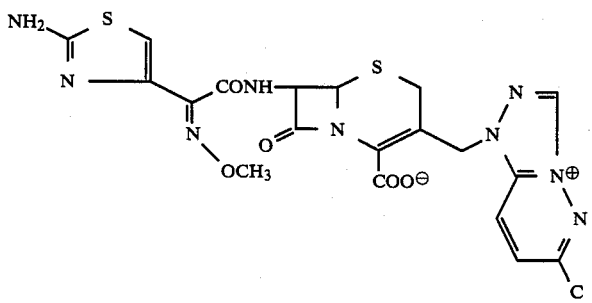

and

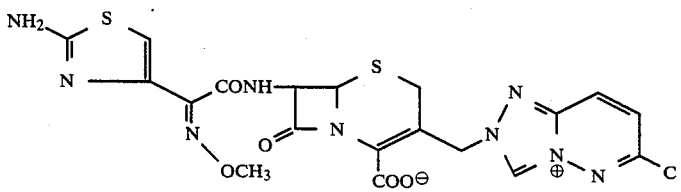

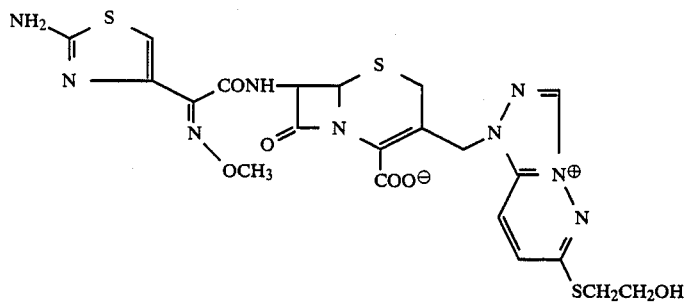

and

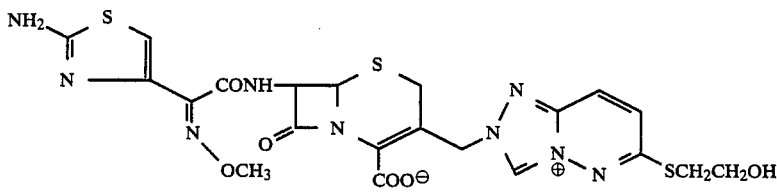

Tri(n-butyl)amine salt of 7β-[2-(2-aminothiazol-4-yl)-2(Z)-methoxyiminoacetamido]-3-hydroxymethyl-3-cephem-4-carboxylic acid and 6-(2-hydroxyethylthio)-[1,2,4]triazolo[4,3-b]pyridazine are treated by the same procedure as that in Example 19 to yield the desired compounds in a 2:1 mixture.

IR spectrum $v_{max}^{KBr}cm^{-1}$: 3380, 1760, 1656, 1605.
NMR spectrum (D$_2$O-CD$_3$CN)δ: 3.95(3H,s), 6.87(1H,s), 7.53, 7.85(total 1H, each d,J=10 Hz), 8.12, 8.62 (total 1H, each d, J=10 Hz).

EXAMPLE 25

7β[2-(2-Aminothiazol-4-yl)-2(Z)-methoxyiminoacetamido]-3-[(3-methyl[1,2,4]triazolo[4,3-a]pyrimidinium-1yl)methyl]-3-cephem-4-carboxylate.

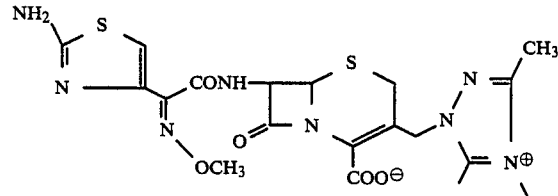

Tri(n-butyl)amine salt of 7β-[2-(2-aminothiazol-4-yl)-2(Z)-methoxyiminoacetamido]-3-hydroxymethyl-3-cephem-4-carboxylic acid, 599 mg, and 402 mg of 3-methyl-[1,2,4]triazolo[4,3-a]pyrimidine are dissolved in 20 ml of dry dichloromethane and the mixture is cooled to −30° C. To this, 697 mg of 2-phenyl-2-oxo-1,3,2-benzodioxaphosphole is added. The reaction mixture is stirred so that the temperature is allowed to rise gradually up to −20° C. in 1 hour. After further mixing in an ice bath for 4 hours, the solvent is evaporated off under reduced pressure, and the residue is purified by column chromatography (on 100 g of silica gel, developed and eluted with aqueous acetonitrile). The eluate is concentrated under reduced pressure, and the residue is purified again by column chromatography (on 100 ml of XAD-2, developed and eluted with water and 10% ethanol). The eluate is lyophilized to yield 12 mg of the desired compound as a colorless powder.

IR spectrum $v_{max}^{KBr}cm^{-1}$: 3410, 1762, 1610.
NMR spectrum (D$_2$O)δ: 3.21(3H,s), 4.07(3H,s), 5.32(1H,d, J=5 Hz), 5.69(2H,ABq,J=14 Hz), 5.90(1H,d,J=5 Hz), 7.05(1H,s), 7.63(1H,d.d,J=4 Hz,J=7 Hz).

EXAMPLE 26

7-[2-(5-Amino-1,2,4-thiadiazol-3-yl)-2(Z)-methoxyiminoacetamido]-3-([1,2,4]triazolo[1,5-b]pyridazinium-1-yl)methyl-3-cephem-4-carboxylate

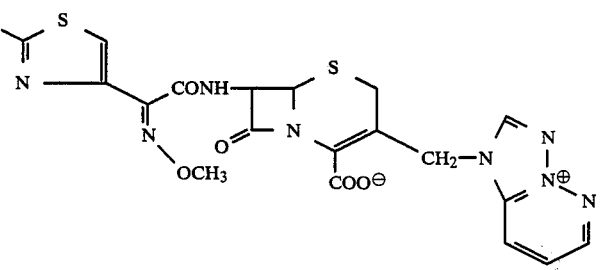

Tributylammonium 7-[2-(5-amino-1,2,4-thiadiazol-3-yl)-2(Z)-methoxyiminoacetamido]-3-hydroxymethyl-3-cephem-4carboxylate (0.6 g) and [1,2,4]triazolo[1,5-b]pyridazine (0.24 g) are dissolved in 15 ml of dichloromethane and the resulting solution is cooled to −30° to −40° C. To this mixture is added 0.41 g of ethyl o-phenylenephosphate and the reaction mixture is warmed up to 0° C. over 3 hours with stirring. Diethyl ether (5 ml) is then added to the reaction mixture and

EXAMPLE 27

7-[2-(5-Amino-1,2,4-thiadiazol-3-yl)-2(Z)-methoxyiminoacetamido]-3-(6-methyl[1,2,4]triazolo[1,5-b]pyridazinium-1-yl)methyl-3-cephem-4-carboxylate.

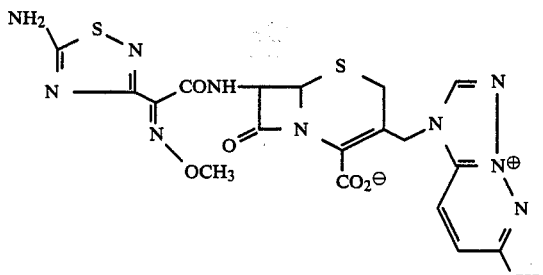

7-[2-(5-Amino-1,2,4-thiadiazol-3-yl)-2(Z)-methoxyiminoacetamido-3-hydroxymethyl-3-cephem-4-carboxylic acid tributylamine salt and 6-methyl[1,2,4]triazolo[1,5-b]pyridazine are reacted as in Example 26 giving the title compound.

IR spectrum $\nu_{max}^{KBr}$cm$^{-1}$: 1770, 1660, 1610, 1510.

NMR spectrum (d$_6$-DMSO)δ: 2.62(3H,s), 3.91(3H,s), 5.02(1H, d,J=4.5 Hz), 5.4-5.8(3H,m), 7.55(1H,d,J=9 Hz), 8.06(2H,br.s), 8.30(1H,d,J=9 Hz), 8.53(1H,s), 9.44(1H,d,J=8 Hz).

Elemental Analysis for C$_{19}$H$_{18}$N$_{10}$O$_5$S$_2$.13/8H$_2$O, Calcd. (%): C,35.24; H,4.82; N,21.63. Found (%): C,35.01; H,4.79; N,21.48.

EXAMPLE 28

7-[2-(5-Amino-1,2,4-thiadiazol-3-yl)-2(Z)-methoxyiminoacetamido]- 3-(6-methylthio-[1,2,4]triazolo[1,5-b]pyridazinium-1-yl)methyl-3-cephem-4-carboxylate

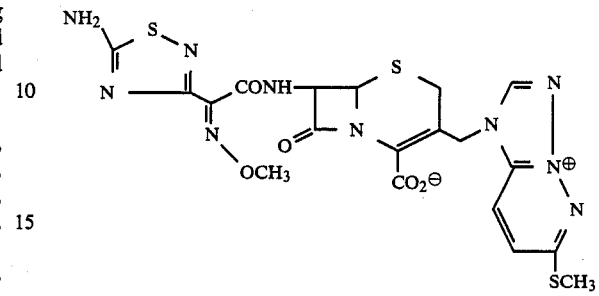

7-[2-(5-amino-1,2,4-thiadiazol-3-yl)-2(Z)-methoxyiminoacetamido]-3-hydroxymethyl-3-cephem-4-carboxylic acid tributylamine salt and 6-methylthio-[1,2,4]triazolo[1,5-b]pyridazine are reacted as in Example 26 giving the title compound.

IR spectrum $\nu_{max}^{KBr}$cm$^{-1}$: 1770, 1660, 1610, 1530.

NMR spectrum (d$_6$-DMSO)δ: 3.18(3H,s), 3.26 & 3.56(2H,ABq,J=18 Hz), 3.86(3H,s), 5.14(1H,d,J=4.5 Hz), 5.70(2H,br.s), 5.97(1H,d.d,J=4.5 Hz & 8 Hz), 7.54(1H,d,J=9 Hz), 8.04(2H,br. s), 8.24(1H,s), 8.72(1H,d,J=9 Hz), 9.46(1H,d,J=8 Hz).

Elemental Analysis for C$_{19}$H$_{18}$N$_{10}$O$_5$S$_3$.3H$_2$O, Calcd. (%): C,37.01; H,3.92; N,22.71. Found (%): C,37.18; H,3.94; N,22.82.

EXAMPLE 29

7-[2-(5-Amino-1,2,4-thiadiazol-3-yl)-2(Z)-methoxyiminoacetamido]-3-(6-dimethylamino-[1,2,4]triazolo[1,5-b]pyridazinium-1-yl)methyl-3-cephem-4-carboxylate.

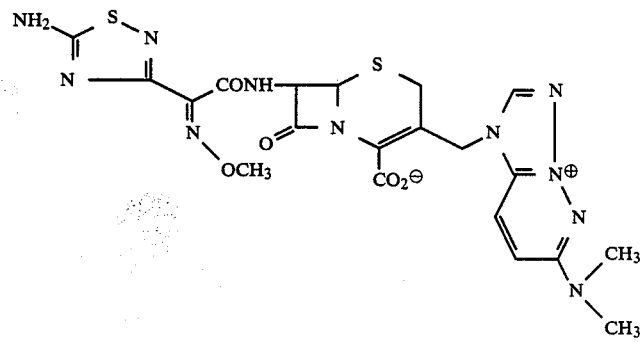

7-[2-(5-Amino-1 2 4-thiadiazol-3-yl)-2(Z)-methoxyimino acetamido-3-hydroxymethyl-3-cephem-4-carboxylic acid tributylamine salt and 6-dimethylamino-[1,2,4]triazolo[1,5b]pyridazine are reacted as in Example 26 giving the title compound.

IR spectrum $\nu_{max}^{KBr}$cm$^{-1}$: 1775, 1670, 1610, 1525.

NMR spectrum (d$_6$-DMSO)δ:3.20(6H,s), 3.92(3H,s), 5.03(1H, d,J=4.5 Hz), 5.37(2H,br.s), 5.71(1H,d.d,J=4.5 Hz & 8 Hz), 7.34(1H,d,J=9 Hz), 8.00(2H,br.s), 8.19(1H,s), 8.73(1H,d, J=9 Hz), 9.44(1H,d,J=8 Hz).

Elemental Analysis for C$_{19}$H$_{17}$N$_9$O$_5$S$_2$.5H$_2$O, Calcd. (%): C,38.03; H,4.63; N,24.39. Found (%): C,37.74; H,4.63; N,24.21.

EXAMPLE 30

7-[2-(2-Aminothiazol-4-yl)-2(Z)-methoxyiminoacetamido]-3-[[1,2,4]triazolo[1,5-b]pyridazinium-1-yl]-methyl-3-cephem-4-carboxylate

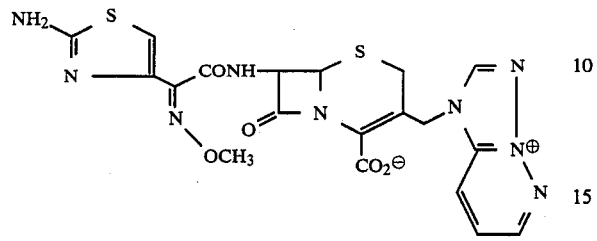

7-[2-(2-Aminothiazol-4-yl)-2(Z)-methoxyiminoacetamido]-3-hydroxymethyl-3-cephem-4-carboxylic acid tributylamine salt and [1,2,4]triazolo[1,5-b]pyridazine are reacted as in Example 26 giving the title compound.

IR spectrum $v_{max}^{KBr}$cm$^{-1}$: 1760, 1660, 1610, 1515.
NMR spectrum (d$_6$-DMSO)δ: 3.83(3H,s), 4.91(1H,d,J=4.5 Hz), 5.32–5.58(3H,m), 6.72(1H,s), 7.16(2H,br.s), 7.65(1H,d.d, J=4.5 Hz & 9 Hz), 8.43(1H,d.d,J=9 Hz & 1.5 Hz), 8.62(1H,s), 8.73(1H,d.d,J=4.5 Hz & 1H), 9.49(1H,d,J=8 Hz).

Elemental Analysis for $C_{19}H_{17}N_9O_5S_2.5H_2O$, Calcd. (%): C,37.68; H,4.49; N,20.82. Found (%): C,37.86; H,4.38; N,20.98.

EXAMPLE 31

7-[2-(2-Aminothiazol-4-yl)-2(Z)-methoxyiminoacetamido]-3-[(6-methylthio[1,2,4]triazolo[1,5-b]pyridazinium-1-yl)methyl-3-cephem-4-carboxylate

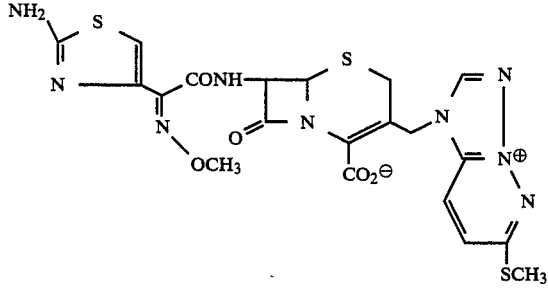

7-[2-(2-Aminothiazol-4-yl)-2(Z)-methoxyiminoacetamido]3-hydroxymethyl-3-cephem-4-carboxylic acid tributylamine salt and 6-methythio-[1,2,4]triazolo[1,5-b]pyridazine are reacted as in Example 26 giving the title compound.

IR spectrum $v_{max}^{KBr}$cm$^{-1}$: 1765, 1665, 1620, 1520.
NMR spectrum (d$_6$-DMSO-D$_2$O)δ: 3.11(3H,s), 3.93(3H,s), 5.06(1H,d,J=4.5 Hz), 5.43(2H,br.s), 5.82(1H,d,J=4.5 Hz), 6.83(1H,s), 7.62(1H,d,J=9 Hz), 8.23(1H,s), 8.48(1H,d,J=9 Hz).

EXAMPLE 32

7-[2-2-Aminothiazol-4-yl)-2(Z)-methoxyiminoacetamido]-3-[(6-methoxy-1,2,4]triazolo[1,5-b]pyridazinium-1-yl)methyl-3-cephem-4-carboxylate.

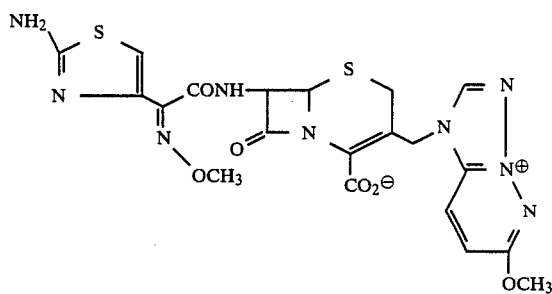

7-[2-(2-Aminothiazol-4-yl)-2(Z)-methoxyiminoacetamido]-3-hydroxymethyl-3-cephem-4-carboxylic acid tributylamine salt and 6-methoxy-[1,2,4]triazolo[1,5-b]pyridazine are reacted as in Example 26 giving the title compound.

IR spectrum $v_{max}^{KBr}$cm$^{-1}$: 1770, 1665, 1615, 1520.
NMR spectrum (D$_2$O-CD$_3$CN)δ: 3.50(2H,ABq,J=18 Hz), 4.00(3H,s), 4.23(3H,s), 5.29(1H,d,J=5 Hz), 5.45(2H,ABq,J=14 Hz),5.86(1H,d, J=5 Hz), 6.97(1H,s), 7.88(1H,d,J=10 Hz), 8.82(1H,d,J=10 Hz), 9.41(1H,s).

Elemental Analysis for $C_{20}H_{19}N_9O_6S_2.2.5H_2O$, Calcd. (%): C,40.67; H,4.10, N,21.34. Found (%): C, 40.77; H, 3.99; N, 20.51.

What we claim is:

1. A compound of the formula

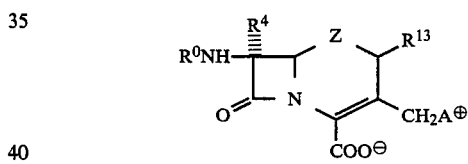

wherein, $R^0$ is an acyl group derived from a carboxylic acid which is conventional in the cephalosporine field; Z is S, or S→O; $R^4$ is a hydrogen atom, a methoxy group, or a formamide group; $R^{13}$ is a hydrogen atom, a methyl group, a hydroxyl group, or a halogen atom; A⊕ is an optionally substituted condensed triazolio group of the formula:

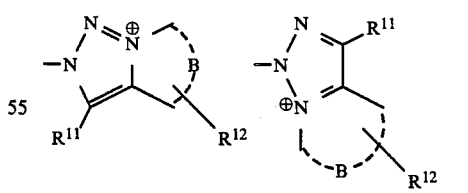

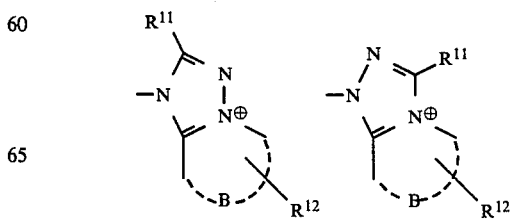

-continued

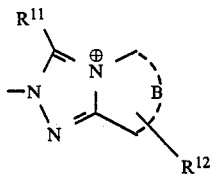

wherein B stands for a group forming a 5- or 6- membered aromatic heterocyclic ring containing one to four hetero atoms selected from N, S and O, the heterocyclic ring being optionally condensed with a benzene ring or another 5- or 6- membered heterocyclic ring defined just above, $R^{11}$ is a hydrogen atom or a substituent selected from a class consisting of a hydroxy $C_{1-6}$ alkyl, $C_{1-6}$ alkyl, $C_{1-6}$ alkoxy, $C_{1-6}$ alkylthio, $C_{1-6}$ alkoxycarbonyl $C_{1-6}$ alkylthio, hydroxy $C_{1-6}$ alklthio, amino, mono $C_{1-6}$ alkylamino, di $C_{1-6}$ alkylamino, cyano, carbamoyl and halogen and $R^{12}$ is one or two substituents, the same or different selected from the groups mentioned for the substituent $R^{11}$, or a pharmaceutically acceptable salt or ester thereof.

2. A compound as claimed in claim 1, wherein $R^0$ is an acyl group of the formula:

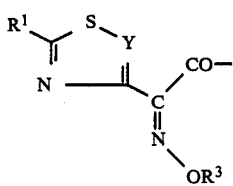

wherein $R^1$ is an amino group or a protected amino; Y is N or $CR^2$ where $R^2$ is a hydrogen atom or a halogen atom and $R^3$ is (i) hydrogen atom, (ii) straight chain $C_{1-3}$ alkyl group, or (iii) straight chain or branched $C_{1-3}$ alkyl group, allyl group or propargyl substituted with one substituent to three substituents selected from a class consisting of halogen atom, hydroxyl group, alkoxy group, carboxyl group, alkoxycarbonyl group and cyanp groups.

3. A compound as claimed in claim 2 wherein Z is S, $R^4$ is a hydrogen atom, and $R^{13}$ is a hydrogen atom.

4. A compound as claimed in claim 2 wherein $R^3$ is a $C_{1-3}$ alkyl group which may be substituted with hydroxyl, alkoxy, carboxyl, alkoxycarbonyl, cyano, or halogen, the number of the substituents being one to three and the substituent being the same or different.

5. The compound as claimed in claim 2 wherein $A^\oplus$ is

[1,2,3]triazolo[1,5-a]pyridinium-2-yl,
[1,2,3]triazolo[1,5-a]pyridinium-3-yl,
[1,2,4]triazolo[1,5-a]pyridiuium-1-yl,
[1,2,4]triazolo[4,3-a]pyridinium-1-yl
[1,2,4]triazolo[4,3-a]pyridinium-2-yl
[1,2,4]triazolo[1,5-a]pyrimidinium-1-yl,
[1,2,4]triazolo[4,3-a]pyrimidinium-1-yl
[1,2,4]triazolo[4,3-b]pyridazinium-1-yl
[1,2,4]triazolo[4,3-b]pyridazinium-2-yl or
[1,2,4]triazolo[1,5-b]pyridazinium-1-yl
which may be substituted with one substituent to three substituents, which are the same or different, selected from a class of a hydroxy $C_{1-6}$ alkyl, $C_{1-6}$ alkyl, $C_{1-6}$ alkoxy, $C_{1-6}$ alkylthio, $C_{1-6}$ alkoxycarbonyl $C_{1-6}$ alkylthio, hydroxy $C_{1-6}$ alkylthio, amino, mono $C_{1-6}$ alkylamino, di $C_{1-6}$ alkylamino, cyano, carbamoyl and halogen.

6. A compound according to claim 2, namely 7β-[2-(2-aminothiazol-4-yl)-2-(Z)-methoxyiminoacetamido]-3-[(5-methyl-[1,2,4]triazolo[1,5-a]pyridinium-1-yl)methyl]-3-cephem-4-carboxylate, or a pharmaceutically acceptable salt thereof.

7. A compound according to claim 2, namely 7β-[2-(2-aminothiazol-4-yl)-2-(Z)-methoxyiminoacetamido]-3-[(5-methyl-[1,2,3]triazolo[1,4-a]pyridinium-2-yl)methyl]-3-cepham-4-carboxylate, or a pharmaceutically acceptable salt thereof.

8. A compound according to claim 2, namely 7β-[2-(2-amino-5-chlorothiazol-4-yl)-2-(Z)-methoxyiminoacetamido]-3-[(5-methyl-[1,2,4]triazolo[1,5-a]pyridinium-1-yl)methyl]-3-cepham-4-carboxylate, or a pharmaceutically acceptable salt thereof.

9. A compound according to claim 2, namely 7β-[2-(5-amino-1,2,4-thiadiazol-3-yl)-2(Z)-methoxyiminoacetamido]3-[(5-methyl[1,2,4]triazolo[1,5-a]pyridinium-1-yl)methyl]3-cephem-4-carboxylate, or a pharamceutically acceptable salt thereof.

10. A compound according to claim 2, namely 7β-[2-(2-aminothiazol-4-yl)-2(Z)-methoxyiminoacetamido]-3-[(6-methoxy-[1,2,4]triazolo[4,3-b]pyridazinium-1- or 2-yl) methyl]-3-cephem-4-carboxylate, or a pharmaceutically acceptable salt thereof.

11. A compound according to claim 2, namely, 7-[2-(2-aminothiazol-4-yl)-2(Z)-methoxyiminoacetamido]-3-[(6-methoxy[1,2,4]triazolo[1,5-b]pyridazinium-1-yl)methyl-3-cephem-4-carboxylate, or a pharmaceutically acceptable salt thereof.

12. An antimicrobial composition containing at least one of the compounds having the formula

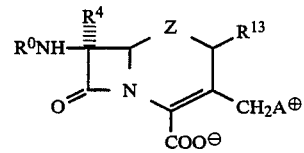

wherein, $R^0$ is an acyl group derived from a carboxylic acid which is conventional in the cephalosporine field; Z is S, or S→O; $R^4$ is a hydrogen atom, a methoxy group, or a formamide group; $R^{13}$ is a hydrogen atom, a methyl group, a hydroxyl group, or a halogen atom; $A^\oplus$ is an optionally substituted condensed triazolio group of the formula:

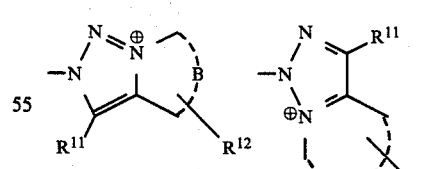

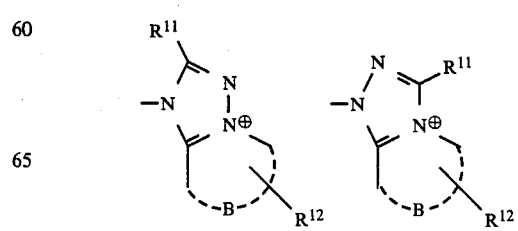

-continued

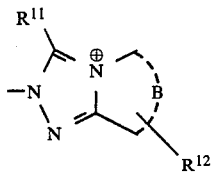

wherein B stands for a group forming a 5- or 6- membered aromatic heterocyclic ring containing one to four hetero atoms selected from N, S and O, the heterocyclic ring being optionally condensed with a benzene ring or another 5- or 6- membered heterocyclic ring defined just above, $R^{11}$ is a hydrogen atom or a substituent selected from a class consisting of a hydroxy $C_{1-6}$ alkyl, $C_{1-6}$ alkyl, $C_{1-6}$ alkoxy, $C_{1-6}$ alkylthio, $C_{1-6}$ alkoxycarbonyl $C_{1-6}$ alkylthio, hydroxy $C_{1-6}$ alkylthio, amino mono $C_{1-6}$ alkylamino, di $C_{1-6}$ alkylamino, cyano, carbamoyl and halogen and $R^{12}$ is one substituent or two, the same or different, substituents selected from the groups mentioned for the substituent $R^{11}$, or pharmaceutically acceptable salts or esters.

* * * * *